US012630539B2

(12) United States Patent
Huang et al.

(10) Patent No.: US 12,630,539 B2
(45) Date of Patent: May 19, 2026

(54) AMIDE COMPOUND, PHARMACEUTICAL COMPOSITION AND USE THEREOF

(71) Applicant: SHENZHEN BO LI JIAN MEDICINE CO., LTD., Guangdong (CN)

(72) Inventors: Liye Huang, Shenzhen (CN); Hua Li, Shenzhen (CN); Huabin Liu, Shenzhen (CN); Xinmiao Zhang, Shenzhen (CN)

(73) Assignee: ARTIVILA (SHENZHEN) INNOVATION CENTER, LTD., Shenzhen (CN)

( * ) Notice: Subject to any disclaimer, the term of this patent is extended or adjusted under 35 U.S.C. 154(b) by 337 days.

(21) Appl. No.: 18/254,089

(22) PCT Filed: Nov. 24, 2021

(86) PCT No.: PCT/CN2021/132652

§ 371 (c)(1),
(2) Date: May 23, 2023

(87) PCT Pub. No.: WO2022/111499

PCT Pub. Date: Jun. 2, 2022

(65) Prior Publication Data

US 2023/0416237 A1 Dec. 28, 2023

(30) Foreign Application Priority Data

Nov. 26, 2020 (CN) ........................ 202011348554.2

(51) Int. Cl.
*C07D 403/14* (2006.01)
*C07D 401/14* (2006.01)
*C07D 405/14* (2006.01)

(52) U.S. Cl.
CPC ......... *C07D 403/14* (2013.01); *C07D 401/14* (2013.01); *C07D 405/14* (2013.01)

(58) Field of Classification Search
CPC .................................................. C07D 403/14
See application file for complete search history.

(56) References Cited

FOREIGN PATENT DOCUMENTS

| | | | |
|---|---|---|---|
| CN | 108368091 | A | 8/2018 |
| CN | 108570048 | A | 9/2018 |
| CN | 111032630 | A | 4/2020 |
| JP | 2006522768 | A | 10/2006 |
| JP | 2009525337 | A | 7/2009 |
| JP | 2018529770 | A | 10/2018 |
| JP | 2020506171 | A | 2/2020 |
| WO | 2010/129802 | A1 | 11/2010 |
| WO | 2012/139930 | A1 | 10/2012 |
| WO | 2020/057669 | A1 | 3/2020 |
| WO | 2020/101382 | A1 | 5/2020 |
| WO | 2020/156271 | A1 | 8/2020 |
| WO | 2020/211839 | A1 | 10/2020 |

OTHER PUBLICATIONS

Venkatesh, J. Pharm. Sci. 89, 145-154 (2000) (p. 146, left column). J.*
G. Cannon, Chapter Nineteen in Burger's Medicinal Chemistry and Drug Discovery, Fifth Edition, vol. I: Principles and Practice , Wiley-Interscience 1995, pp. 783-802, 784.*
Hu, Signal Transduction and Targeted Therapy (2021) 6:402.*
International Search Report, dated Jan. 28, 2022, issued in corresponding International Patent Application No. PCT/CN2021/132652.
Notice of Reasons for Refusal, dated May 24, 2024, issued in corresponding Japanese Patent Application No. 2023-532714.
Extended European Seach Report, dated Aug. 29, 2024, issued in corresponding European Patent Application No. 21897000.2.

(Continued)

*Primary Examiner* — Nizal S Chandrakumar
(74) *Attorney, Agent, or Firm* — Howson & Howson, LLP; Kathleen D. Rigaut; Richard F. Kane

(57) ABSTRACT

Provided in the present application are an amide compound, and an isomer, a pharmaceutically acceptable salt, and a pharmaceutical composition thereof, and the use thereof. The amide compound has a structure as represented by formula I. The amide compound of the present application has a significant JAK kinase inhibitory activity, especially a JAKI kinase inhibitory activity, has a higher inhibitory activity on JAK1 kinase than on JAK2 kinase, and can be used as a highly selective JAK1 kinase inhibitor. Therefore, the amide compound of the present application can be used for preparing drugs for treating JAK1 kinase-mediated diseases.

I

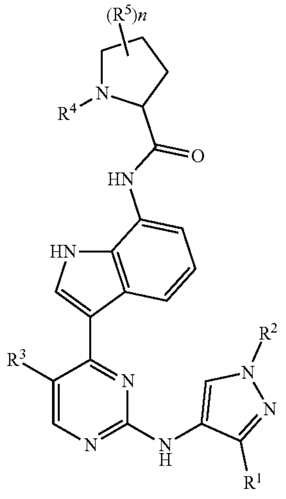

6 Claims, No Drawings

(56) References Cited

OTHER PUBLICATIONS

Su, Qibin et al., "Discovery of (2R)-N-[3-[2-[(3-Methoxy-1-methyl-pyrazol-4-yl)amino]pyrimidin-4-yl]-1H-indol-7-yl]-2-(4-methylpiperazin-1-yl)propenamide (AZD4205) as a Potent and Selective Janus Kinase 1 Inhibitor," Journal of Medicinal Chemistry, vol. 63, No. 9, Apr. 2020, pp. 4517-4527.

* cited by examiner

AMIDE COMPOUND, PHARMACEUTICAL COMPOSITION AND USE THEREOF

CROSS-REFERENCE TO RELATED APPLICATION(S)

This application is a § 371 of International Application No. PCT/CN2021/132652, filed Nov. 24, 2021, which claims priority to Chinese Patent Application No. 202011348554.2, filed Nov. 26, 2020 and entitled "AMIDE COMPOUND, PHARMACEUTICAL COMPOSITION AND USE THEREOF", the entire contents of each being incorporated by reference as though set forth in full.

TECHNICAL FIELD

The present application belongs to the technical field of pharmaceutical chemistry and particularly relates to an amide compound, a pharmaceutical composition containing the amide compound and a use of the amide compound or the pharmaceutical composition for preparing a medicament.

BACKGROUND

JAKs (Janus-associated kinases) are non-receptor tyrosine kinases and include four family members: JAK1, JAK2, JAK3 and TYK2. JAKs play a key role in the signaling of many cytokines and growth factors. When a cytokine binds to its receptor, JAK coupled to the receptor is phosphorylated and activated. The activated JAK phosphorylates the receptor of the cytokine and signal transducer and activator of transcription (STAT) proteins in sequence. Activated STAT proteins form a dimer and the dimer is transferred into the nucleus to regulate gene expression ("The regulation of JAKs in cytokine signaling and its breakdown in disease", Hammaren H. M. et al., Cytokine, 2019, 118, 48-63).

Since a JAK/STAT signaling pathway mediates the signaling of many cytokines, the imbalance of the JAK/STAT signaling pathway causes inflammations, autoimmune diseases and cancer ("The JAK-STAT Pathway: Impact on Human Disease and Therapeutic Intervention", O'Shea J. J. et al., Annual Review of Medicine, 2015, 66, 311-328). These diseases have been clinically proved to be treatable by inhibiting JAKs ("Therapeutic targeting of JAKs: from hematology to rheumatology and from the first to the second generation of JAK inhibitors", Bertsias G., Mediterranean Journal of Rheumatology, 2020, 31, Supp 1, 105-111). So far multiple non-selective JAK inhibitors have been approved for the treatment of inflammations and autoimmune diseases (e.g., tofacitinib and baricitinib) and primary myelofibrosis (e.g., ruxolitinib), but these drugs all have dose-limiting toxicities, such as side effects of anemia and thrombocytopenia ("Clinical efficacy of launched JAK inhibitors in rheumatoid arthritis", Taylor P. C., Rheumatology, 2019, 58, i17-126; "Safety and efficacy of baricitinib at 24 weeks in patients with rheumatoid arthritis who have an inadequate response to methotrexate", Keystone E. C. et al., Annals of the Rheumatic Diseases, 2015, 74, 333-340), which is because these inhibitors all inhibit JAK2 and thus interfere with signals of erythropoietin (EPO) and thrombopoietin (TPO) ("Selective JAKinibs: Prospects in Infammatory and Autoimmune Diseases", Virtanen A. T. et al., BioDrugs, 2019, 33, 15-32).

Of the four JAK family members, JAK1 is most widely involved in cytokine signaling and is the only member capable of pairing with the other three JAKs to regulate signaling. Due to this characteristic of JAK1, the JAK/STAT signaling pathway can be blocked by selectively inhibiting JAK1 without inhibiting other JAKs, especially JAK2 ("Selective JAKinibs: Prospects in Infammatory and Autoimmune Diseases", Virtanen A. T. et al., BioDrugs, 2019, 33, 15-32). Therefore, selective JAK1 inhibitors may be sufficient for treating inflammations, autoimmune diseases and cancer associated with disorders of the JAK/STAT signaling pathway. Selective JAK1 inhibitors (e.g., upadacitinib and filgotinib) disclosed so far are approved for the treatment of RA, but none of these inhibitors has a high selectivity for JAK2, which is less than three times in kinase assays ("In vitro and in vivo characterization of the JAK1 selectivity of upadacitinib (ABT-494)", Parmentier J. M. et al., BMC Rheumatology, 2018, 2, 23; "Preclinical Characterization of GLPG0634, a selective inhibitor of JAK1, for the treatment of inflammatory diseases", Van Rompaey L. et al., Journal of Immunology, 2013, 191, 3568-3577; "Triazolopyridines as Selective JAK1 Inhibitors: From Hit Identification to GLPG0634", Menet C. J. et al., Journal of Medicinal Chemistry, 2014, 57, 9323-9342).

Therefore, it is an urgent problem to be solved in the art to develop a compound which has a higher selectivity for JAK2 and a higher inhibitory effect on JAK1.

SUMMARY

The present application provides an amide compound, a pharmaceutical composition and a use thereof, wherein the amide compound has an effect of inhibiting JAK1 activity and good JAK2 selectivity.

In a first aspect, the present application provides an amide compound having a structure represented by Formula I:

Formula I

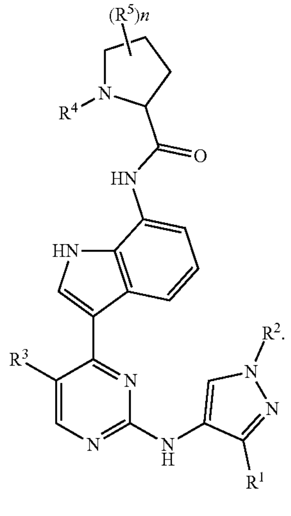

In Formula I, $R^1$ is selected from H, halogen, C1 to C6 linear or branched alkyl, C3 to C6 cycloalkyl or $OR^a$; wherein the linear or branched alkyl or the cycloalkyl is unsubstituted or substituted with 1 to 3 (e.g., 1, 2 or 3) $R^{1a}$.

$R^{1a}$ is selected from D or halogen.

In Formula I, $R^2$ is selected from H, C1 to C6 linear or branched alkyl, C3 to C10 cycloalkyl or C2 to C10 heterocycloalkyl; wherein the linear or branched alkyl, the cycloalkyl or the heterocycloalkyl is unsubstituted or substituted with 1 to 3 (e.g., 1, 2 or 3) $R^{2a}$.

$R^{2a}$ is selected from D, halogen, cyano, unsubstituted or halogenated C1 to C6 linear or branched alkyl, C3 to C6 cycloalkyl, C2 to C6 heterocycloalkyl, $OR^{a1}$, $SR^{a1}$, $NR^{b1}R^{c1}$, $COR^{a1}$, $CONR^{b1}R^{c1}$, $COOR^{a1}$, $SO_2R^{a1}$, $SO_2NR^{b1}R^{c1}$, $NR^{b1}COR^{a1}$, $NR^{d1}CONR^{b1}R^{c1}$, $NR^{b1}SO_2R^{a1}$, $NR^{d1}SO_2NR^{b1}R^{c1}$ or $SOR^{a1}$.

In Formula I, $R^3$ is selected from H, halogen, cyano, unsubstituted or halogenated C1 to C6 linear or branched alkyl, C2 to C6 alkenyl, C2 to C6 alkynyl or C3 to C6 cycloalkyl.

In Formula I, $R^4$ is selected from $SO_2R^{a2}$, $COR^{a2}$, $COOR^{a2}$, C3 to C10 cycloalkyl or C2 to C10 heterocycloalkyl; wherein the cycloalkyl or the heterocycloalkyl is unsubstituted or substituted with 1 to 5 (e.g., 1, 2, 3, 4 or 5) $R^{4a}$.

$R^{4a}$ is selected from D, halogen, cyano, C1 to C6 linear or branched alkyl, C3 to C6 cycloalkyl, C2 to C6 heterocycloalkyl, $OR^{a3}$, $SR^{a3}$, $NR^{b3}R^{c3}$, $COR^{a3}$, $CONR^{b3}R^{c3}$, $COOR^{a3}$, $SO_2R^{a3}$ or $SO_2NR^{b3}R^{c3}$; wherein the linear or branched alkyl, the cycloalkyl or the heterocycloalkyl is unsubstituted or substituted with 1 to 5 (e.g., 1, 2, 3, 4 or 5) $R^{4b}$.

$R^{4b}$ is selected from D, halogen, cyano, $OR^{a4}$ or $NR^{b4}R^{c4}$.

In Formula I, $R^5$ is selected from F, cyano, C1 to C6 linear or branched alkyl or $OR^{a5}$.

$R^a$, $R^{a1}$, $R^{b1}$, $R^{c1}$, $R^d$, $R^{a2}$, $R^{a3}$, $R^{b3}$, $R^{c3}$, $R^{a4}$, $R^{b4}$, $R^{c4}$ and $R^{a5}$ are each independently selected from H, C1 to C10 linear or branched alkyl, C2 to C10 alkenyl, C2 to C10 alkynyl, C3 to C10 cycloalkyl or C2 to C10 heterocycloalkyl; wherein the linear or branched alkyl, the alkenyl, the alkynyl, the cycloalkyl or the heterocycloalkyl is unsubstituted or substituted with 1 to 4 (e.g., 1, 2, 3 or 4) $R^6$.

$R^6$ is selected from D, halogen, cyano, hydroxyl, unsubstituted or halogenated C1 to C6 linear or branched alkyl, C2 to C6 alkenyl, C2 to C6 alkynyl, C3 to C6 cycloalkyl, C2 to C6 heterocycloalkyl, $OR^{a6}$, $SR^{a6}$, $NR^{b6}R^{c6}$, $COR^{a6}$, $CONR^{b6}R^{c6}$, $COOR^{d6}$, $SO_2R^{a6}$, $SO_2NR^{b6}R^{c6}$, $NR^{b6}COR^{a6}$, $NR^{d6}CONR^{b6}R^{c6}$, $NR^{b6}SO_2R^{a6}$, $NR^{d6}SO_2NR^{b6}R^{c6}$ or $SOR^{a6}R^{a6}$, $R^{b6}$, $R^{e6}$ and $R^{d6}$ are each independently selected from H, C1 to C10 linear or branched alkyl, C2 to C10 alkenyl, C2 to C10 alkynyl, C3 to C10 cycloalkyl or C2 to C10 heterocycloalkyl.

In Formula I, n is an integer selected from 0 to 3, for example, 0, 1, 2 or 3.

When n≥2, $R^5$ are not joined to each other or are joined by a chemical bond to form a 3- to 6-membered carbocycle or carboheterocycle. That is, two substituents $R^5$ joined to the same C atom or two substituents $R^5$ joined to two adjacent carbon atoms are not joined to each other or are joined by a chemical bond to form a ring which is a 3- to 6-membered (e.g., 3-membered, 4-membered, 5-membered or 6-membered) carbocycle or carboheterocycle.

In the present application, two substituents $R^{b1}$ and $R^{c1}$, $R^{b3}$ and $R^{c3}$, $R^{b4}$ and $R^{c4}$, $R^{b6}$ and $R^{c6}$ joined to the same N atom are not joined to each other or are joined by a chemical bond to form a heterocyclic group (N-containing heterocycle). The heterocyclic group is unsubstituted or substituted with 1 to 3 (e.g., 1, 2 or 3) substituents which are selected within the same range as $R^6$.

In the present application, the halogen includes F, Cl, Br or I; the same expressions involved hereinafter have the same meanings.

In the present application, the C1 to C10 linear or branched alkyl may each independently be C1, C2, C3, C4, C5, C6, C7, C8, C9 or C10 linear or branched alkyl, for example, including, but not limited to, methyl, ethyl, n-propyl, isopropyl, n-butyl, isobutyl, t-butyl, n-pentyl, isopentyl or neopentyl, etc.

The C3 to C10 cycloalkyl may each independently be C3, C4, C5, C6, C7, C8, C9 or C10 cycloalkyl, for example, including, but not limited to, cyclopropyl, cyclobutyl, cyclopentyl or cyclohexyl, etc.

The C2 to C10 heterocycloalkyl may each independently be C2, C3, C4, C5, C6, C7, C8, C9 or C10 heterocycloalkyl, wherein a heteroatom therein includes O, N, S, P or Si, etc. For example, the C2 to C10 heterocycloalkyl includes, but is not limited to, a tetrahydrofuran ring, a tetrahydropyrrole ring (pyrrolidine ring), a piperidine ring, etc.

The C1 to C6 linear or branched alkyl may each independently be C1, C2, C3, C4, C5 or C6 linear or branched alkyl, for example, including, but not limited to, methyl, ethyl, n-propyl, isopropyl, n-butyl, isobutyl, t-butyl, n-pentyl, isopentyl or neopentyl, etc.

The C3 to C6 cycloalkyl may each independently be C3, C4, C5 or C6 cycloalkyl, for example, including, but not limited to, cyclopropyl, cyclobutyl, cyclopentyl or cyclohexyl, etc.

The C2 to C6 heterocycloalkyl may each independently be C2, C3, C4, C5 or C6 heterocycloalkyl, wherein a heteroatom therein includes O, N, S or P, etc. For example, the C2 to C6 heterocycloalkyl includes, but is not limited to, a tetrahydrofuran ring, a tetrahydropyrrole ring (pyrrolidine ring), a piperidine ring, etc.

The C2 to C6 alkenyl may each independently be C2, C3, C4, C5 or C6 alkene, for example, including, but not limited to, vinyl, propenyl, allyl or 1-butenyl, etc.

The C2 to C6 alkynyl may each independently be C2, C3, C4, C5 or C6 alkyne, for example, including, but not limited to, ethynyl, propynyl, propargyl, 1-butynyl or 2-butynyl, etc.

The C2 to C10 alkenyl may each independently be C2, C3, C4, C5, C6, C7, C8, C9 or C10 alkene.

The C2 to C10 alkynyl may each independently be C2, C3, C4, C5, C6, C7, C8, C9 or C10 alkyne.

Preferably, the amide compound has a structure represented by Formula IA:

Formula IA

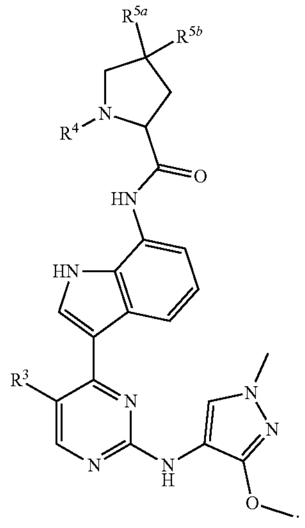

In Formula IA, $R^3$ and $R^4$ are each independently defined within the same ranges as in Formula I.

In Formula IA, $R^{5a}$ and $R^{5b}$ are each independently selected from H, F, cyano, C1 to C6 linear or branched alkyl, C3 to C6 cycloalkyl or $OR^{a5}$; $R^{5a}$ and $R^{5b}$ are not joined to each other or are joined by a chemical bond to form a 3- to 6-membered carbocycle or heterocarbocycle.

Preferably, $R^3$ is selected from H, halogen or C1 to C6 linear or branched alkyl.

Preferably, $R^4$ is selected from $SO_2R^{a2}$ ( 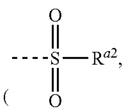

wherein the dashed line represents a linkage site of the group) or unsubstituted or $R^{4a}$-substituted C2 to C10 heterocycloalkyl.

In the above group, the C2 to C10 heterocycloalkyl, for example, includes, but is not limited to,

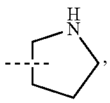, 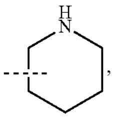, 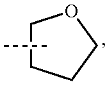,

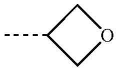 or 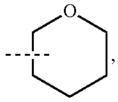, etc.; wherein the dashed line represents a linkage site of the group.

Preferably, $R^{a2}$ is selected from C1 to C6 linear or branched alkyl.

Preferably, $R^{a5}$ is selected from C1 to C6 linear or branched alkyl, further preferably methyl or ethyl.

Preferably, the amide compound has a structure represented by Formula IB:

Formula IB

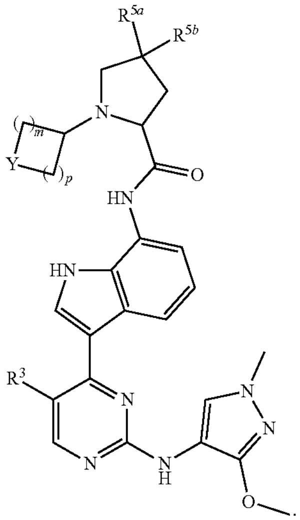

In Formula IB, $R^3$, $R^{5a}$ and $R^{5b}$ are each independently defined within the same ranges as in Formula IA.

In Formula IB, Y is $NR^7$ or O.

$R^7$ is selected from H, C1 to C6 linear or branched alkyl, C3 to C6 cycloalkyl or C2 to C6 heterocycloalkyl; wherein the linear or branched alkyl, the cycloalkyl or the heterocycloalkyl is unsubstituted or substituted with 1 to 5 (e.g., 1, 2, 3, 4 or 5) $R^{7a}$.

$R^{7a}$ is selected from D, halogen, cyano, C1 to C6 (e.g., C1, C2, C3, C4, C5 or C6) linear or branched alkyl, C3 to C6 cycloalkyl, C2 to C6 heterocycloalkyl, hydroxyl or C1 to C6 linear or branched alkoxy; wherein the linear or branched alkyl, the cycloalkyl or the heterocycloalkyl is unsubstituted or substituted with 1 to 5 (e.g., 1, 2, 3, 4 or 5) $R^{7b}$.

$R^{7b}$ is selected from D, halogen, cyano, hydroxyl or C1 to C6 linear or branched alkoxy.

m is 1 or 2, and p is an integer selected from 1 to 3, for example, may be 1, 2 or 3.

Preferably, $R^3$ is selected from H, halogen or methyl.

Preferably, $R^{5a}$ and $R^{5b}$ are each independently selected from H, F, methoxy or ethoxy.

Preferably, $R^7$ is H or methyl.

Preferably, p is 2.

Preferably, the amide compound includes any one or a combination of at least two of the following compounds:

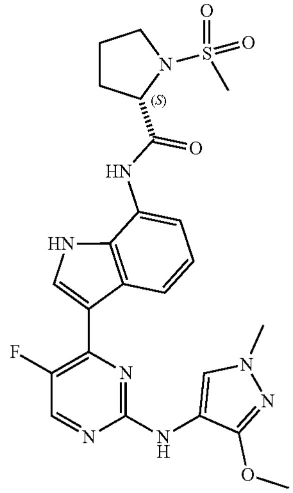

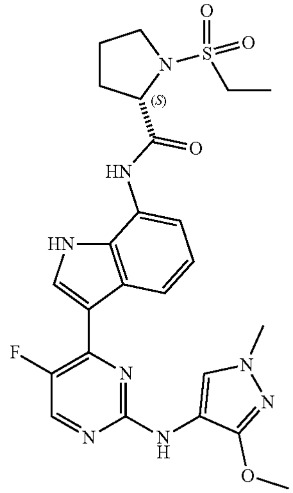

-continued
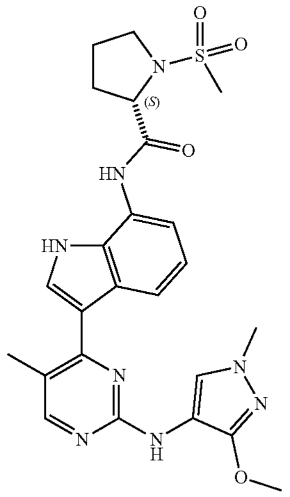
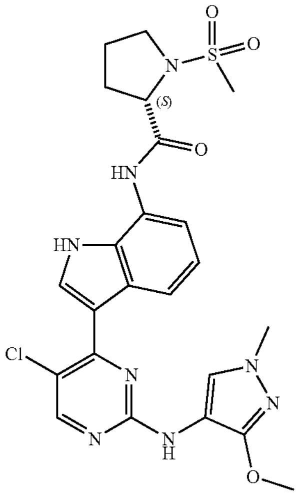
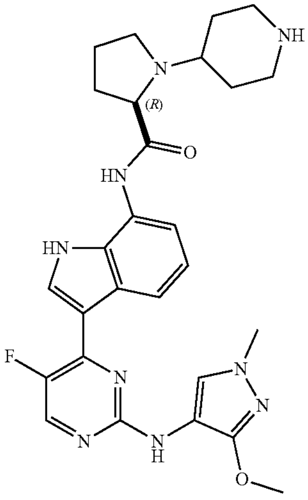
-continued
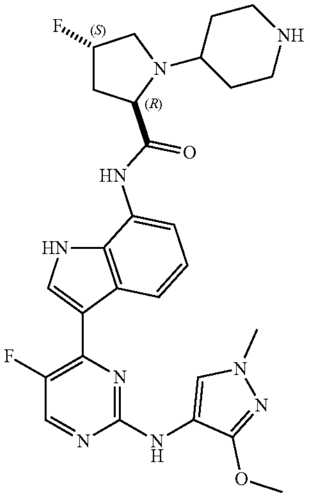
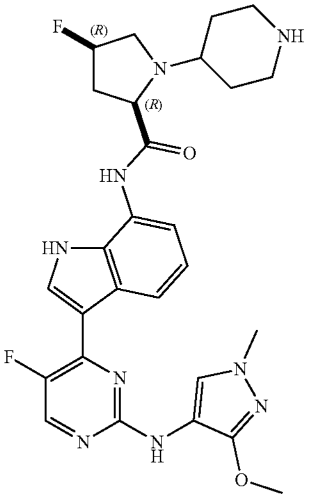
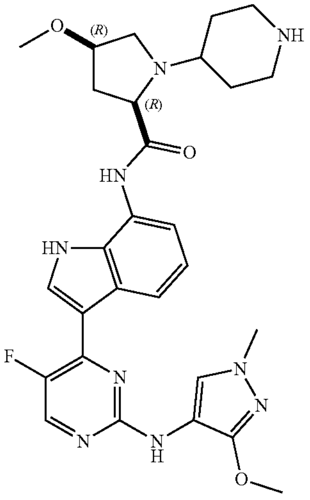

-continued
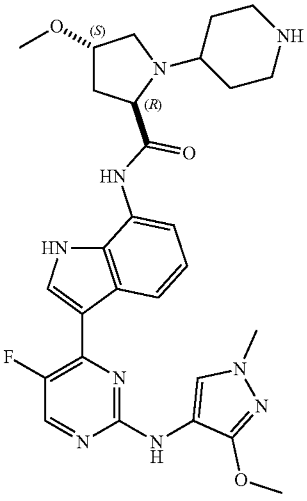
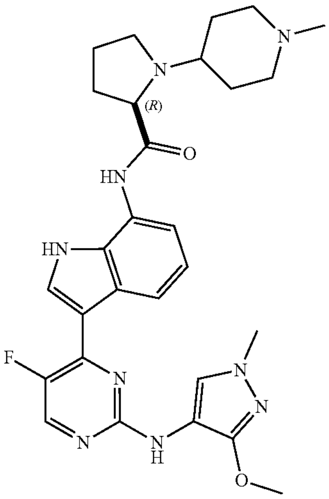
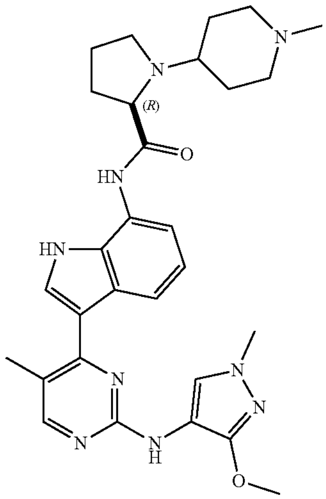
-continued
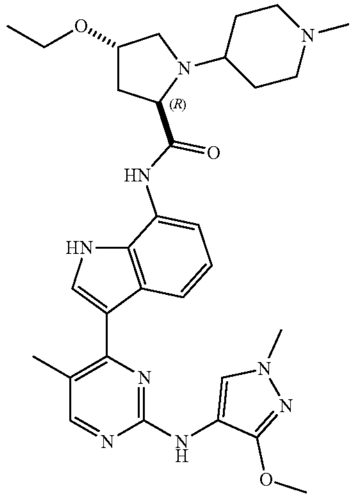
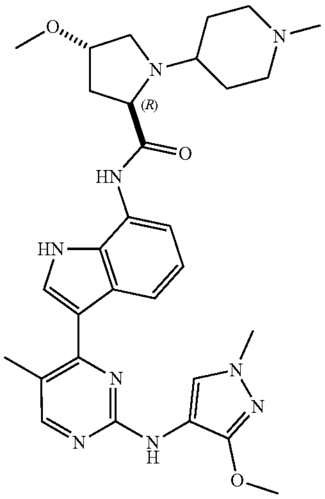
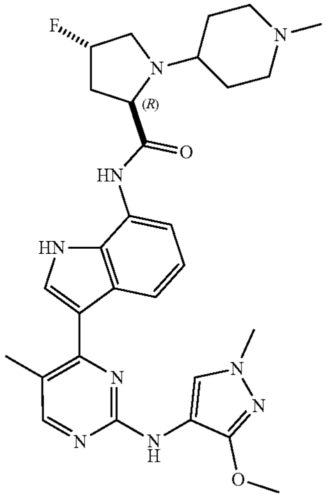

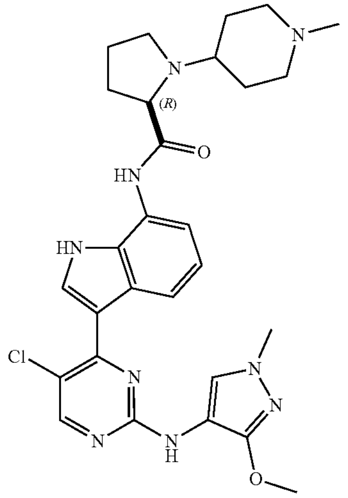
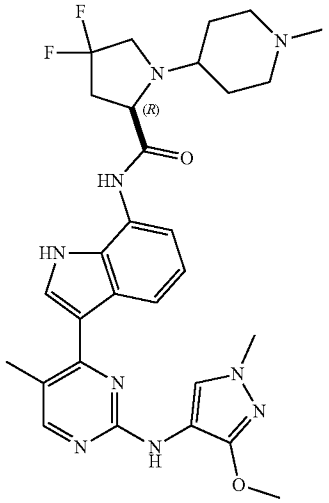
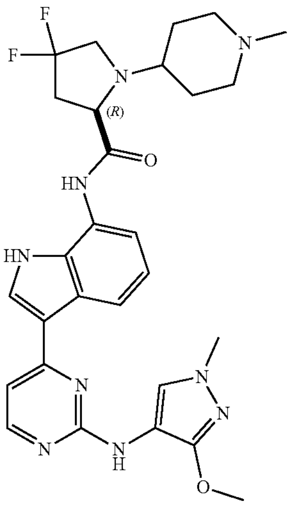
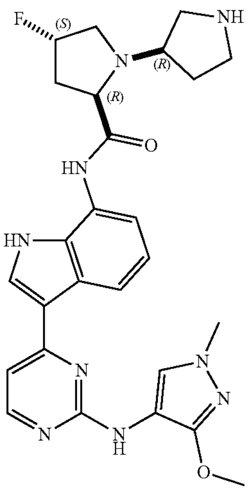
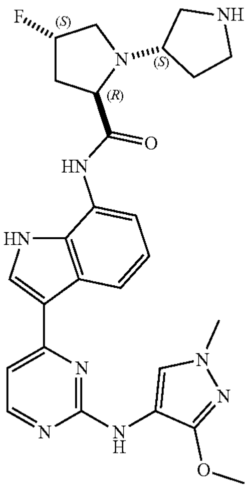
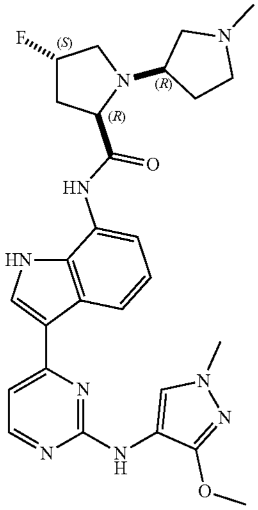

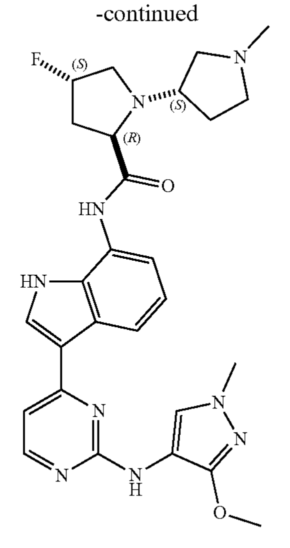
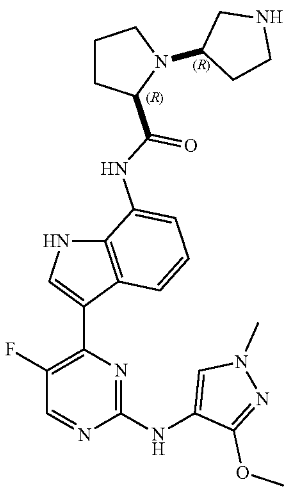
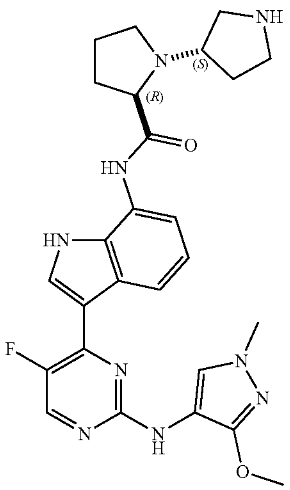
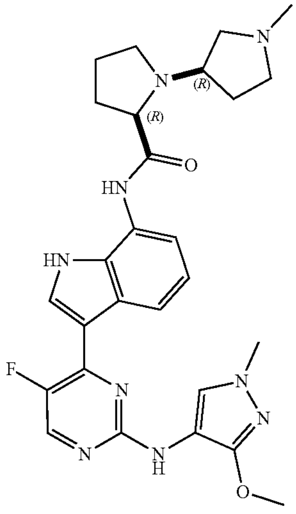
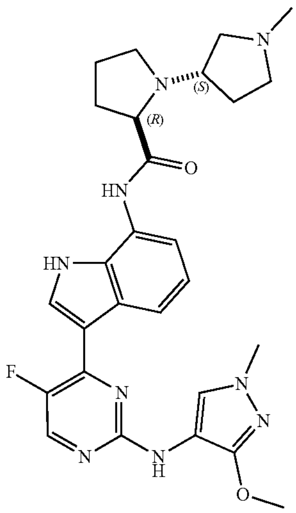
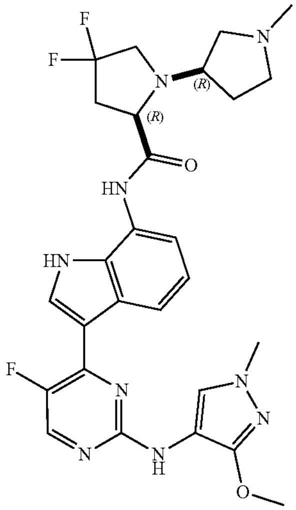

-continued
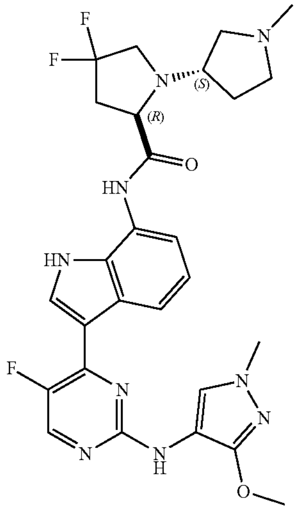
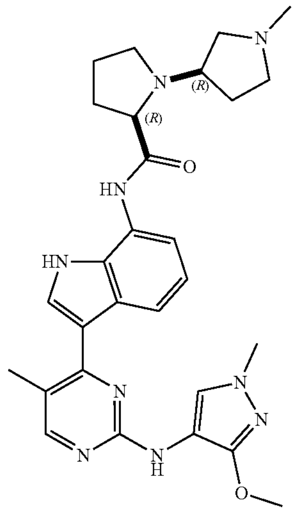
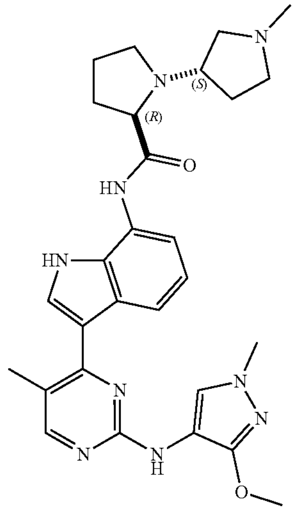
-continued
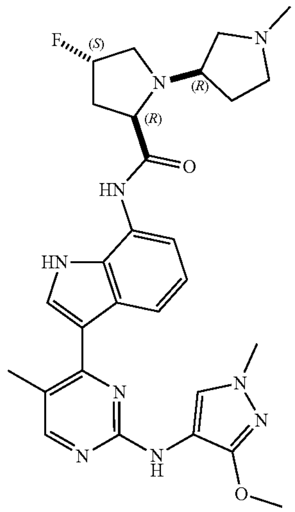
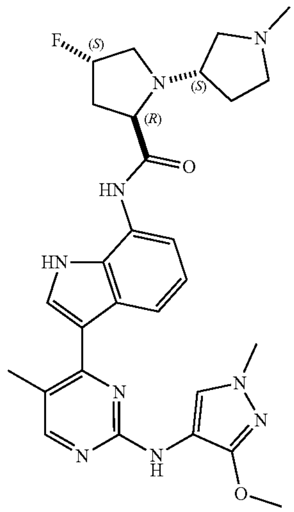
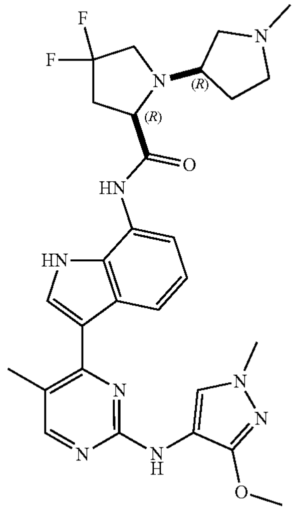

-continued
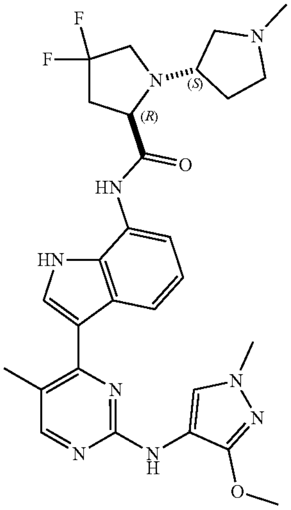
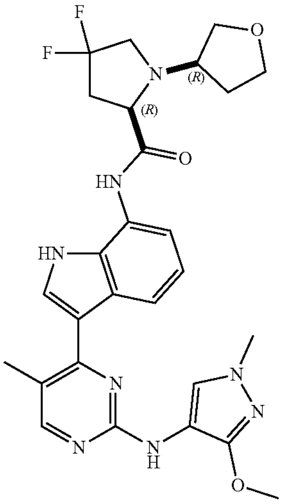
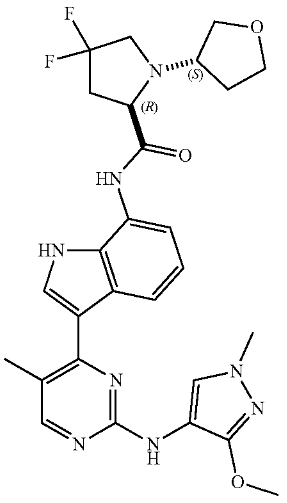
-continued
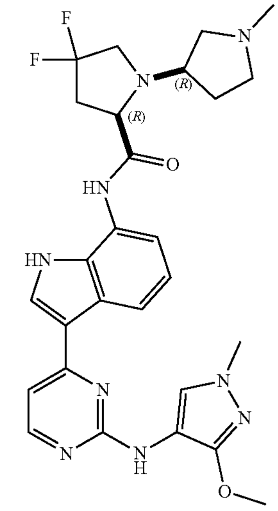
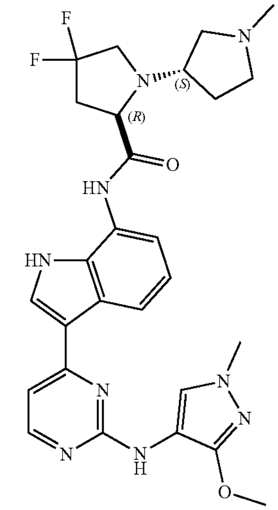
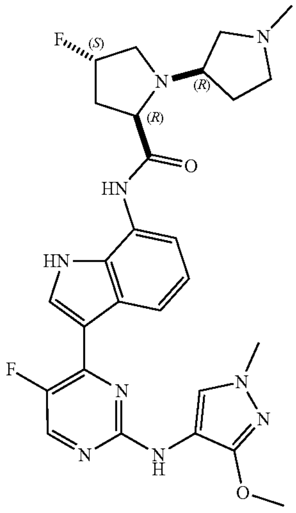

-continued

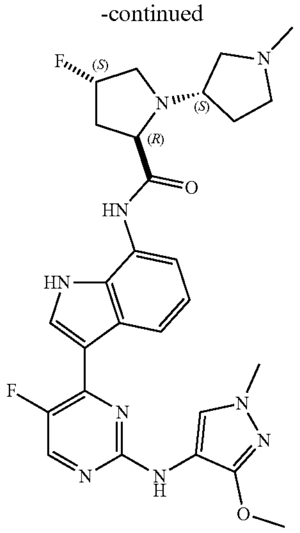

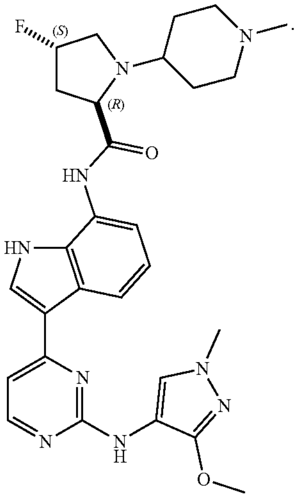

In a second aspect, the present application provides a stereoisomer, geometric isomer, tautomer or pharmaceutically acceptable salt of the amide compound in the first aspect.

In a third aspect, the present application provides a pharmaceutical composition including an active ingredient and at least one pharmaceutical carrier or excipient; wherein the active ingredient includes any one or a combination of at least two of the amide compound described in the first aspect and the stereoisomer, geometric isomer, tautomer or pharmaceutically acceptable salt described in the second aspect.

In a fourth aspect, the present application provides a use of the amide compound described in the first aspect, the stereoisomer, geometric isomer, tautomer or pharmaceutically acceptable salt described in the second aspect or the pharmaceutical composition described in the third aspect for preparing a medicament for inhibiting JAK.

Preferably, the JAK is JAK1.

In a fifth aspect, the present application provides a use of the amide compound described in the first aspect, the stereoisomer, geometric isomer, tautomer or pharmaceutically acceptable salt described in the second aspect, or the pharmaceutical composition described in the third aspect for preparing a medicament for treating a disease mediated by JAK.

The disease includes autoimmune diseases, inflammatory diseases, pain disorders, respiratory diseases, airway diseases, lung diseases, lung inflammation and injury, pulmonary hypertension, gastrointestinal diseases, allergic diseases, infectious diseases, trauma disorders and tissue injuries, fibrotic diseases, eye diseases, joint diseases, muscle diseases, bone diseases, skin diseases, kidney diseases, hematopoietic diseases, liver diseases, oral diseases, metabolic diseases, heart diseases, vascular diseases, neuroinflammatory diseases, neurodegenerative diseases, sepsis, genetic diseases or cancer.

Preferably, the disease includes an inflammation, an autoimmune disease or cancer.

Preferably, the inflammation or the autoimmune disease includes systemic lupus erythematosus, lupus nephritis, arthritis, psoriasis, Crohn's disease, ulcerative colitis, atopic dermatitis, gout, alopecia totalis, vitiligo, hidradenitis suppurativa, type I diabetes, chronic kidney disease, acute kidney injury, chronic obstructive pulmonary disease, asthma, bronchitis or graft-versus-host disease.

Preferably, the cancer includes breast cancer, lung cancer, prostate cancer, cholangiocarcinoma, bone cancer, bladder cancer, head and neck cancer, kidney cancer, liver cancer, gastrointestinal tissue cancer, esophageal cancer, ovarian cancer, pancreatic cancer, skin cancer, testicular cancer, thyroid cancer, uterine cancer, cervical cancer, vaginal cancer, leukemia, myelofibrosis, multiple myeloma or lymphoma.

Compared with the prior art, the present application has the beneficial effects described below.

The present application provides an amide compound having a new chemical structure. The amide compound has significant JAK inhibitory activity, especially JAK1 inhibitory activity. The JAK1 inhibitory activity of the amide compound is higher than the JAK2 inhibitory activity of the amide compound so that the amide compound can be used as a highly selective JAK1 inhibitor. The amide compound of the present application can be used for preparing a medicament for treating a disease mediated by JAK1, has a good therapeutic effect on a condition such as an inflammation, an autoimmune disease or cancer mediated by JAK1, and has a wide application prospect.

DETAILED DESCRIPTION

Technical solutions of the present application are further described below through embodiments.

Those skilled in the art are to understand that the examples described herein are used for a better understanding of the present application and are not to be construed as specific limitations to the present application.

The term "halo" or "halogen" in the present application includes fluorine, chlorine, bromine and iodine.

The term "linear or branched alkyl" refers to a linear or branched saturated hydrocarbon group. Examples of alkyl groups include methyl (Me), ethyl (Et), propyl (e.g., n-propyl and isopropyl), butyl (e.g., n-butyl, isobutyl and t-butyl), pentyl (e.g., n-pentyl, isopentyl and neopentyl), hexyl (e.g., n-hexyl, 2-hexyl, 3-hexyl, 2-methylpentyl, 3-methylpentyl, 2,2-dimethylbutyl and 3-ethylpentyl-1), heptyl (e.g., n-heptyl, 2-heptyl, 3-heptyl, 4-heptyl, 2-methylhexyl, 3-methylhexyl, 2,2-dimethylpentyl, 3,3-dimethylpentyl and 3-ethylpentyl-1), octyl (e.g., 1-octyl, 2-octyl and 2-ethylhexyl), nonyl (e.g., 1-nonyl), decyl (e.g., n-decyl) and similar groups. The linear or branched alkyl is further preferably linear or branched alkyl having 1, 2, 3, 4, 5 or 6 carbon atoms. Unless defined to the contrary, all groups in the present application are defined as defined herein.

The term "haloalkyl" refers to an alkyl group having one or more halogen substituents. The alkyl group and the halo or halogen are defined as above. Examples of haloalkyl groups include $CH_2F$, $CHF_2$, $CF_3$, $C_2F_5$, $CCl_3$ and similar groups.

The term "alkenyl" refers to a hydrocarbon group having one or more C═C double bonds. Examples of alkenyl groups include vinyl, propenyl, allyl, 1-butenyl, 2-butenyl, 1,3-butadienyl, 1-pentenyl, 2-pentenyl, 1,3-pentadienyl, 1-hexenyl, 2-hexenyl and similar groups.

The term "alkynyl" refers to a hydrocarbon group having one or more C≡C triple bonds. Examples of alkynyl groups include ethynyl, propynyl, propargyl, 1-butynyl, 2-butynyl, 1-pentynyl, 2-pentynyl, 1-hexynyl, 2-hexynyl and similar groups.

The term "cycloalkyl" refers to a non-aromatic carbocycle and includes cyclized alkyl, cyclized alkenyl and cyclized alkynyl. Cycloalkyl may be a monocyclic or polycyclic (e.g., with 2, 3 or 4 fused rings) ring system, including spirocyclic rings. In some embodiments, cycloalkyl may have 3, 4, 5, 6, 7, 8, 9 or 10 carbon atoms. Cycloalkyl may further have 0, 1, 2 or 3 C═C double bonds and/or 0, 1 or 2 C≡C triple bonds. Also included in the definition of cycloalkyl are moieties having one or more aromatic rings fused to (for example, having a common bond with) a cycloalkyl ring, such as benzo derivatives of pentane, pentene, hexane and hexene and similar compounds. A cycloalkyl group having one or more fused aromatic rings may be attached through the aromatic part or the non-aromatic part. Examples of cycloalkyl groups include cyclopropyl, cyclobutyl, cyclopentyl, cyclohexyl, cycloheptyl, cyclopentenyl, cyclohexenyl, cyclohexadienyl, cycloheptenyl, cycloheptadienyl, adamantyl, dihydroindenyl, tetrahydronaphthyl and similar groups.

The term "heterocycloalkyl" refers to a non-aromatic heterocycle in which one or more atoms forming the ring are heteroatoms such as O, N, P or S. Heterocycloalkyl groups may include a monocyclic or polycyclic (for example, with 2, 3 or 4 fused rings) ring system and spirocyclic rings. Examples of preferred "heterocycloalkyl" groups include, but are not limited to, aziridinyl, azetidinyl, tetrahydrofuranyl, tetrahydrothienyl, tetrahydropyranyl, pyrrolidinyl, oxazolidinyl, thiazolidinyl, imidazolidinyl, isoxazolidinyl, isothiazolidinyl, pyrazolidinyl, morpholinyl, thiomorpholinyl, piperazinyl, piperidinyl and similar groups. Also included in the definition of heterocycloalkyl are moieties having one or more aromatic rings fused to (for example, having a common bond with) a non-aromatic heterocycloalkyl ring, such as 2,3-dihydrobenzofuranyl, 1,3-benzodioxolenyl, benzo-1,4-dioxanyl, phthalimidyl, naphthalimidyl and similar groups. A heterocycloalkyl group having one or more fused aromatic rings may be attached through the aromatic part or the non-aromatic part.

The term "amide compound", as used herein, is meant to include all stereoisomers, geometric isomers, tautomers and isotopes.

The amide compound of the present application may be asymmetric, for example, have one or more stereocenters. Unless otherwise defined, all stereoisomers may be enantiomers and diastereomers. The amide compound of the present application that contains asymmetrically substituted carbon atoms may be separated into an optically pure form or a racemic form. The optically pure form may be prepared through resolution of a racemate or by using a chiral synthon or a chiral reagent.

The amide compound of the present application may also include tautomers. The tautomers are produced by exchanging a single bond with an adjacent double bond together with the migration of a proton.

The amide compound of the present application may also include all isotopic forms of atoms present in intermediates or final compounds. The isotopes include atoms that have the same atomic number but different masses. For example, the isotopes of hydrogen include deuterium and tritium.

The present application also includes a pharmaceutically acceptable salt of the amide compound. The "pharmaceutically acceptable salt" refers to a derivative of a compound modified through the conversion of a parent compound into its salt form through the present base part or a compound modified through the conversion of a parent compound into its salt form through the present acid part. Examples of pharmaceutically acceptable salts include, but are not limited to, salts of inorganic or organic acids of basic groups (e.g., ammonia) or salts of inorganic or organic bases of acid groups (e.g., carboxylic acid). The pharmaceutically acceptable salt of the present application may be synthesized by reacting the free base forms of the parent compounds represented by Formulas I, IA and IB with 1 to 4 equivalents of an appropriate acid in a solvent system. Appropriate salts are listed in Remington's Pharmaceutical Sciences, 17th ed., Mack Publishing Company, Easton Pa., 1985, 1418 and Journal of Pharmaceutical Science, 66, 2, 1977.

The amide compound and the pharmaceutically acceptable salt thereof in the present application further include solvate forms or hydrate forms. Generally speaking, the solvate forms or the hydrate forms are equivalent to non-solvate forms or non-hydrate forms, both of which are included in the scope of the present application. Some amide compounds of the present application may exist in a polycrystalline form or an amorphous form. In general, all physical forms of the compound are included in the scope of the present application.

The present application further includes a prodrug of the amide compound. The prodrug is a pharmacological substance (that is, a drug) derived from a parent drug. Once administered, the prodrug is metabolized in a body into the parent drug. The prodrug may be prepared by substituting one or more functional groups present in the compound. The preparation and use of the prodrug may be found in "Prodrugs as Novel Delivery Systems", T. Higuchi and V. Stella, Vol. 14 of the A.C.S. Symposium Series and Bioreversible Carriers in Drug Design, ed. Edward B. Roche, American Pharmaceutical Association and Pergamon Press, 1987.

In a specific embodiment, the amide compound includes the following compounds:

(S)—N-(3-(5-fluoro-2-((3-methoxy-1-methyl-1H-pyrazol-4-yl)amino)pyrimidin-4-yl)-1H-indol-7-yl)-1-(methanesulfonyl)pyrrolidine-2-carboxamide;

(S)—N-(3-(5-fluoro-2-((3-methoxy-1-methyl-1H-pyrazol-4-yl)amino)pyrimidin-4-yl)-1H-indol-7-yl)-1-(ethanesulfonyl)pyrrolidine-2-carboxamide;

(S)—N-(3-(2-((3-methoxy-1-methyl-1H-pyrazol-4-yl)amino)-5-methylpyrimidin-4-yl)-1H-indol-7-yl)-1-(methanesulfonyl)pyrrolidine-2-carboxamide;

(S)—N-(3-(5-chloro-2-((3-methoxy-1-methyl-1H-pyrazol-4-yl)amino)pyrimidin-4-yl)-1H-indol-7-yl)-1-(methanesulfonyl)pyrrolidine-2-carboxamide;

(R)—N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide;

(2R,4S)-4-fluoro-N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide;

(2R,4R)-4-fluoro-N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide;

(2R,4R)—N-(3-(5-fluoro-2-((3-methoxy-1-methyl-1H-pyrazol-4-yl)amino)pyrimidin-4-yl)-1H-indol-7-yl)-4-methoxy)-1-(piperidin-4-yl)pyrrolidine-2-carboxamide;

(2R,4S)—N-(3-(5-fluoro-2-((3-methoxy-1-methyl-1H-pyrazol-4-yl)amino)pyrimidin-4-yl)-1H-indol-7-yl)-4-methoxy-1-(piperidin-4-yl)pyrrolidine-2-carboxamide;

(R)—N-(3-(5-fluoro-2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide;

(R)—N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide;

(2R,4S)-4-ethoxy-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide;

(2R,4S)-4-methoxy-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide;

(2R,4S)-4-fluoro-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide;

(R)—N-(3-(5-chloro-2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide;

(R)-4,4-difluoro-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide;

(R)-4,4-difluoro-N-(3-(2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide;

(2R,3'R,4S)-4-fluoro-N-(3-(2-((3-methoxy-1-methyl-1H-pyrazol-4-yl)amino)pyrimidin-4-yl)-1H-indol-7-yl)-[1,3'-bipyrrolidine]-2-carboxamide;

(2R,3'S,4S)-4-fluoro-N-(3-(2-((3-methoxy-1-methyl-1H-pyrazol-4-yl)amino)pyrimidin-4-yl)-1H-indol-7-yl)-[1,3'-bipyrrolidine]-2-carboxamide;

(2R,3'R,4S)-4-fluoro-N-(3(2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'S,4S)-4-fluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'R)—N-(3-(5-fluoro-2-((3-methoxy-1-methyl-1H-pyrazol-4-yl)amino)pyrimidin-4-yl)-1H-indol-7-yl)-[1,3'-bipyrrolidine]-2-carboxamide;

(2R,3'S)—N-(3-(5-fluoro-2-((3-methoxy-1-methyl-1H-pyrazol-4-yl)amino)pyrimidin-4-yl)-1H-indol-7-yl)-[1,3'-bipyrrolidine]-2-carboxamide;

(2R,3'R)—N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'S)—N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'R)-4,4-difluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'S)-4,4-difluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'R)—N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(2R,3'S)—N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(2R,3'R,4S)-4-fluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(2R,3'S,4S)-4-fluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(2R,3'R)-4,4-difluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(2R,3'S)-4,4-difluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide;

(R)-4,4-difluoro-N-(3-(2-((3-methoxy-1-methyl-1H-pyrazol-4-yl)amino)-5-methylpyrimidin-4-yl)-1H-indol-7-yl)-1-((R)-tetrahydrofuran-3-yl)pyrrolidine-2-carboxamide;

(R)-4,4-difluoro-N-(3-(2-((3-methoxy-1-methyl-1H-pyrazol-4-yl)amino)-5-methylpyrimidin-4-yl)-1H-indol-7-yl)-1-((S)-tetrahydrofuran-3-yl)pyrrolidine-2-carboxamide;

(2R,3'R)-4,4-difluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'S)-4,4-difluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'R,4S)-4-fluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide;

(2R,3'S,4S)-4-fluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide; and (2R,4S)-4-fluoro-N-(3-(2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide.

The present application provides a pharmaceutical composition consisting of the amide compound or a N-oxide derivative thereof, an individual isomer thereof or a mixture of isomers thereof, a pharmaceutically acceptable salt and a pharmaceutically acceptable carrier or excipient. The pharmaceutical composition of the present application may be administered through oral administration, parenteral administration (injection administration), spray inhalation, topical administration, rectal administration, nasal administration, vaginal administration, intraperitoneal administration or via an implanted reservoir.

In another aspect of the present application, the amide compound and a pharmaceutically acceptable salt may be used in combination with one or more other medicaments. The amide compound of the present application and the medicaments used in combination with the amide compound may achieve an additive or synergistic effect when they are used in combination. The medicaments used in combination with the amide compound may be a small molecule medicament, a monoclonal antibody medicament, a fusion protein medicament or an anti-sense DNA medicament.

In a specific embodiment, the amide compound may be obtained through the following preparation route 1 or preparation route 2:
Preparation route 1
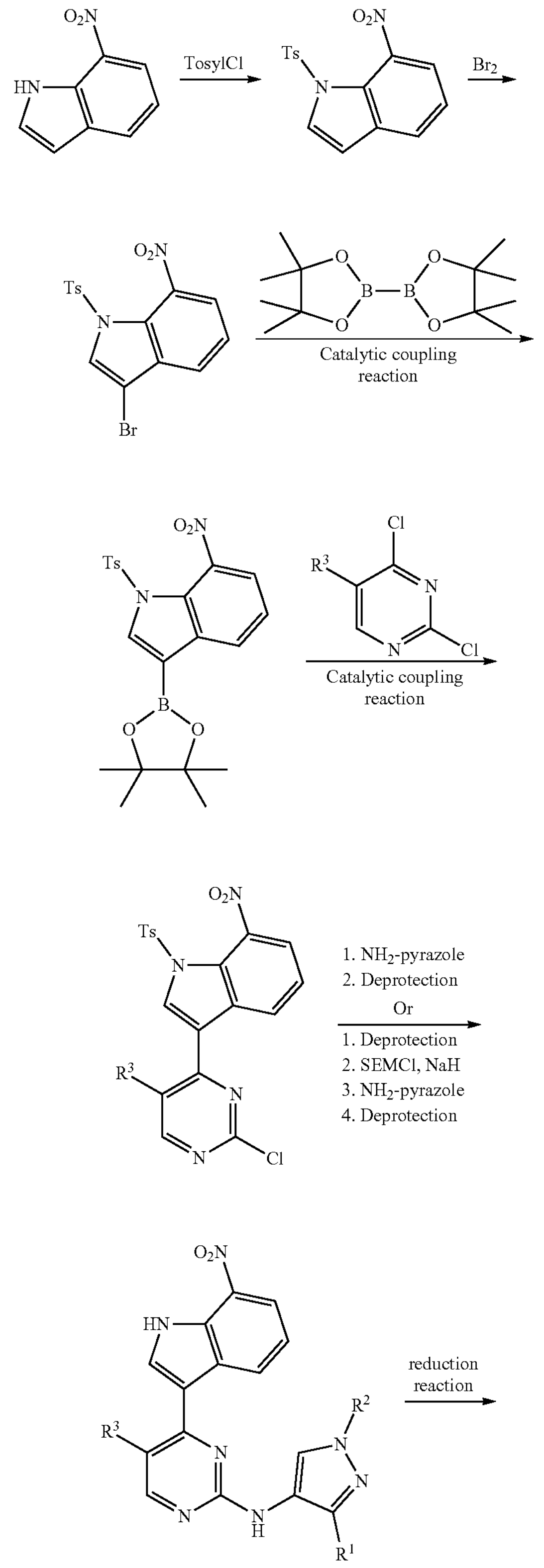
-continued
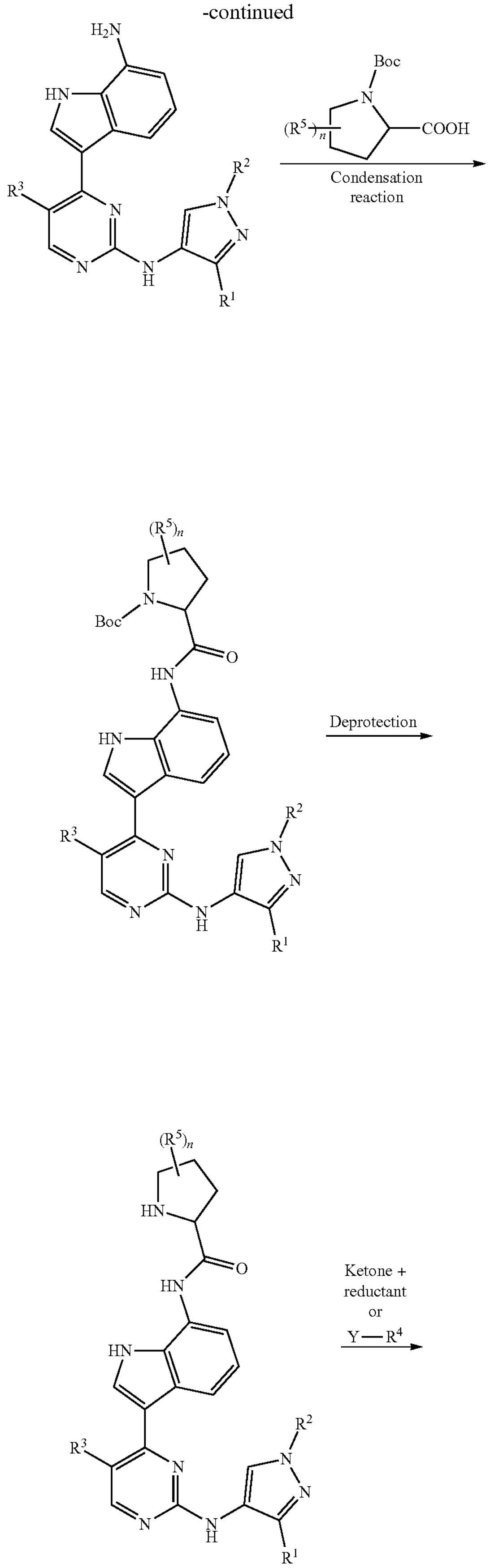

-continued

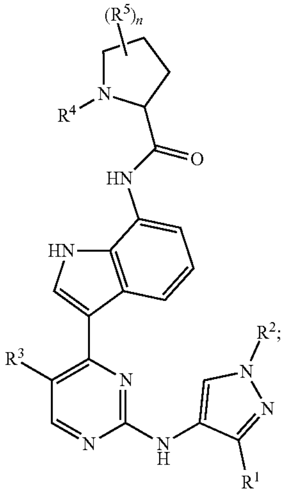

Preparation route 2

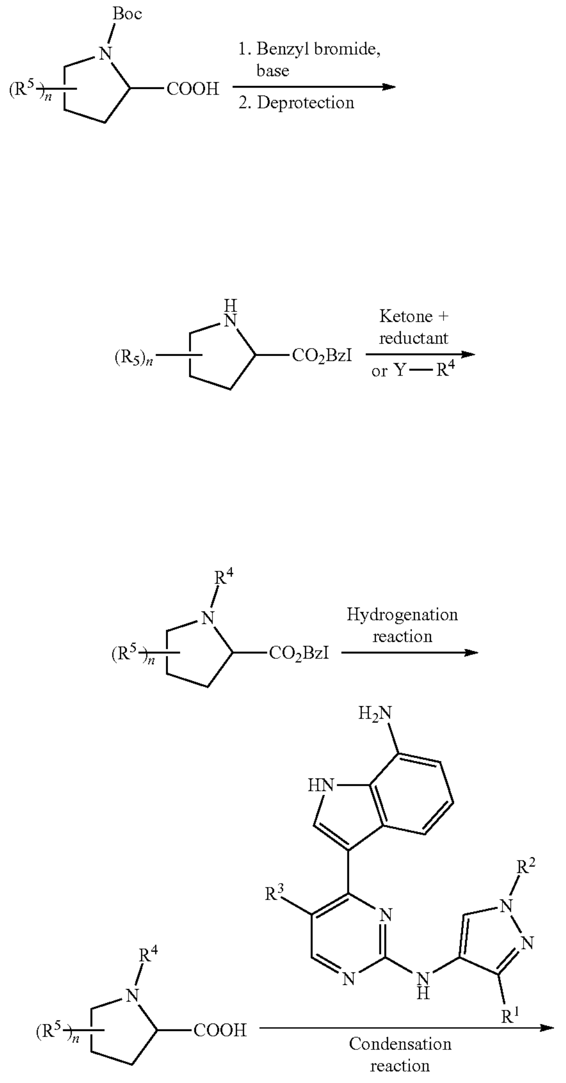

-continued

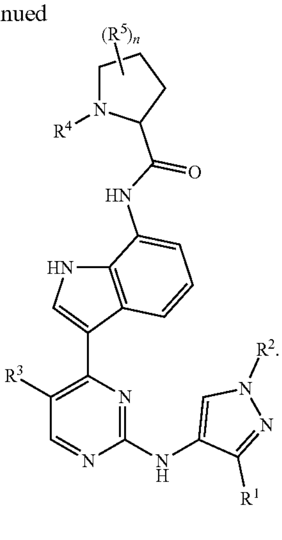

In the above preparation routes, $NH_2$-pyrazole represents

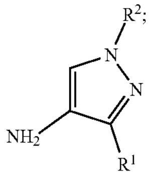

$R^1$, $R^2$, $R^3$, $R^4$, $R^5$ and n are each independently defined within the same ranges as in Formula I; Ts, Boc and SEM are amino protecting groups; Bzl represents benzyl and is a carboxylic acid protecting group; and Y is a leaving group such as Cl. Specific synthesis methods are described in detail in examples.

Preparation Example 1

Intermediate 1 (3-methoxy-1-methyl-4-amino-1H-pyrazole) was prepared by the specific steps described below.

(1) Synthesis of methyl 3-methoxy-1H-pyrazole-4-carboxylate

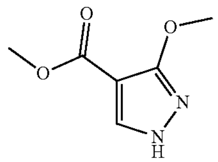

In a 1 L round-bottom flask, dimethyl 2-(methoxymethylene)maleate (25.0 g, 143.7 mmol), hydrazine hydrochloride (20.0 g, 292.0 mmol) and ethanol (EtOH, 500 mL) were added and then heated to reflux for 16 h. After the reaction was completed, the solution was concentrated under reduced pressure to remove ethanol, the residue was dispersed in ethyl acetate (EtOAc, 500 mL), stirred for 30 min and filtered, and the filter residue was washed with EtOAc. The filtrate was concentrated to remove the solvent to obtain the product (10.0 g) with a yield of 45%. LCMS (ESI): m/z=157 $(M+H)^+$.

(2) Synthesis of 3-methoxy-1H-pyrazole

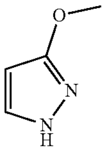

In a 100 mL round-bottom flask, methyl 3-methoxy-1H-pyrazole-4-carboxylate (10.0 g, 64.1 mmol) was dissolved in hydrochloric acid (6 M, 30 mL) and then heated to 90° C. to react for 16 h. After the reaction was completed, the solution was diluted with water and neutralized with $NaHCO_3$ solids. The resulting aqueous phase was extracted with EtOAc and the ester phase was dried over anhydrous $Na_2SO_4$, filtered and concentrated to obtain the product (6.0 g) with a yield of 95%. LCMS (ESI): m/z=99 $(M+H)^+$.

(3) Synthesis of 3-methoxy-4-nitro-1H-pyrazole

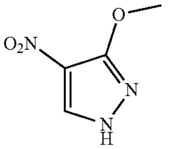

In an ice-water bath, 3-methoxy-1H-pyrazole (6.0 g, 61.2 mmol) was dissolved in concentrated sulfuric acid (36 mL), potassium nitrate solids (6.2 g, 61.2 mmol) were added portionwise, and they were reacted for 30 min with the temperature maintained. After the reaction was completed, the reaction solution was poured into ice water and neutralized with $NaHCO_3$ solids. The aqueous phase was extracted with EtOAc and the ester phase was dried over anhydrous $Na_2SO_4$, filtered and concentrated to obtain the product (4.2 g) with a yield of 48%. LCMS (ESI): m/z=144 $(M+H)^+$.

(4) Synthesis of 3-methoxy-1-methyl-4-nitro-1H-pyrazole

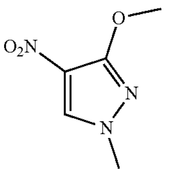

In a 100 mL round-bottom flask, 3-methoxy-4-nitro-1H-pyrazole (4.2 g, 29.4 mmol) was dissolved in dimethylformamide (DMF, 40 mL), added with $K_2CO_3$ (6.1 g, 44.1 mmol), reacted for 30 min at room temperature, added with iodomethane (12.5 g, 88.2 mmol) and reacted for 16 h at room temperature. After the reaction was completed, the reaction solution was diluted with water and extracted with EtOAc and the ester phase was dried over anhydrous $Na_2SO_4$, filtered and concentrated to obtain the product (3.8 g) with a yield of 82%. LCMS (ESI): m/z=158 $(M+H)^+$.

(5) Synthesis of 3-methoxy-1-methyl-4-amino-1H-pyrazole

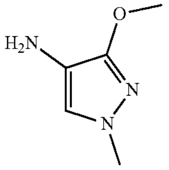

Palladium carbon (10% Pd/C, 55% water, 1.0 g) and hydrazine hydrate (8 mL) were added to a solution of 3-methoxy-1-methyl-4-nitro-1H-pyrazole (3.8 g, 24.2 mmol) in EtOAc/EtOH (40 mL/10 mL) and reacted for 16 h at room temperature. After the reaction was completed, the solution was filtered and the filter residue was washed with EtOAc. The filtrates were combined and concentrated under reduced pressure. The resulting residue was dissolved in EtOAc and HCl/EtOAc was added dropwise with rapid stirring until the precipitate was completely separated. The solution was filtered and the filter residue was washed with EtOAc and acetonitrile (MeCN) to obtain a hydrochloric acid salt of the product (3.5 g) with a yield of 89%. LCMS (ESI): m/z=128$(M+H)^+$.

Preparation Example 2

Intermediate 2 (7-nitro-3-(4,4,5,5-tetramethyl-1,3,2-dioxaborolan-2-yl)-1-(4-methylbenzenesulfonyl)-1H-indole) was prepared by the specific steps described below.

(1) Synthesis of 7-nitro-1-(4-methylbenzenesulfonyl)-1H-indole

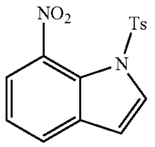 [SMILES: Cc1ccc(S(=O)(=O)n2ccc3cccc([N+](=O)[O-])c32)cc1]

In a 1000 mL round-bottom flask, 7-nitro-1H-indole (16.2 g, 100.0 mmol) and tetrabutylammonium bromide (3.2 g, 10.0 mmol) were dissolved in $CH_2Cl_2$ (300 mL) and cooled in an ice-water bath. An aqueous NaOH solution (10 M, 40 mL) was added dropwise to the above solution, reacted for 30 min with the temperature maintained and added with 4-methylbenzenesulfonyl chlorine (28.5 g, 150.0 mmol). The reaction system was naturally warmed to room temperature to react for 16 h. After the reaction was completed, the solution was diluted with $CH_2Cl_2$, and the organic phase was washed with water, a 10% aqueous $K_2CO_3$ solution, water, 1 M dilute hydrochloric acid and a saturated aqueous NaCl solution in sequence, dried over anhydrous $Na_2SO_4$, filtered and concentrated to obtain the product (30.0 g) with a yield of 95%. LCMS (ESI): m/z=317 $(M+H)^+$.

(2) Synthesis of 3-bromo-7-nitro-1-(4-methylbenzenesulfonyl)-1H-indole

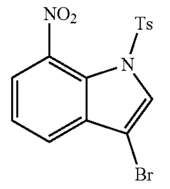 [SMILES: Cc1ccc(S(=O)(=O)n2cc(Br)c3cccc([N+](=O)[O-])c32)cc1]

In an ice-water bath, 7-nitro-1-(4-methylbenzenesulfonyl)-1H-indole (31.6 g, 100.0 mmol) was dissolved in $CH_2Cl_2/CCl_4$ (250 mL/250 mL), a solution of $Br_2$ (24.0 g, 150.0 mmol) in $CCl_4$ (100 mL) was slowly added dropwise, and after the addition, the solution was naturally warmed to room temperature to react for 16 h. After the reaction was completed, the solution was concentrated under reduced pressure to remove the solvent, added with EtOAc (500 mL), heated to reflux for 1 h, cooled to room temperature and filtered, and the filter residue was washed with EtOAc and dried to obtain a pale yellow solid (25 g) with a yield of 63%.

(3) Synthesis of 7-nitro-3-(4,4,5,5-tetramethyl-1,3,2-dioxaborolan-2-yl)-1-(4-methylbenzenesulfonyl)-1H-indole

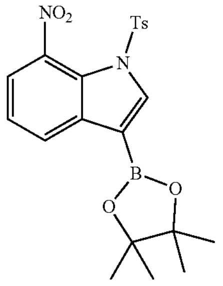 [SMILES: Cc1ccc(S(=O)(=O)n2cc(B3OC(C)(C)C(C)(C)O3)c3cccc([N+](=O)[O-])c32)cc1]

In a 500 mL round-bottom flask, 3-bromo-7-nitro-1-(4-methylbenzenesulfonyl)-1H-indole (10.0 g, 31.6 mmol), pinacol diborate (16.0 g, 63.2 mmol), a palladium catalyst $Pd(dppf)Cl_2$ (2.3 g, 3.2 mmol), potassium acetate (AcOK, 9.3 g, 94.8 mmol) and dioxane (300 mL) were added and heated to 100° C. to react for 16 h under $N_2$ protection. After the reaction was completed, the reaction solution was poured into water and extracted with EtOAc. The ester phase was dried over anhydrous $Na_2SO_4$, filtered, concentrated to 50 mL, added with 300 mL of petroleum ether, rapidly stirred for 1 min and filtered quickly. The filtrate was cooled in an ice-water bath to precipitate a solid and filtered. The filter residue was washed with petroleum ether and cold ethanol to obtain a pale yellow solid (7.5 g) with a yield of 54%. LCMS (ESI): m/z=443 $(M+H)^+$.

Preparation Example 3

Intermediate 3 (3-(2-((3-methoxy-1-methyl-1H-pyrazol-4-yl)amino)pyrimidin-4-yl)-1H-indol-7-amine) was prepared by the specific steps described below.

(1) Synthesis of 3-(2-chloropyrimidin-4-yl)-7-nitro-1-(4-methylbenzenesulfonyl)-1H-indole

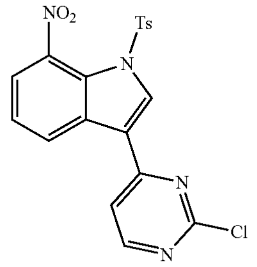 [SMILES: Cc1ccc(S(=O)(=O)n2cc(-c3ccnc(Cl)n3)c3cccc([N+](=O)[O-])c32)cc1]

In a 100 mL round-bottom flask, Intermediate 2 (2.0 g, 4.5 mmol), 2,4-dichloropyrimidine (666 mg, 4.5 mmol), $Pd(dppf)Cl_2$ (366 mg, 0.5 mmol), tetrabutylammonium fluoride (131 mg, 0.5 mmol), $Na_2CO_3$ (1.4 g, 13.5 mmol) and DMSO (30 mL) were added and reacted for 2 h in an oil bath preheated to 120° C. under $N_2$ protection. After the reaction was completed, the reaction solution was poured into water and extracted with EtOAc. The ester phase was dried over anhydrous $Na_2SO_4$, filtered and concentrated. The resulting residue was isolated and purified through silica gel column chromatography (mobile phase: a mixed solution of $CH_2Cl_2$ and methanol (MeOH) with a volume ratio of 20:1) to obtain the product (1.5 g) with a yield of 78%. LCMS (ESI): m/z=429 $(M+H)^+$.

(2) Synthesis of N-(3-methoxy-1-methyl-1H-pyrazol-4-yl)-4-(7-nitro-1H-indol-3-yl) pyrimidin-2-amine

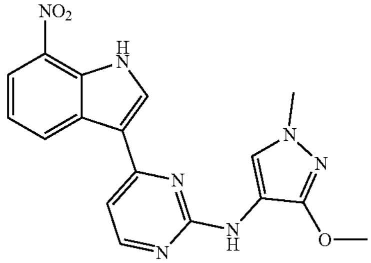 [SMILES: COc1nn(C)cc1Nc1nccc(-c2c[nH]c3c([N+](=O)[O-])cccc23)n1]

In a 100 mL round-bottom flask, 3-(2-chloropyrimidin-4-yl)-7-nitro-1-(4-methylbenzenesulfonyl)-1H-indole (1.5 g, 3.5 mmol), 3-methoxy-1-methyl-1H-pyrazol-4-amine hydrochloride (570 mg, 3.5 mmol), a palladium catalyst $Pd(dba)_2$ (230 mg, 0.4 mmol), binaphthyldiphenylphosphine (BINAP, 249 mg, 0.4 mmol), $Cs_2CO_3$ (4.5 g, 14.0 mmol) and dioxane (30 mL) were added and heated to 110° C. to react for 2 h under $N_2$ protection. The reaction system was cooled to room temperature, added with an aqueous NaOH solution (3 M, 10 mL) and reacted for 1 h at room temperature. After the reaction was completed, the reaction solution was poured into water and extracted with EtOAc. The ester phase was dried over anhydrous $Na_2SO_4$, filtered and concentrated. The resulting residue was isolated and purified through silica gel column chromatography (mobile phase: a mixed solution of $CH_2Cl_2$ and MeOH with a volume ratio of 10:1) to obtain the product (1.0 g) with a yield of 78%. LCMS (ESI): m/z=366 $(M+H)^+$.

(3) Synthesis of 3-(2-((3-methoxy-1-methyl-1H-pyrazol-4-yl)amino)pyrimidin-4-yl)-1H-indol-7-amine

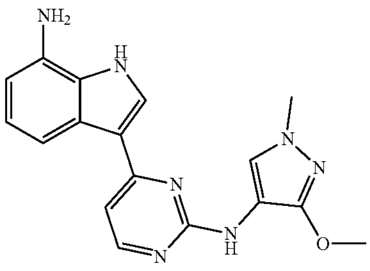

In an ice-water bath, N-(3-methoxy-1-methyl-1H-pyrazol-4-yl)-4-(7-nitro-1H-indol-3-yl) pyrimidin-2-amine (1.0 g, 2.7 mmol) was dissolved in EtOH (20 mL), added with acetic acid (AcOH, 1.6 g, 27 mmol) and zinc powder (864 mg, 13.5 mmol) and naturally warmed to room temperature to react for 1 h. After the reaction was completed, the reaction solution was poured into water and extracted with EtOAc. The ester phase was dried over anhydrous $Na_2SO_4$, filtered and concentrated to obtain the product (850 mg) with a yield of 94%. LCMS (ESI): m/z=336 $(M+H)^+$.

Intermediates 4 and 5 were synthesized according to the synthesis route of Intermediate 3 in Preparation Example 3. The specific structures and mass spectrometry information of the products are shown in Table 1.

(1) Synthesis of 3-(2-chloro-5-methylpyrimidin-4-yl)-7-nitro-1H-indole

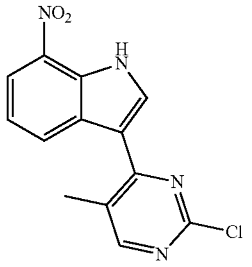

In a 100 mL round-bottom flask, Intermediate 2 (2.0 g, 4.5 mmol), 2,4-dichloro-5-methylpyrimidine (734 mg, 4.5 mmol), Pd(dppf)$Cl_2$ (366 mg, 0.5 mmol), tetrabutylammonium fluoride (131 mg, 0.5 mmol), $Na_2CO_3$ (1.4 g, 13.5 mmol) and DMSO (30 mL) were reacted for 2 h in an oil bath preheated to 120° C. under $N_2$ protection. The reaction system was cooled to room temperature, added with an aqueous NaOH solution (3 M, 10 mL) and reacted for 1 h at room temperature. After the reaction was completed, the reaction solution was poured into water and extracted with EtOAc. The ester phase was dried over anhydrous $Na_2SO_4$, filtered and concentrated. The resulting residue was isolated and purified through silica gel column chromatography (mobile phase: a mixed solution of $CH_2Cl_2$ and MeOH with a volume ratio of 10:1) to obtain the product (1.0 g) with a yield of 77%. LCMS (ESI): m/z=289 $(M+H)^+$.

TABLE 1

| Intermediate | Compound Structure | Compound Name | LCMS (ESI) |
|---|---|---|---|
| 4 | 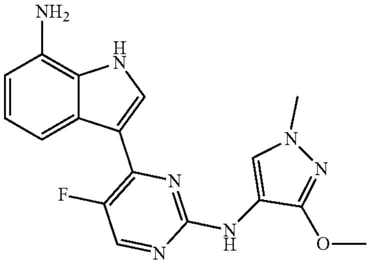 [SMILES: COc1nn(C)cc1Nc1ncc(F)c(-c2c[nH]c3c(N)cccc23)n1] | 3-(5-Fluoro-2-((3-methoxy-1-methyl-1H-pyrazol-4-yl)amino)pyrimidin-4-yl)-1H-indol-7-amine | 354 $(M + H)^+$ |
| 5 | 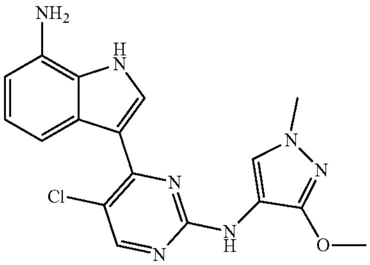 [SMILES: COc1nn(C)cc1Nc1ncc(Cl)c(-c2c[nH]c3c(N)cccc23)n1] | 3-(5-Chloro-2-((3-methoxy-1-methyl-1H-pyrazol-4-yl)amino)pyrimidin-4-yl)-1H-indol-7-amine | 370 $(M + H)^+$ |

Preparation Example 4

Intermediate 6 (3-(2((3-methoxy-1-methyl-1H-pyrazol-4-yl)amino)-5-methylpyrimidin-4-yl)-1H-indol-7-amine) was prepared by the specific steps described below.

(2) Synthesis of 3-(2-chloro-5-methylpyrimidin-4-yl)-7-nitro-1-((2-(trimethylsilyl)ethoxy) methyl)-1H-indole

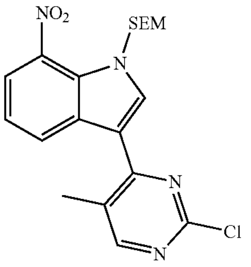 [SMILES: Cc1cnc(Cl)nc1-c1cn(COCC[Si](C)(C)C)c2c([N+](=O)[O-])cccc12]

In an ice-water bath, 3-(2-chloro-5-methylpyrimidin-4-yl)-7-nitro-1H-indole (2.0 g, 6.9 mmol) was dispersed in tetrahydrofuran (THF, 30 mL). NaH (556 mg, 60%, 13.9 mmol) was added to the above mixture and reacted for 30 min with the temperature maintained. 2-(Trimethylsilyl) ethoxymethyl chloride (SEMCl, 1.7 g, 10.4 mmol) was added dropwise and reacted for 1 h. After the reaction was completed, the reaction solution was carefully poured into ice water and extracted with EtOAc. The ester phase was dried over anhydrous $Na_2SO_4$, filtered and concentrated. The resulting residue was isolated and purified through silica gel column chromatography (mobile phase: a mixed solution of PE and EtOAc with a volume ratio of 5:1) to obtain the product (2.6 g) with a yield of 90%. LCMS (ESI): m/z=419 $(M+H)^+$.

(3) Synthesis of N-(3-methoxy-1-methyl-1H-pyrazol-4-yl)-5-methyl-4-(7-nitro-1-((2-(trimethylsilyl) ethoxy)methyl)-1H-indol-3-yl)pyrimidin-2-amine

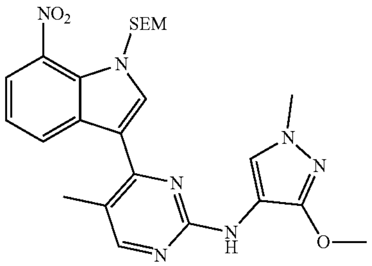 [SMILES: COc1nn(C)cc1Nc1ncc(C)c(-c2cn(COCC[Si](C)(C)C)c3c([N+](=O)[O-])cccc23)n1]

In a 100 mL round-bottom flask, 3-(2-chloro-5-methylpyrimidin-4-yl)-7-nitro-1-((2-(trimethylsilyl)ethoxy)methyl)-1H-indole (2.6 g, 6.2 mmol), 3-methoxy-1-methyl-1H-pyrazol-4-amine hydrochloride (1.0 g, 6.2 mmol), $Pd(dba)_2$ (345 mg, 0.6 mmol), BINAP (373 mg, 0.6 mmol), $Cs_2CO_3$ (6.0 g, 18.6 mmol) and dioxane (50 mL) were added and heated to 110° C. to react for 2 h under $N_2$ protection. After the reaction was completed, the reaction solution was poured into water and extracted with EtOAc. The ester phase was dried over anhydrous $Na_2SO_4$, filtered and concentrated. The resulting residue was isolated and purified through silica gel column chromatography (mobile phase: a mixed solution of PE and EtOAc with a volume ratio of 3:1) to obtain the product (2.3 g) with a yield of 73%. LCMS (ESI): m/z=510 $(M+H)^+$.

(4) Synthesis of N-(3-methoxy-1-methyl-1H-pyrazol-4-yl)-5-methyl-4-(7-nitro-1H-indol-3-yl) pyrimidin-2-amine

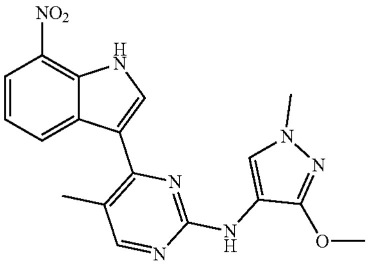 [SMILES: COc1nn(C)cc1Nc1ncc(C)c(-c2c[nH]c3c([N+](=O)[O-])cccc23)n1]

In an ice-water bath, N-(3-methoxy-1-methyl-1H-pyrazol-4-yl)-5-methyl-4-(7-nitro-1-((2-(trimethylsilyl)ethoxy) methyl)-1H-indol-3-yl)pyrimidin-2-amine (2.3 g, 4.5 mmol) was dissolved in $CH_2Cl_2$ (15 mL), added with trifluoroacetic acid (TFA, 15 mL) and naturally warmed to room temperature to react for 1 h. The solution was concentrated under reduced pressure to remove TFA. The residue was dissolved in MeOH (15 mL), cooled in an ice-water bath, added with ammonia (25%, 15 mL) and warmed to room temperature to react for 6 h. After the reaction was completed, the reaction solution was poured into water and extracted with EtOAc. The ester phase was dried over anhydrous $Na_2SO_4$, filtered and concentrated. The resulting residue was isolated and purified through silica gel column chromatography (mobile phase: $CH_2Cl_2$ and MeOH with a volume ratio of 20:1) to obtain the product (1.4 g) with a yield of 82%. LCMS (ESI): m/z=380 $(M+H)^+$.

(5) Synthesis of 3-(2((3-methoxy-1-methyl-1H-pyrazol-4-yl)amino)-5-methylpyrimidin-4-yl)-1H-indol-7-amine

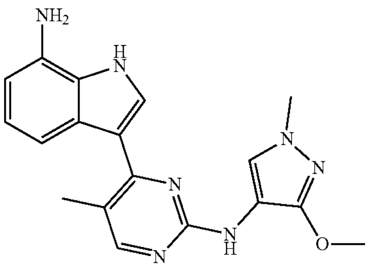

In an ice-water bath, N-(3-methoxy-1-methyl-1H-pyrazol-4-yl)-5-methyl-4-(7-nitro-1H-indol-3-yl)pyrimidin-2-amine (1.4 g, 3.7 mmol) was dissolved in EtOH (20 mL), added with AcOH (2.2 g, 37 mmol) and zinc powder (1.2 g, 18.5 mmol) and naturally warmed to room temperature to react for 1 h. After the reaction was completed, the reaction solution was poured into water and extracted with EtOAc. The ester phase was dried over anhydrous $Na_2SO_4$, filtered and concentrated to obtain the product (1.2 g) with a yield of 93%. LCMS (ESI): m/z=350 $(M+H)^+$.

Preparation Example 5

Intermediate 7 ((S)—N-(3-(5-fluoro-2-((3-methoxy-1-methyl-1H-pyrazol-4-yl)amino) pyrimidin-4-yl)-1H-indol-7-yl)pyrrolidine-2-carboxamide) was prepared.

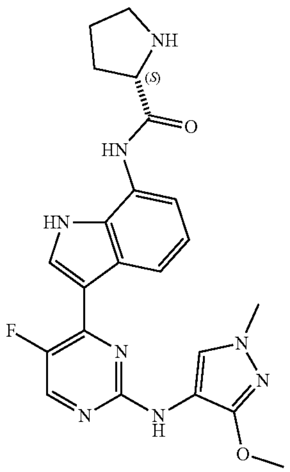

In a 100 mL round-bottom flask, Intermediate 4 (1.2 g, 3.4 mmol) and N-Boc-L-proline (731 mg, 3.4 mmol) were dissolved in $CH_2Cl_2$ (30 mL), added with N,N-diisopropylethylamine (DIEA, 877 mg, 6.8 mmol) and a condensation reagent HATU (1.9 g, 5.1 mmol) and reacted for 8 h at room temperature. After the reaction was completed, the solution was diluted with $CH_2Cl_2$. The organic phase was washed with water, dried over anhydrous $Na_2SO_4$, filtered and concentrated. The resulting residue was dissolved in $CH_2Cl_2$ (10 mL), added with TFA (10 mL) and reacted for 1 h at room temperature. After the reaction was completed, water was added, the aqueous phase was extracted with EtOAc, and layers were separated to remove the organic phase. The aqueous phase was alkaline with a saturated $Na_2CO_3$ solution and extracted with $CH_2Cl_2$. The organic phase was dried over anhydrous $Na_2SO_4$, filtered and concentrated to obtain the product (1.0 g) with a yield of 65%. LCMS (ESI): m/z=451 $(M+H)^+$.

Intermediates 8 to 12 were synthesized in sequence according to the synthesis route of Intermediate 7 in Preparation Example 5. The specific structures and mass spectrometry information of the products are shown in Table 2.

TABLE 2

| Intermediate | Compound Structure | Compound Name | LCMS (ESI) |
|---|---|---|---|
| 8 | 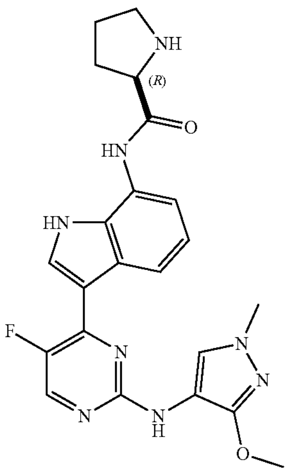 | (R)-N-(3-(5-fluoro-2-((3-methoxy-1-methyl-1H-pyrazol-4-yl)amino)pyrimidin-4-yl)-1H-indol-7-yl)pyrrolidine-2-carboxamide | 451 $(M + H)^+$ |
| 9 | 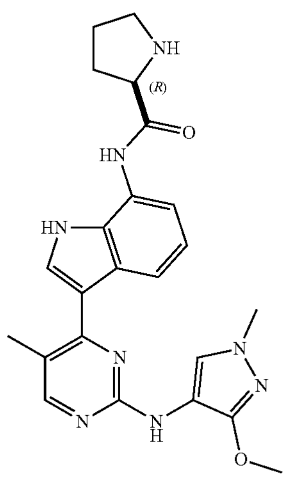 | (R)-N-(3-(2-((3-methoxy-1-methyl-1H-pyrazol-4-yl)amino)-5-methylpyrimidin-4-yl)-1H-indol-7-yl)pyrrolidine-2-carboxamide | 447 $(M + H)^+$ |

TABLE 2-continued

| Intermediate | Compound Structure | Compound Name | LCMS (ESI) |
| --- | --- | --- | --- |
| 10 | 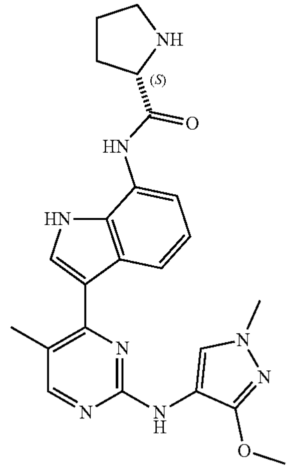 | (S)-N-(3-(2-((3-methoxy-1-methyl-1H-pyrazol-4-yl)amino)-5-methylpyrimidin-4-yl)-1H-indol-7-yl)pyrrolidine-2-carboxamide | 447 (M + H)$^+$ |
| 11 | 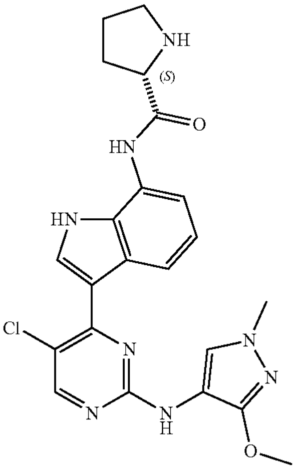 | (S)-N-(3-(5-chloro-2-((3-methoxy-1-methyl-1H-pyrazol-4-yl)amino)pyrimidin-4-yl)-1H-indol-7-yl)pyrrolidine-2-carboxamide | 467 (M + H)$^+$ |
| 12 | 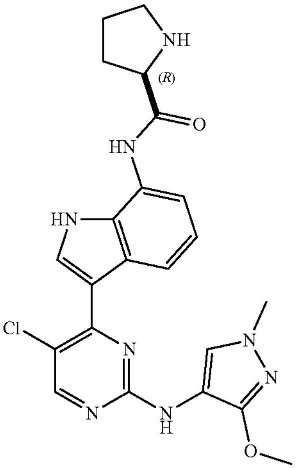 | (R)-N-(3-(5-chloro-2-((3-methoxy-1-methyl-1H-pyrazol-4-yl)amino)pyrimidin-4-yl)-1H-indol-2-yl)pyrrolidine-2-carboxamide | 467 (M + H)$^+$ |

Preparation Example 6

Intermediate 13 ((2R,4S)-4-fluoro-N-(3-(2-((3-methoxy-1-methyl-1H-pyrazol-4-yl)amino)-5-methylpyrimidin-4-yl)-1H-indol-7-yl)pyrrolidine-2-carboxamide) was prepared by the specific steps described below.

(1) Synthesis of t-butyl (2R,4S)-4-fluoro-2-((3-(2-((3-methoxy-1-methyl-1H-pyrazol-4-yl)amino)-5-methylpyrimidin-4-yl)-1H-indol-7-yl)carbamoyl)pyrrolidine-1-carboxylate

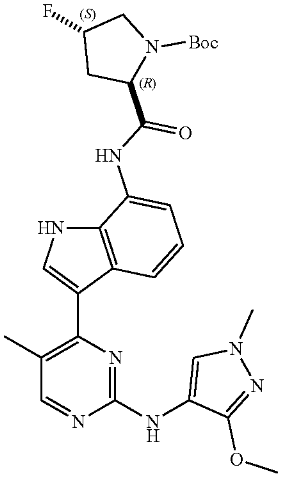

In a 100 mL round-bottom flask, Intermediate 6 (1.2 g, 3.4 mmol) and (2R,4S)—N-Boc-4-fluoropyrroline (792 mg, 3.4 mmol) were dissolved in pyridine (10 mL), added with propylphosphonic tricyclic anhydride (50%, solvent: EtOAc, 10.8 g, 17.0 mmol) and reacted for 18 h at room temperature. After the reaction was completed, the solution was diluted with EtOAc and neutralized with 4 M hydrochloric acid. The organic phase was washed with water, dried over anhydrous $Na_2SO_4$, filtered and concentrated. The resulting residue was isolated and purified through silica gel column chromatography (mobile phase: a mixed solution of $CH_2Cl_2$ and MeOH with a volume ratio of 20:1) to obtain the product (650 mg) with a yield of 34%. LCMS (ESI): m/z=565 $(M+H)^+$.

(2) Synthesis of (2R,4S)-4-fluoro-N-(3-(2-((3-methoxy-1-methyl-1H-pyrazol-4-yl)amino)-5-methylpyrimidin-4-yl)-1H-indol-7-yl)pyrrolidine-2-carboxamide

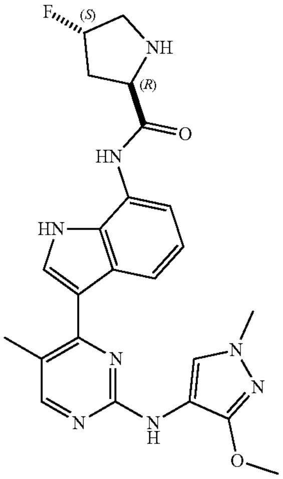

T-butyl (2R,4S)-4-fluoro-2-((3-(2-((3-methoxy-1-methyl-1H-pyrazol-4-yl)amino)-5-methylpyrimidin-4-yl)-1H-indol-7-yl)carbamoyl)pyrrolidine-1-carboxylate (650 mg, 1.2 mmol) was dissolved in $CH_2Cl_2$ (10 mL), added with TFA (10 mL) and reacted for 1 h at room temperature. After the reaction was completed, water was added, the aqueous phase was extracted with EtOAc, and layers were separated to remove the organic phase. The aqueous phase was alkaline with a saturated $Na_2CO_3$ solution and extracted with $CH_2Cl_2$. The organic phase was dried over anhydrous $Na_2SO_4$, filtered and concentrated to obtain the product (460 mg) with a yield of 83%. LCMS (ESI): m/z=465 $(M+H)^+$.

Intermediates 14 to 19 were synthesized separately according to the synthesis route of Intermediate 13 in Preparation Example 6. The specific structures and mass spectrometry information of the products are shown in Table 3.

TABLE 3

| Intermediate | Compound Structure | Compound Name | LCMS (ESI) |
|---|---|---|---|
| 14 | 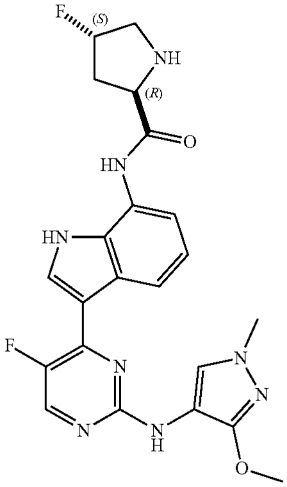 | (2R,4S)-4-fluoro-N-(3-(5-fluoro-2-((3-methoxy-1-methyl-1H-pyrazol-4-yl)amino)pyrimidin-4-yl)-1H-indol-7-yl)pyrrolidine-2-carboxamide | 469 $(M + H)^+$ |

TABLE 3-continued

| Intermediate | Compound Structure | Compound Name | LCMS (ESI) |
|---|---|---|---|
| 15 | 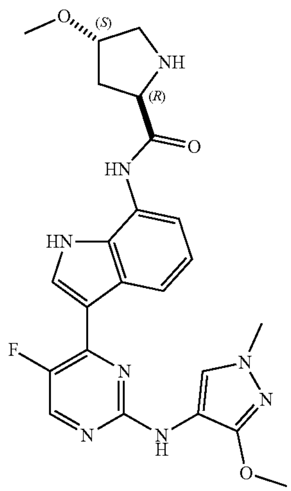 | (2R,4S)-N-(3-(5-fluoro-2-((3-methoxy-1-methyl-1H-pyrazol-4-yl)amino)pyrimidin-4-yl)-1H-indol-7-yl)-4-methoxypyrrolidine-2-carboxamide | 481 $(M + H)^+$ |
| 16 | 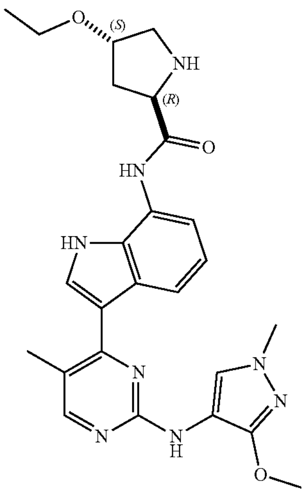 | (2R,4S)-4-ethoxy-N-(3-(2-((3-methoxy-1-methyl-1H-pyrazol-4-yl)amino)-5-methylpyrimidin-4-yl)-1H-indol-7-yl)pyrrolidine-2-carboxamide | 491 $(M + H)^+$ |
| 17 | 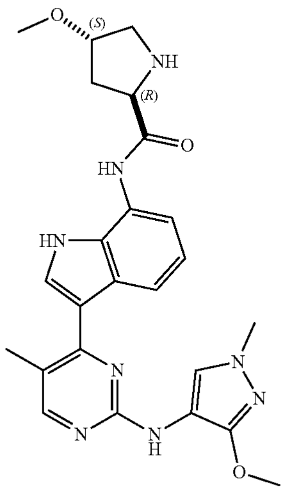 | (2R,4S)-4-methoxy-N-(3-(2-((3-methoxy-1-methyl-1H-pyrazol-4-yl)amino)-5-methylpyrimidin-4-yl)-1H-indol-7-yl)pyrrolidine-2-carboxamide | 477 $(M + H)^+$ |

TABLE 3-continued
| Intermediate | Compound Structure | Compound Name | LCMS (ESI) |
| --- | --- | --- | --- |
| 18 | 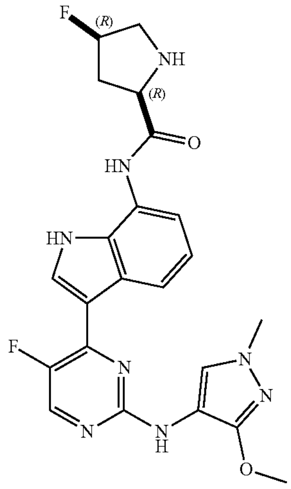 | (2R,4R)-4-fluoro-N-(3-(2-((3-methoxy-1-methyl-1H-pyrazol-4-yl)amino)-5-methylpyrimidin-4-yl)-1H-indol-7-yl)pyrrolidine-2-carboxamide | 465 $(M + H)^+$ |
| 19 | 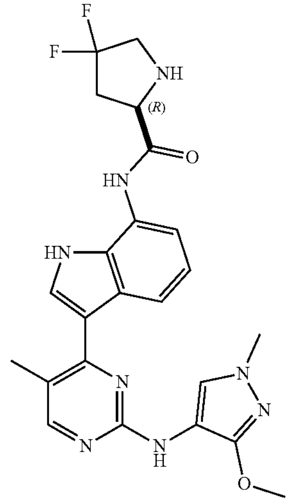 | (2R,4S)-4,4-difluoro-N-(3-(2-((3-methoxy-1-methyl-1H-pyrazol-4-yl)amino)-5-methylpyrimidin-4-yl)-1H-indol-7-yl)pyrrolidine-2-carboxamide | 483 $(M + H)^+$ |

Example 1

(S)—N-(3-(5-fluoro-2-((3-methoxy-1-methyl-1H-pyrazol-4-yl)amino)pyrimidin-4-yl)-1H-indol-7-yl)-1-(methanesulfonyl)pyrrolidine-2-carboxamide

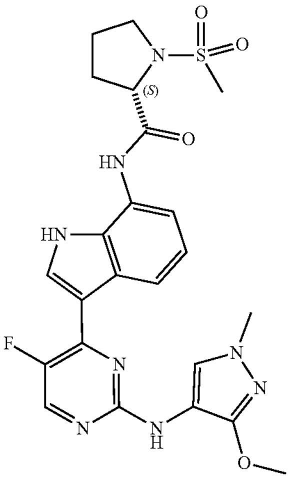

In a 25 mL round-bottom flask in an ice-water bath, Intermediate 7 (45 mg, 0.1 mmol) and triethylamine ($Et_3N$, 30 mg, 0.3 mmol) were dissolved in $CH_2Cl_2$ (2 mL), added with methanesulfonyl chloride (14 mg, 0.12 mmol) and reacted for 10 min. After the reaction was completed, the solution was concentrated under reduced pressure. The resulting residue was isolated and purified through silica gel column chromatography (mobile phase: a mixed solution of $CH_2Cl_2$ and MeOH with a volume ratio of 10:1) to obtain the product (36 mg) with a yield of 68%. LCMS (ESI): m/z=529 $(M+H)^+$.

$^1$H-NMR (400 MHz, $CDCl_3$): δ 11.61 (s, 1H), 10.05 (s, 1H), 8.50 (d, J=8.1 Hz, 1H), 8.18 (d, J=3.7 Hz, 1H), 8.07 (t, J=2.8 Hz, 1H), 7.75 (s, 1H), 7.15 (t, J=7.8 Hz, 1H), 6.82 (d, J=7.5 Hz, 1H), 6.56 (s, 1H), 4.38 (dd, J=8.6, 3.5 Hz, 1H), 3.97 (s, 3H), 3.80-3.62 (m, 4H), 3.53-3.36 (m, 1H), 2.98 (s, 3H), 2.62-2.46 (m, 1H), 2.28-2.17 (m, 1H), 2.15-2.00 (m, 2H).

Examples 2 to 4 shown in Table 4 were prepared according to the method in Example 1.

TABLE 4

| Example | Compound Structure | Compound Name | LCMS (ESI) and $^1$H-NMR (400 MHz, $CDCl_3$) |
|---|---|---|---|
| 2 | 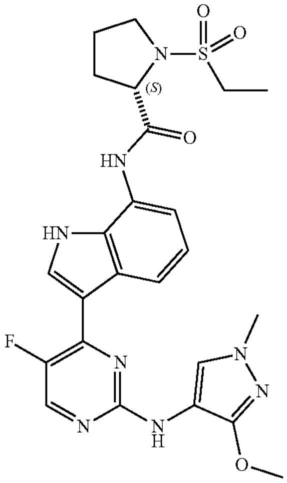 | (S)-N-(3-(5-fluoro-2-((3-methoxy-1-methyl-1H-pyrazol-4-yl)amino)pyrimidin-4-yl)-1H-indol-7-yl)-1-(ethanesulfonyl) pyrrolidine-2-carboxamide | 543 $(M + H)^+$. $^1$H-NMR: δ 10.55 (s, 1H), 8.85 (s, 1H), 8.49 (d, J = 8.0 Hz, 1H), 8.15 (d, J = 3.8 Hz, 1H), 8.03 (t, J = 2.9 Hz, 1H), 7.73 (s, 1H), 7.17 (t, J = 7.8 Hz, 1H), 7.04 (d, J = 7.3 Hz, 1H), 6.61 (s, 1H), 4.48 (dd, J = 8.5, 3.5 Hz, 1H), 3.98 (s, 3H), 3.76 (s, 3H), 3.69-3.59 (m, 1H), 3.56-3.44 (m, 1H), 3.15 (q, J = 7.2 Hz, 2H), 2.59-2.46 (m, 1H), 2.34-2.18 (m, 1H), 2.15-2.00 (m, 2H), 1.48 (t, J = 7.4 Hz, 3H). |
| 3 | 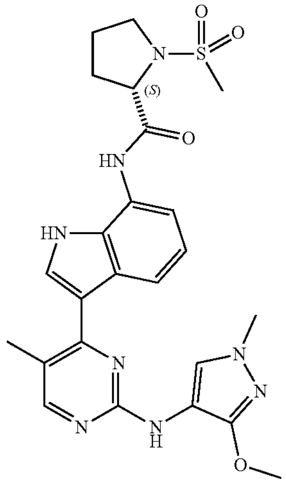 | (S)-N-(3-(2-((3-methoxy-1-methyl-1H-pyrazol-4-yl)amino)-5-methylpyrimidin-4-yl)-1H-indol-7-yl)-1-(methanesulfonyl)pyrrolidine-2-carboxamide | 525 $(M + H)^+$. $^1$H-NMR: δ 10.29 (s, 1H), 8.86 (s, 1H), 8.24 (d, J = 8.0 Hz, 1H), 8.17 (s, 1H), 7.78 (s, 1H), 7.63 (d, J = 2.8 Hz, 1H), 7.14 (t, J = 7.8 Hz, 1H), 7.06 (d, J = 7.6 Hz, 1H), 6.64 (s, 1H), 4.38 (dd, J = 8.6, 3.5 Hz, 1H), 3.97 (s, 3H), 3.80-3.62 (m, 4H), 3.53-3.36 (m, 1H), 2.98 (s, 3H), 2.62-2.46 (m, 1H), 2.31 (s, 3H), 2.28-2.17 (m, 1H), 2.15-2.00 (m, 2H). |

TABLE 4-continued

| Example | Compound Structure | Compound Name | LCMS (ESI) and $^1$H-NMR (400 MHz, $CDCl_3$) |
| --- | --- | --- | --- |
| 4 | 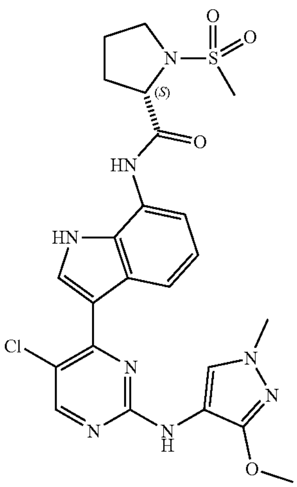 | (S)-N-(3-(5-chloro-2-((3-methoxy-1-methyl-1H-pyrazol-4-yl)amino)pyrimidin-4-yl)-1H-indol-7-yl)-1-(methanesulfonyl)pyrrolidine-2-carboxamide | 545 $(M + H)^+$. $^1$H-NMR: δ 10.29 (s, 1H), 8.86 (s, 1H), 8.24 (d, J = 8.0 Hz, 1H), 8.17 (s, 1H), 7.78 (s, 1H), 7.63 (d, J = 2.8 Hz, 1H), 7.14 (t, J = 7.8 Hz, 1H), 7.06 (d, J = 7.6 Hz, 1H), 6.64 (s, 1H), 4.38 (dd, J = 8.6, 3.5 Hz, 1H), 3.97 (s, 3H), 3.80-3.62 (m, 4H), 3.53-3.36 (m, 1H), 2.98 (s, 3H), 2.62-2.46 (m, 1H), 2.28-2.17 (m, 1H), 2.15-2.00 (m, 2H). |

Example 5

(R)—N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide

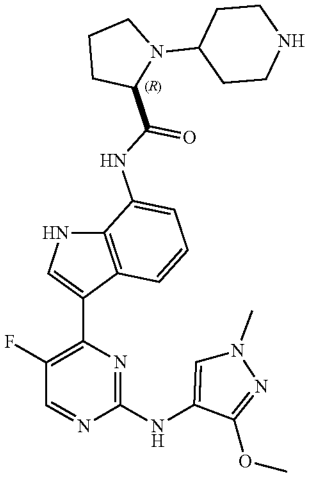

In an ice-water bath, Intermediate 8 (90 mg, 0.2 mmol), N-t-butoxycarbonyl-4-piperidone (80 mg, 0.4 mmol), $CH_2Cl_2$ (3 mL) and MeOH (2 mL) were added in a 25 mL round-bottom flask. Sodium cyanoborohydride (19 mg, 0.3 mmol) was added to the above reaction solution and reacted for 30 min. Then, TFA (5 mL) was carefully added and reacted for 1 h at room temperature. After the reaction was completed, water was added, the aqueous phase was extracted with EtOAc, and layers were separated to remove the organic phase. The aqueous phase was alkaline with a saturated $Na_2CO_3$ solution and extracted with $CH_2Cl_2$. The organic phase was dried over anhydrous $Na_2SO_4$, filtered and concentrated. The resulting residue was isolated and purified through silica gel column chromatography (mobile phase: $CH_2Cl_2$ and MeOH with a volume ratio of 10:1, 0.1% $Et_3N$) to obtain the product (64 mg) with a yield of 60%. LCMS (ESI): m/z=534 $(M+H)^+$.

$^1$H-NMR (400 MHz, $CDCl_3$): δ 11.61 (s, 1H), 10.05 (s, 1H), 8.50 (d, J=8.1 Hz, 1H), 8.18 (d, J=3.7 Hz, 1H), 8.07 (t, J=2.8 Hz, 1H), 7.75 (s, 1H), 7.15 (t, J=7.8 Hz, 1H), 6.82 (d, J=7.5 Hz, 1H), 6.56 (s, 1H), 3.98 (s, 3H), 3.76 (s, 3H), 3.56-3.46 (m, 1H), 3.29 (t, J=7.3 Hz, 1H), 3.22-3.05 (m, 2H), 2.71-2.52 (m, 4H), 2.31-2.05 (m, 2H), 2.02-1.72 (m, 4H), 1.64-1.45 (m, 2H).

Examples 6 to 17 shown in Table 5 were prepared according to the method in Example 5.

TABLE 5

| Example | Compound Structure | Compound Name | LCMS (ESI) and $^1$H-NMR (400 MHz, $CDCl_3$) |
|---|---|---|---|
| 6 | 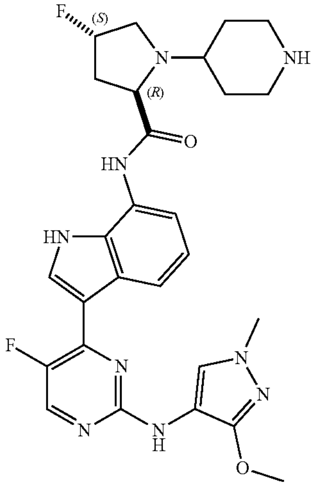 | (2R,4S)-4-fluoro-N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide | 552 $(M + H)^+$. $^1$H-NMR: δ 11.45 (s, 1H), 9.76 (s, 1H), 8.52 (d, J = 8.1 Hz, 1H), 8.18 (d, J = 3.7 Hz, 1H), 8.07 (t, J = 2.6 Hz, 1H), 7.74 (s, 1H), 7.15 (t, J = 7.8 Hz, 1H), 6.80 (dd, J = 7.6, 1.0 Hz, 1H), 6.58 (s, 1H), 5.20 (d, J = 53.4 Hz, 1H), 3.98 (s, 3H), 3.96-3.87 (m, 1H), 3.75 (s, 3H), 3.53-3.35 (m, 1H), 3.33-3.10 (m, 3H), 2.79-2.55 (m, 4H), 2.17-1.97 (m, 2H), 1.97-1.83 (m, 2H), 1.67-1.44 (m, 2H). |
| 7 | 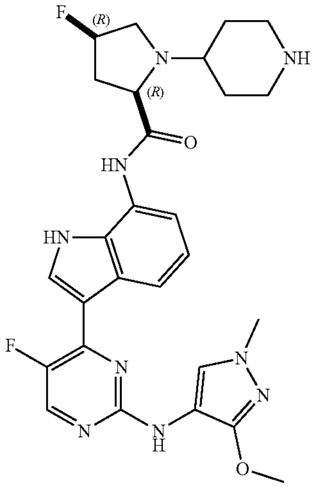 1503 | (2R,4R)-4-fluoro-N-(3-(5-fluoro-2-((3-methoxy-1-methyl-1H-pyrazol-4-yl)amino)pyrimidin-4-yl)-1H-indol-7-yl)-1-(piperidin-4-yl)pyrrolidine-2-carboxamide | 552 $(M + H)^+$. $^1$H-NMR: δ 11.34 (s, 1H), 9.77 (s, 1H), 8.50 (d, J = 8.1 Hz, 1H), 8.17 (d, J = 3.7 Hz, 1H), 8.06 (d, J = 2.9 Hz, 1H), 7.75 (s, 1H), 7.15 (t, J = 7.8 Hz, 1H), 6.86 (d, J = 7.6 Hz, 1H), 6.55 (s, 1H), 5.21 (d, J = 52.3 Hz, 1H), 3.98 (s, 3H), 3.75 (s, 3H), 3.67-3.47 (m, 2H), 3.25-3.07 (m, 2H), 2.94-2.73 (m, 1H), 2.69-2.36 (m, 4H), 1.96-1.82 (m, 4H), 1.69-1.49 (m, 2H). |
| 8 | 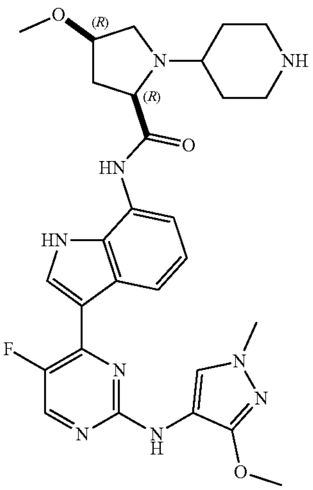 1501 | (2R,4R)-N-(3-(5-fluoro-2-((3-methoxy-1-methyl-1H-pyrazol-4-yl)amino)pyrimidin-4-yl)-1H-indol-7-yl)-4-methoxy-1-(piperidin-4-yl) pyrrolidine-2-carboxamide | 564 $(M + H)^+$. $^1$H-NMR: δ 11.54 (s, 1H), 9.85 (s, 1H), 8.51 (d, J = 8.1 Hz, 1H), 8.18 (d, J = 3.8 Hz, 1H), 8.07 (t, J = 2.8 Hz, 1H), 7.75 (s, 1H), 7.15 (t, J = 7.8 Hz, 1H), 6.81 (d, J = 7.5 Hz, 1H), 6.55 (s, 1H), 3.98 (s, 3H), 3.96-3.89 (m, 1H), 3.76 (s, 3H), 3.74-3.65 (m, 1H), 3.48-3.39 (m, 1H), 3.34 (s, 3H), 3.22-3.08 (m, 2H), 2.88-2.78 (m, 1H), 2.69-2.53 (m, 2H), 2.42-2.28 (m, 1H), 2.23-2.11 (m, 1H), 1.89-1.77 (m, 3H), 1.63-1.43 (m, 2H). |

TABLE 5-continued

| Example | Compound Structure | Compound Name | LCMS (ESI) and $^1$H-NMR (400 MHz, $CDCl_3$) |
|---|---|---|---|
| 9 | 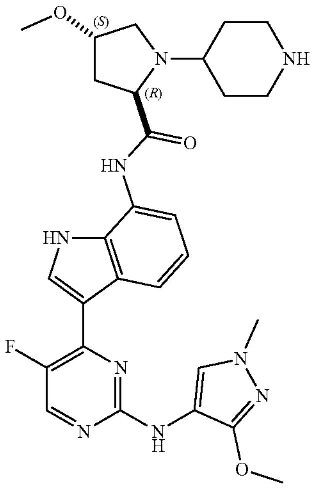 | (2R,4S)-N-(3-(5-fluoro-2-((3-methoxy-1-methyl-1H-pyrazol-4-yl)amino)pyrimidin-4-yl)-1H-indol-7-yl)-4-methoxy-1-(piperidin-4-yl)pyrrolidine-2-carboxamide | 564 $(M + H)^+$. $^1$H-NMR: δ 11.54 (s, 1H), 9.85 (s, 1H), 8.51 (d, J = 8.1 Hz, 1H), 8.18 (d, J = 3.8 Hz, 1H), 8.07 (t, J = 2.8 Hz, 1H), 7.75 (s, 1H), 7.15 (t, J = 7.8 Hz, 1H), 6.81 (d, J = 7.5 Hz, 1H), 6.55 (s, 1H), 3.98 (s, 3H), 3.96-3.89 (m, 1H), 3.76 (s, 3H), 3.74-3.65 (m, 1H), 3.48-3.39 (m, 1H), 3.34 (s, 3H), 3.22-3.08 (m, 2H), 2.88-2.78 (m, 1H), 2.69-2.53 (m, 2H), 2.42-2.28 (m, 1H), 2.23-2.11 (m, 1H), 1.89-1.77 (m, 3H), 1.63-1.43 (m, 2H). |
| 10 | 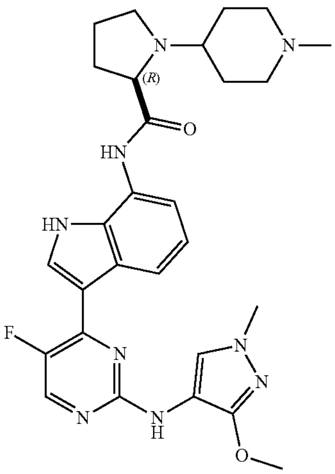 | (R)-N-(3-(5-fluoro-2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide | 548 $(M + H)^+$. $^1$H-NMR: δ 11.60 (s, 1H), 10.03 (s, 1H), 8.49 (d, J = 8.1 Hz, 1H), 8.17 (d, J = 3.8 Hz, 1H), 8.06 (t, J = 2.9 Hz, 1H), 7.75 (s, 1H), 7.14 (t, J = 7.8 Hz, 1H), 6.81 (d, J = 7.5 Hz, 1H), 6.56 (s, 1H), 3.98 (s, 3H), 3.76 (s, 3H), 3.55-3.44 (m, 1H), 3.35-3.26 (m, 1H), 3.00-2.91 (m, 1H), 2.89-2.82 (m, 1H), 2.68-2.58 (m, 1H), 2.51-2.40 (m, 1H), 2.27 (s, 3H), 2.25-2.08 (m, 2H), 2.06-1.91 (m, 4H), 1.90-1.77 (m, 2H), 1.76-1.64 (m, 2H). |
| 11 | 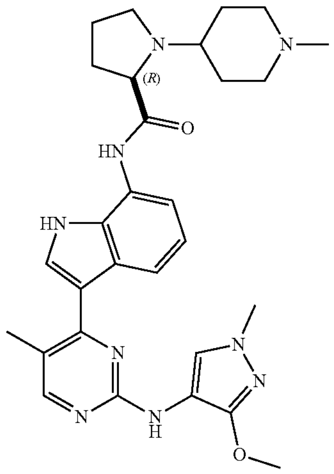 | (R)-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide | 544 $(M + H)^+$. $^1$H-NMR: δ 11.36 (s, 1H), 10.01 (s, 1H), 8.25-8.17 (m, 2H), 7.82 (s, 1H), 7.66 (d, J = 2.8 Hz, 1H), 7.10 (t, J = 7.8 Hz, 1H), 6.81 (d, J = 7.4 Hz, 1H), 6.57 (s, 1H), 3.97 (s, 3H), 3.69 (s, 3H), 3.54-3.45 (m, 1H), 3.38-3.25 (m, 1H), 2.98-2.90 (m, 1H), 2.90-2.82 (m, 1H), 2.71-2.57 (m, 1H), 2.53-2.41 (m, 1H), 2.35 (s, 3H), 2.27 (s, 3H), 2.24-2.07 (m, 2H), 2.05-1.90 (m, 5H), 1.89-1.64 (m, 3H). |

TABLE 5-continued

| Example | Compound Structure | Compound Name | LCMS (ESI) and $^1$H-NMR (400 MHz, $CDCl_3$) |
|---|---|---|---|
| 12 | 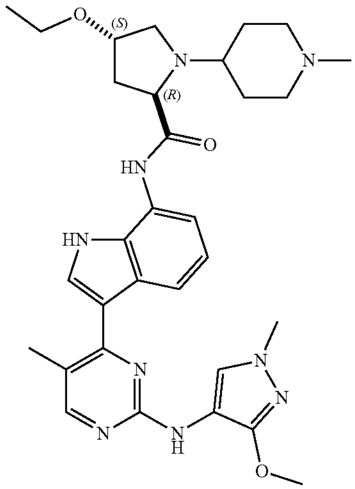 | (2R,4S)-4-ethoxy-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide | 588 $(M + H)^+$. $^1$H-NMR: δ 11.30 (s, 1H), 9.85 (s, 1H), 8.34-8.10 (m, 2H), 7.81 (s, 1H), 7.67 (d, J = 2.7 Hz, 1H), 7.10 (t, J = 7.8 Hz, 1H), 6.79 (d, J = 7.5 Hz, 1H), 6.56 (s, 1H), 4.10-4.01 (m, 1H), 3.97 (s, 3H), 3.77-3.63 (m, 4H), 3.57-3.38 (m, 3H), 2.99-2.91 (m, 1H), 2.91-2.83 (m, 1H), 2.82-2.72 (m, 1H), 2.58-2.46 (m, 1H), 2.35 (s, 3H), 2.32-2.15 (m, 5H), 2.06-1.78 (m, 4H), 1.77-1.59 (m, 2H), 1.20 (t, J = 7.0 Hz, 2H). |
| 13 | 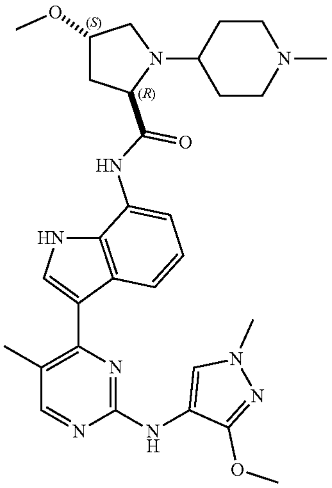 | (2R,4S)-4-methoxy-N-(3-(2-((3-methoxy-1-methyl-1H-pyrazol-4-yl)amino)-5-methyl-pyrimidin-4-yl)-1H-indol-7-yl)-1-(1-methylpiperidin-4-yl)pyrrolidine-2-carboxamide | 574 $(M + H)^+$. $^1$H-NMR: δ 11.30 (s, 1H), 9.85 (s, 1H), 8.34-8.10 (m, 2H), 7.81 (s, 1H), 7.67 (d, J = 2.7 Hz, 1H), 7.10 (t, J = 7.8 Hz, 1H), 6.79 (d, J = 7.5 Hz, 1H), 6.56 (s, 1H), 4.10-4.01 (m, 1H), 3.97 (s, 3H), 3.77-3.63 (m, 4H), 3.57-3.38 (m, 4H), 2.99-2.91 (m, 1H), 2.91-2.83 (m, 1H), 2.82-2.72 (m, 1H), 2.58-2.46 (m, 1H), 2.35 (s, 3H), 2.32-2.15 (m, 5H), 2.06-1.78 (m, 4H), 1.77-1.59 (m, 2H). |
| 14 | 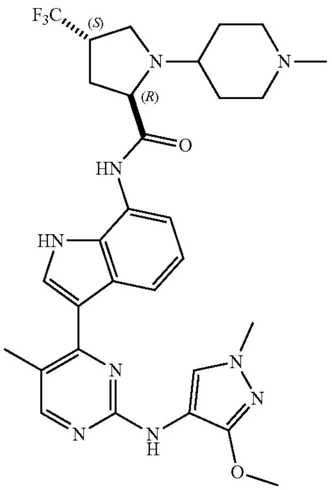 | (2R,4S)-4-fluoro-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide | 562 $(M + H)^+$. $^1$H-NMR: δ 11.21 (s, 1H), 9.73 (s, 1H), 8.29-8.15 (m, 2H), 7.81 (s, 1H), 7.66 (d, J = 2.8 Hz, 1H), 7.10 (t, J = 7.8 Hz, 1H), 6.78 (d, J = 7.5 Hz, 1H), 6.57 (s, 1H), 5.20 (d, J = 53.6 Hz, 1H), 3.97 (s, 3H), 3.93-3.84 (m, 1H), 3.69 (s, 3H), 3.56-3.36 (m, 1H), 3.32-3.16 (m, 1H), 3.00-2.83 (m, 2H), 2.78-2.54 (m, 2H), 2.35 (s, 3H), 2.26 (s, 3H), 2.16-2.00 (m, 1H), 2.00-1.90 (m, 4H), 1.78-1.58 (m, 2H). |

TABLE 5-continued

| Example | Compound Structure | Compound Name | LCMS (ESI) and $^1$H-NMR (400 MHz, $CDCl_3$) |
|---|---|---|---|
| 15 | 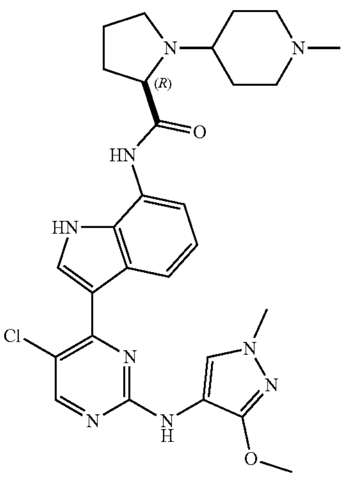 | (R)-N-(3-(5-chloro-2-((3-methoxy-1-methyl-1H-pyrazol-4-yl)amino) pyrimidin-4-yl)-1H-indol-7-yl)-1-(1-methypiperidin-4-yl)pyrrolidine-2-carboxamide | 564 $(M + H)^+$. $^1$H-NMR: δ 11.55 (s, 1H), 10.03 (s, 1H), 8.43-8.18 (m, 3H), 7.77 (s, 1H), 7.11 (t, J = 7.8 Hz, 1H), 6.80 (d, J = 7.4 Hz, 1H), 6.67 (s, 1H), 3.98 (s, 3H), 3.71 (s, 3H), 3.49 (dd, J = 10.5, 2.9 Hz, 1H), 3.30 (t, J = 7.6 Hz, 1H), 2.92 (d, J = 11.5 Hz, 1H), 2.84 (d, J = 11.5 Hz, 1H), 2.69-2.57 (m, 1H), 2.51-2.40 (m, 1H), 2.26 (s, 3H), 2.23-2.07 (m, 2H), 2.00-1.87 (m, 5H), 1.75-1.61 (m, 3H). |
| 16 | 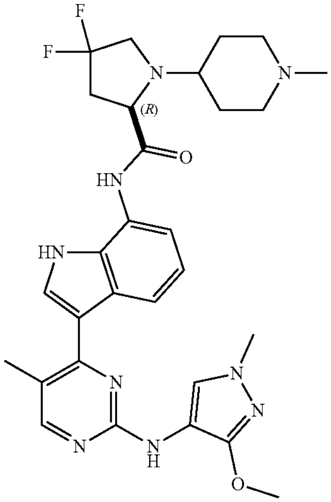 | (R)-4,4-difluoro-N-(3-(2-((3-methoxy-1-methyl-1H-pyrazol-4-yl)amino)-5-methylpyrimidin-4-yl)-1H-indol-7-yl)-1-(1-methylpiperidin-4-yl)pyrrolidine-2-carboxamide | 580 $(M + H)^+$. $^1$H-NMR: δ 11.01 (s, 1H), 9.60 (s, 1H), 8.25 (d, J = 8.1 Hz, 1H), 8.21 (s, 1H), 7.81 (s, 1H), 7.66 (d, J = 2.7 Hz, 1H), 7.12 (t, J = 7.8 Hz, 1H), 6.82 (d, J = 7.5 Hz, 1H), 6.57 (s, 1H), 3.98 (s, 3H), 3.81-3.74 (m, 1H), 3.70 (s, 3H), 3.59-3.44 (m, 1H), 3.22-3.04 (m, 1H), 2.94 (d, J = 11.7 Hz, 1H), 2.88 (d, J = 11.8 Hz, 1H), 2.84-2.69 (m, 1H), 2.62-2.43 (m, 2H), 2.35 (s, 3H), 2.26 (s, 3H), 2.03-1.91 (m, 4H), 1.77-1.60 (m, 2H). |
| 17 | 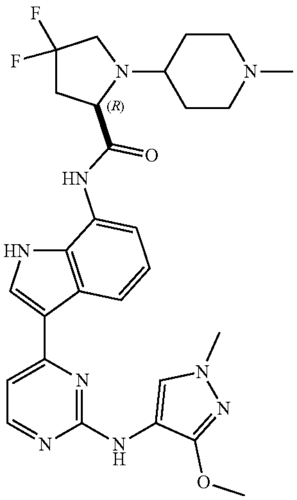 | (R)-4,4-difluoro-N-(3-(2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide | 566 $(M + H)^+$. $^1$H-NMR: δ 11.09 (s, 1H), 9.60 (s, 1H), 8.31 (s, 1H), 8.30 (s, 1H), 7.88 (d, J = 2.8 Hz, 1H), 7.82 (s, 1H), 7.15 (t, J = 7.8 Hz, 1H), 6.98 (d, J = 5.3 Hz, 1H), 6.81 (d, J = 7.5 Hz, 1H), 6.64 (s, 1H), 3.98 (s, 3H), 3.83-3.73 (m, 4H), 3.57-3.44 (m, 1H), 3.25-3.06 (m, 1H), 3.00-2.84 (m, 2H), 2.82-2.66 (m, 1H), 2.62-2.43 (m, 2H), 2.26 (s, 3H), 2.05-1.90 (m, 3H), 1.79-1.58 (m, 3H). |

Example 18 and Example 19

(2R,3'R,4S)-4-fluoro-N-(3-(2-((3-methoxy-1-methyl-1H-pyrazol-4-yl)amino)pyrimidin-4-yl)-1H-indol-7-yl)-[1,3'-bipyrrolidine]-2-carboxamide (Example 18) and (2R,3'S,4S)-4-fluoro-N-(3-(2-((3-methoxy-1-methyl-1H-pyrazol-4-yl)amino) pyrimidin-4-yl)-1H-indol-7-yl)-[1,3'-bipyrrolidine]-2-carboxamide (Example 19)

(1) Synthesis of 2-benzyl 1-(t-butyl) (2R,4S)-4-fluoropyrrolidine-1,2-dicarboxylate

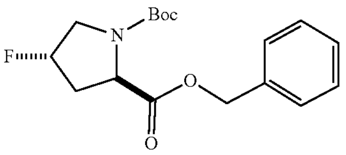 [SMILES: CC(C)(C)OC(=O)N1C[C@@H](F)C[C@@H]1C(=O)OCc1ccccc1]

In a 250 mL round-bottom flask, (2R,4S)-1-(t-butoxycarbonyl)-4-fluoropyrrolidine-2-carboxylic acid (7.0 g, 30.0 mmol), cesium carbonate (14.6 g, 45.0 mmol) and MeCN (100 mL) were added and stirred at room temperature to react for 1 h. Benzyl bromide (7.7 g, 45.0 mmol) was added to the above reaction system and then heated to 60° C. to react for 2 h. After the reaction was completed, the solution was filtered and the filter residue was washed with EtOAc. The filtrate was concentrated to remove the solvent to obtain the product (8.5 g) with a yield of 88%.

LCMS (ESI): m/z=324 $(M+H)^+$.

(2) Synthesis of benzyl (2R,4S)-4-fluoropyrrolidine-2-carboxylate

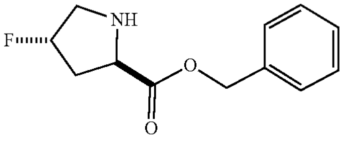 [SMILES: O=C(OCc1ccccc1)[C@H]1C[C@H](F)CN1]

2-Benzyl 1-(t-butyl) (2R,4S)-4-fluoropyrrolidine-1,2-dicarboxylate (8.5 g, 26.3 mmol) was dissolved in MeOH (40 mL), cooled in an ice-water bath, added with concentrated hydrochloric acid (12 M, 20 mL) and naturally warmed to room temperature to react for 1 h. After the reaction was completed, the solution was concentrated under reduced pressure to remove methanol, the residue was dissolved in water, the aqueous phase was extracted with EtOAc, and layers were separated to remove the organic phase. The aqueous phase was alkaline with a saturated $Na_2CO_3$ solution and extracted with $CH_2Cl_2$. The organic phase was dried over anhydrous $Na_2SO_4$, filtered and concentrated to obtain the product (5.2 g) with a yield of 89%.

LCMS (ESI): m/z=224 $(M+H)^+$.

(3) Synthesis of 2-benzyl 1'-(t-butyl) (2R,4S)-4-fluoro-[1,3'-bipyrrolidine]-1',2-dicarboxylate

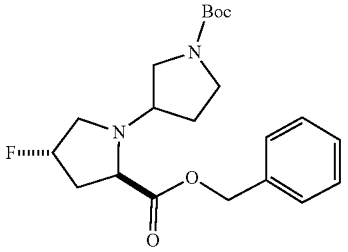 [SMILES: CC(C)(C)OC(=O)N1CCC(N2C[C@@H](F)C[C@@H]2C(=O)OCc2ccccc2)C1]

In an ice-water bath, benzyl (2R,4S)-4-fluoropyrrolidine-2-carboxylate (5.2 g, 23.3 mmol), N-Boc-3-pyrrolidone (6.6 g, 35.6 mmol) and MeOH (50 mL) were added in a 100 mL round-bottom flask. Sodium cyanoborohydride (2.2 g, 35.6 mmol) was added to the above reaction solution and reacted for 20 h. After the reaction was completed, the solution was added with water and concentrated under reduced pressure to remove methanol and the aqueous phase was extracted with EtOAc. The organic phase was dried over anhydrous $Na_2SO_4$, filtered and concentrated. The resulting residue was isolated and purified through silica gel column chromatography (mobile phase: a mixed solution of PE and EtOAc with a volume ratio of 10:1) to obtain the product (7.6 g) with a yield of 83%. LCMS (ESI): m/z=393 $(M+H)^+$.

(4) Synthesis of (2R,4S)-1'-(t-butoxycarbonyl)-4-fluoro-[1,3'-bipyrrolidine]-2-carboxylic acid

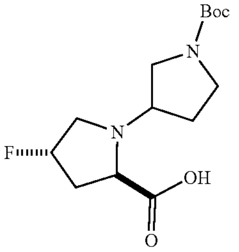 [SMILES: CC(C)(C)OC(=O)N1CCC(N2C[C@@H](F)C[C@@H]2C(=O)O)C1]

In a 250 mL three-necked round-bottom flask equipped with a hydrogen balloon, 2-benzyl 1'-(t-butyl) (2R,4S)-4-fluoro-[1,3'-bipyrrolidine]-1',2-dicarboxylate (7.6 g, 19.4 mmol) was dissolved in MeOH (40 mL), added with Pd/C (2.0 g, 10%, 55 wt % water) and reacted for 20 h at room temperature. After the reaction was completed, the solution was filtered and the filter residue was washed with methanol. The filtrate was concentrated under reduced pressure to obtain the product (4.9 g) with a yield of 85%. LCMS (ESI): m/z=303 $(M+H)^+$.

(5) Synthesis of t-butyl (2R,4S)-4-fluoro-2-((3-(2-((3-methoxy-1-methyl-1H-pyrazol-4-yl)amino) pyrimidin-4-yl)-1H-indol-7-yl)carbamoyl)-[1,3'-bipyrrolidine]-1'-carboxylate

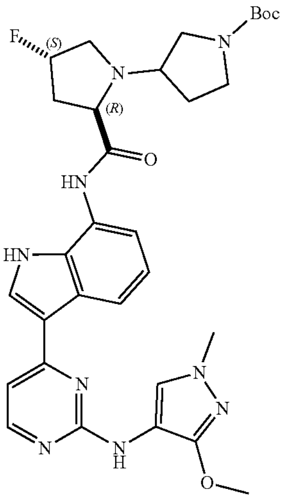

In a 50 mL round-bottom flask, Intermediate 3 (191 mg, 0.57 mmol) and (2R,4S)-1'-(t-butoxycarbonyl)-4-fluoro-[1,3'-bipyrrolidine]-2-carboxylic acid (172 mg, 0.57 mmol) were dissolved in DMF (5 mL), added with DIEA (219 mg, 1.7 mmol) and HATU (260 mg, 0.68 mmol) and reacted for 1 h at room temperature. After the reaction was completed, the solution was diluted with $CH_2Cl_2$. The organic phase was washed with water, dried over anhydrous $Na_2SO_4$, filtered and concentrated. The resulting residue was isolated and purified through silica gel column chromatography (mobile phase: a mixed solution of $CH_2Cl_2$ and MeOH with a volume ratio of 30:1) to obtain the product (254 mg) with a yield of 72%. LCMS (ESI): m/z=620 $(M+H)^+$.

(6) Synthesis of (2R,3'R,4S)-4-fluoro-N-(3-(2-((3-methoxy-1-methyl-1H-pyrazol-4-yl)amino) pyrimidin-4-yl)-1H-indol-7-yl)-[1,3'-bipyrrolidine]-2-carboxamide and (2R,3'S,4S)-4-fluoro-N-(3-(2-((3-methoxy-1-methyl-1H-pyrazol-4-yl)amino) pyrimidin-4-yl)-1H-indol-7-yl)-[1,3'-bipyrrolidine]-2-carboxamide

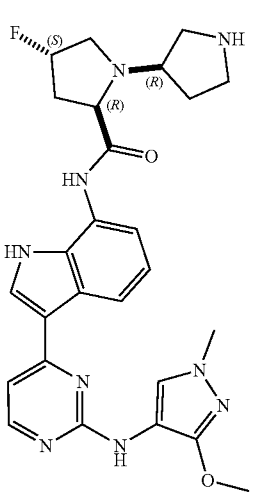

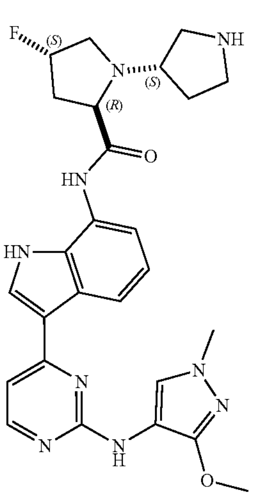

In a 50 mL round-bottom flask, t-butyl (2R,4S)-4-fluoro-2-((3-(2-((3-methoxy-1-methyl-1H-pyrazol-4-yl)amino)pyrimidin-4-yl)-1H-indol-7-yl)carbamoyl)-[1,3'-bipyrrolidine]-1'-carboxylate (127 mg, 0.21 mmol) was dissolved in $CH_2Cl_2$ (5 mL) and cooled in an ice-water bath. Then, TFA (2.0 mL) was added to the above solution and reacted for 1 h at room temperature. After the reaction was completed, the solution was concentrated under reduced pressure to remove TFA and the solvent. The residue was isolated by a chiral column (chiral ND(2) SU 250×21.1 mm; mobile phase: a mixed solution of ethanol, isopropanol, methanol and n-hexane with a volume ratio of 35:30:10:15 (containing 0.3% triethylamine); flow rate: 12 mL/min). The first eluted component (42 mg) was Example 18 with a yield of 38%. LCMS (ESI): m/z=520 $(M+H)^+$. $^1$H-NMR (400 MHz, $CDCl_3$): δ 12.05 (s, 1H), 10.05 (s, 1H), 8.30 (d, J=5.3 Hz, 1H), 8.23 (d, J=8.0 Hz, 1H), 7.85 (s, 1H), 7.82 (s, 1H), 7.32-7.25 (m, 1H), 7.19 (t, J=7.8 Hz, 1H), 6.97 (d, J=5.3 Hz, 1H), 6.62 (s, 1H), 5.21 (d, J=53.1 Hz, 1H), 3.98 (s, 3H), 3.85-3.70 (m, 5H), 3.60-3.51 (m, 1H), 3.49-3.32 (m, 1H), 3.29-3.19 (m, 2H), 3.18-3.07 (m, 2H), 3.06-2.97 (m, 1H), 2.86-2.69 (m, 1H), 2.29-2.07 (m, 1H), 2.06-1.98 (m, 2H). The second eluted component (36 mg) was Example 19 with a yield of 33%. LCMS (ESI): m/z=520 $(M+H)^+$. $^1$H-NMR (400 MHz, $CDCl_3$): δ 12.35 (s, 1H), 9.68 (s, 1H), 8.30 (d, J=5.3 Hz, 1H), 8.23 (d, J=8.0 Hz, 1H), 7.83 (s, 1H), 7.81 (s, 1H), 7.32-7.25 (m, 1H), 7.19 (t, J=7.8 Hz, 1H), 6.97 (d, J=5.3 Hz, 1H), 6.62 (s, 1H), 5.21 (d, J=53.1 Hz, 1H), 3.96 (s, 3H), 3.85-3.70 (m, 5H), 3.60-3.51 (m, 1H), 3.49-3.32 (m, 1H), 3.29-3.19 (m, 2H), 3.18-3.07 (m, 2H), 3.06-2.97 (m, 1H), 2.86-2.69 (m, 1H), 2.29-2.07 (m, 1H), 2.06-1.98 (m, 2H).

Example 20 and Example 21

(2R,3'R,4S)-4-fluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide (Example 20) and (2R,3'S,4S)-4-fluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide (Example 21)

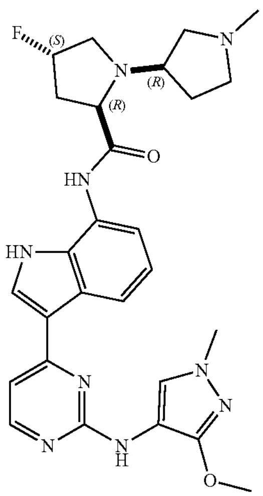

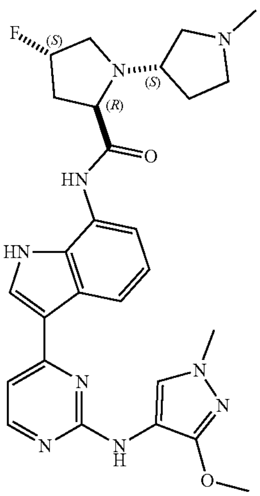

In an ice-water bath, (2R,4S)-4-fluoro-N-(3-(2-((3-methoxy-1-methyl-1H-pyrazol-4-yl)amino) pyrimidin-4-yl)-1H-indol-7-yl)-[1,3'-bipyrrolidine]-2-carboxamide (127 mg, 0.21 mmol), 40% aqueous formaldehyde (47 mg, 0.63 mmol) and MeOH (10 mL) were added in a 50 mL round-bottom flask. Sodium cyanoborohydride (2.2 g, 35.6 mmol) was added to the above reaction solution and reacted for 1 h. After the reaction was completed, the solution was added with water and concentrated under reduced pressure to remove methanol and the aqueous phase was extracted with EtOAc. The organic phase was dried over anhydrous $Na_2SO_4$, filtered and concentrated. The residue was isolated by a chiral column (chiral ND(2) SU 250×21.1 mm; mobile phase: a mixed solution of ethanol, isopropanol, methanol and n-hexane with a volume ratio of 35:30:10:15 (containing 0.3% triethylamine); flow rate: 12 mL/min). The first eluted component (37 mg) was Example 20 with a yield of 33%. LCMS (ESI): m/z=534 $(M+H)^+$.

$^1$H-NMR (400 MHz, $CDCl_3$): δ 11.50 (s, 1H), 9.96 (s, 1H), 8.31 (d, J=5.3 Hz, 1H), 8.22 (d, J=8.0 Hz, 1H), 7.86 (s, 1H), 7.83 (s, 1H), 7.31-7.24 (m, 1H), 7.20 (t, J=7.8 Hz, 1H), 6.99 (d, J=5.3 Hz, 1H), 6.62 (s, 1H), 5.20 (d, J=53.0 Hz, 1H), 3.98 (s, 3H), 3.84-3.72 (m, 4H), 3.63-3.53 (m, 1H), 3.50-3.31 (m, 1H), 3.25-3.08 (m, 2H), 3.03-2.92 (m, 1H), 2.87-2.70 (m, 4H), 2.42-2.27 (m, 2H), 2.26-2.15 (m, 1H), 2.11-1.93 (m, 2H). The second eluted component (30 mg) was Example 21 with a yield of 27%. LCMS (ESI): m/z=534 $(M+H)^+$.

$^1$H-NMR (400 MHz, $CDCl_3$): δ 11.30 (s, 1H), 9.86 (s, 1H), 8.31 (d, J=5.3 Hz, 1H), 8.21 (d, J=8.0 Hz, 1H), 7.86 (s, 1H), 7.84 (s, 1H), 7.31-7.24 (m, 1H), 7.20 (t, J=7.8 Hz, 1H), 6.99 (d, J=5.3 Hz, 1H), 6.62 (s, 1H), 5.20 (d, J=53.0 Hz, 1H), 3.97 (s, 3H), 3.84-3.72 (m, 4H), 3.63-3.53 (m, 1H), 3.50-3.31 (m, 1H), 3.25-3.08 (m, 2H), 3.03-2.92 (m, 1H), 2.87-2.70 (m, 4H), 2.42-2.27 (m, 2H), 2.26-2.15 (m, 1H), 2.11-1.93 (m, 2H).

Examples 22 to 39 shown in Table 6 were prepared according to the methods in Examples 18 and 19 and Examples 20 and 21.

TABLE 6

| Example | Compound Structure | Compound Name | LCMS (ESI) and $^1$H-NMR (400 MHz, $CDCl_3$) |
|---|---|---|---|
| 22 | 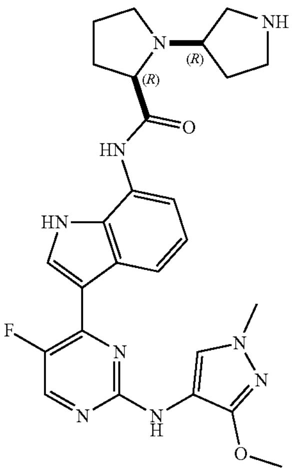 | (2R,3'R)-N-(3-(5-fluoro-2-((3-methoxy-1-methyl-1H-pyrazol-4-yl)amino)pyrimidin-4-yl)-1H-indol-7-yl)-[1,3'-bipyrrolidine]-2-carboxamide | 520 (M + H)+. $^1$H-NMR: δ 11.86 (s, 1H), 10.12 (s, 1H), 8.53-8.40 (m, 1H), 8.21-8.13 (m, 1H), 8.05-8.03 (m, 1H), 7.80-7.71 (m, 1H), 7.42 (d, J = 7.7 Hz, 1H), 7.24-7.14 (m, 1H), 6.56 (s, 1H), 3.98 (s, 3H), 3.76 (s, 3H), 3.56-2.89 (m, 6H), 2.64-2.48 (m, 1H), 2.39-1.66 (m, 8H). |
| 23 | 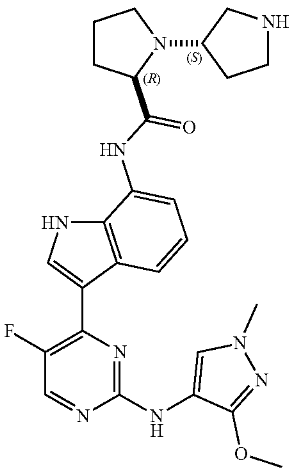 | (2R,3'S)-N-(3-(5-fluoro-2-((3-methoxy-1-methyl-1H-pyrazol-4-yl)amino)pyrimidin-4-yl)-1H-indol-7-yl)-[1,3'-bipyrrolidine]-2-carboxamide | 520 (M + H)+. $^1$H-NMR: δ 12.96 (s, 1H), 9.85 (s, 1H), 8.53-8.40 (m, 1H), 8.21-8.13 (m, 1H), 8.05-8.03 (m, 1H), 7.80-7.71 (m, 1H), 7.29 (d, J = 7.7 Hz, 1H), 7.24-7.14 (m, 1H), 6.56 (s, 1H), 3.98 (s, 3H), 3.76 (s, 3H), 3.56-2.89 (m, 6H), 2.64-2.48 (m, 1H), 2.39-1.66 (m, 8H). |

TABLE 6-continued

| Example | Compound Structure | Compound Name | LCMS (ESI) and $^1$H-NMR (400 MHz, $CDCl_3$) |
|---|---|---|---|
| 24 | 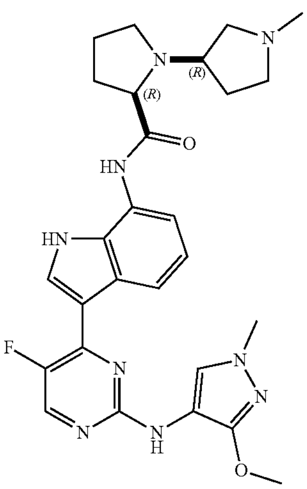 | (2R,3'R)-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 534 (M + H)+. $^1$H-NMR: δ 11.83 (s, 1H), 10.37 (s, 1H), 8.44 (d, J = 8.1 Hz, 1H), 8.18 (d, J = 3.8 Hz, 1H), 8.05-7.97 (m, 1H), 7.76 (s, 1H), 7.50-7.35 (m, 1H), 7.24-7.16 (m, 1H), 6.55 (s, 1H), 3.98 (s, 3H), 3.76 (s, 3H), 3.53-3.29 (m, 3H), 3.09-2.93 (m, 2H), 2.67-2.42 (m, 4H), 2.42-2.29 (m, 2H), 2.28-2.15 (m, 2H), 2.14-2.00 (m, 1H), 1.95-1.82 (m, 3H). |
| 25 | 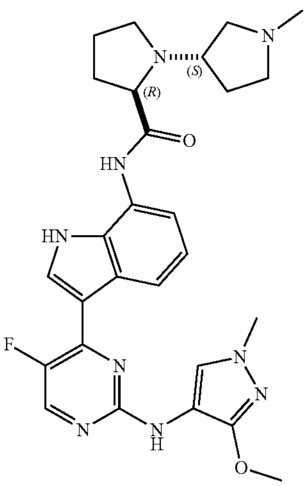 | (2R,3'S)-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 534 (M + H)+. $^{11}$H-NMR: δ 12.08 (s, 1H), 10.23 (s, 1H), 8.44 (d, J = 8.1 Hz, 1H), 8.18 (d, J = 3.8 Hz, 1H), 8.05-7.97 (m, 1H), 7.76 (s, 1H), 7.50-7.35 (m, 1H), 7.24-7.16 (m, 1H), 6.55 (s, 1H), 3.98 (s, 3H), 3.76 (s, 3H), 3.53-3.29 (m, 3H), 3.09-2.93 (m, 2H), 2.67-2.42 (m, 2H), 2.42-2.29 (m, 4H), 2.28-2.15 (m, 2H), 2.14-2.00 (m, 1H), 1.95-1.82 (m, 3H). |
| 26 | 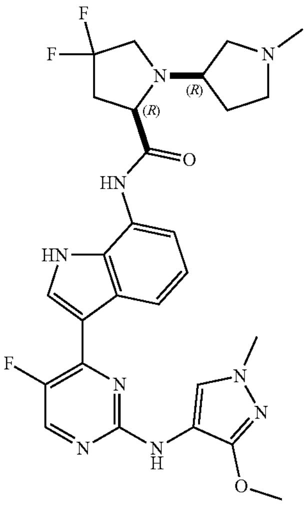 | (2R,3'R)-4,4-difluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 570 (M + H)+. $^1$H-NMR: δ 11.53 (s, 1H), 9.98 (s, 1H), 8.48 (d, J = 8.1 Hz, 1H), 8.18 (d, J = 3.7 Hz, 1H), 8.06-7.98 (m, 1H), 7.75 (s, 1H), 7.36 (d, J = 7.6 Hz, 1H), 7.21 (t, J = 7.8 Hz, 1H), 6.55 (s, 1H), 3.99 (s, 3H), 3.76 (s, 3H), 3.71-3.63 (m, 1H), 3.63-3.41 (m, 2H), 3.26-3.18 (m, 1H), 3.15-2.94 (m, 2H), 2.93-2.74 (m, 1H), 2.70-2.55 (m, 1H), 2.49 (s, 3H), 2.43-2.27 (m, 2H), 2.26-2.07 (m, 1H), 2.03-1.83 (m, 1H). |

TABLE 6-continued

| Example | Compound Structure | Compound Name | LCMS (ESI) and $^{1}$H-NMR (400 MHz, $CDCl_3$) |
|---|---|---|---|
| 27 | 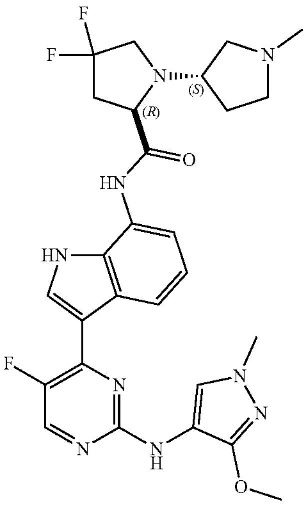 | (2R,3'S)-4,4-difluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 570 (M + H)+. $^{1}$H-NMR: δ 11.70 (s, 1H), 9.92 (s, 1H), 8.48 (d, J = 8.1 Hz, 1H), 8.18 (d, J = 3.7 Hz, 1H), 8.06-7.98 (m, 1H), 7.75 (s, 1H), 7.32 (d, J = 7.5 Hz, 1H), 7.21 (t, J = 7.8 Hz, 1H), 6.55 (s, 1H), 3.99 (s, 3H), 3.76 (s, 3H), 3.71-3.63 (m, 1H), 3.63-3.41 (m, 2H), 3.26-3.18 (m, 1H), 3.15-2.95 (m, 2H), 2.93-2.74 (m, 1H), 2.70-2.55 (m, 1H), 2.43-2.27 (m, 5H), 2.26-2.07 (m, 1H), 2.03-1.83 (m, 1H). |
| 28 | 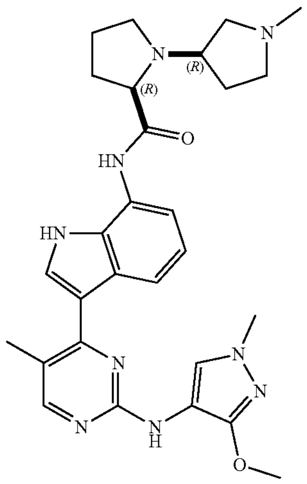 | (2R,3'R)-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 530 (M + H)+. $^{1}$H-NMR: δ 11.78 (s, 1H), 10.22 (s, 1H), 8.21 (s, 1H), 8.18 (d, J = 8.2 Hz, 1H), 7.83 (s, 1H), 7.61 (d, J = 2.3 Hz, 1H), 7.35 (d, J = 7.5 Hz, 1H), 7.17 (t, J = 7.8 Hz, 1H), 6.56 (s, 1H), 3.97 (s, 3H), 3.70 (s, 3H), 3.44-3.28 (m, 3H), 3.22-3.11 (m, 1H), 3.01-2.92 (m, 1H), 2.54-2.29 (m, 9H), 2.29-2.13 (m, 3H), 2.12-1.97 (m, 1H), 1.93-1.81 (m, 2H). |
| 29 | 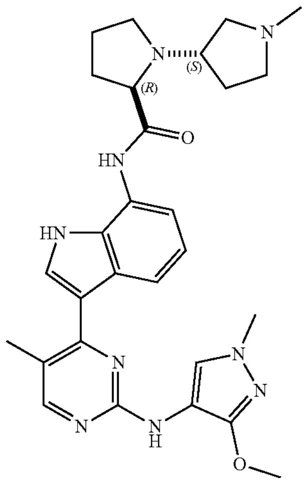 | (2R,3'S)-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 530 (M + H)+. $^{1}$H-NMR: δ 11.78 (s, 1H), 10.22 (s, 1H), 8.21 (s, 1H), 8.18 (d, J = 8.2 Hz, 1H), 7.83 (s, 1H), 7.61 (d, J = 2.3 Hz, 1H), 7.35 (d, J = 7.5 Hz, 1H), 7.17 (t, J = 7.8 Hz, 1H), 6.56 (s, 1H), 3.97 (s, 3H), 3.70 (s, 3H), 3.44-3.28 (m, 3H), 3.22-3.11 (m, 1H), 3.01-2.92 (m, 1H), 2.54-2.29 (m, 9H), 2.29-2.13 (m, 3H), 2.12-1.97 (m, 1H), 1.93-1.81 (m, 2H). |

TABLE 6-continued

| Example | Compound Structure | Compound Name | LCMS (ESI) and $^1$H-NMR (400 MHz, $CDCl_3$) |
|---|---|---|---|
| 30 | 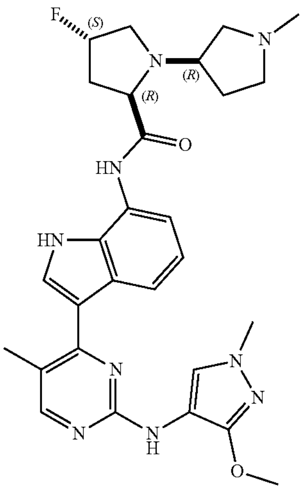 | (2R,3'R,4S)-4-fluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 548 (M + H)+. $^1$H-NMR: δ 11.58 (s, 1H), 10.07 (s, 1H), 8.28-8.11 (m, 2H), 7.82 (s, 1H), 7.61 (d, J = 2.3 Hz, 1H), 7.27 (d, J = 7.2 Hz, 1H), 7.16 (t, J = 7.8 Hz, 1H), 6.56 (s, 1H), 5.20 (d, J = 53.1 Hz, 1H), 3.97 (s, 3H), 3.78 (t, J = 8.7 Hz, 1H), 3.69 (s, 3H), 3.62-3.53 (m, 1H), 3.50-3.30 (m, 1H), 3.25-3.10 (m, 2H), 3.01-2.92 (m, 1H), 2.83-2.72 (m, 1H), 2.41-2.27 (m, 7H), 2.27-2.14 (m, 2H), 2.12-1.94 (m, 2H). |
| 31 | 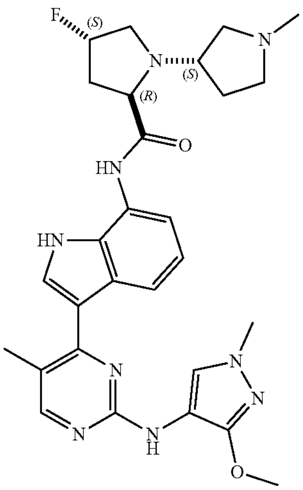 | (2R,3'S,4S)-4-fluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 548 (M + H)+. $^1$H-NMR: δ 11.58 (s, 1H), 10.07 (s, 1H), 8.28-8.11 (m, 2H), 7.82 (s, 1H), 7.61 (d, J = 2.3 Hz, 1H), 7.27 (d, J = 7.2 Hz, 1H), 7.16 (t, J = 7.8 Hz, 1H), 6.56 (s, 1H), 5.20 (d, J = 53.1 Hz, 1H), 3.97 (s, 3H), 3.78 (t, J = 8.7 Hz, 1H), 3.69 (s, 3H), 3.62-3.53 (m, 1H), 3.50-3.30 (m, 1H), 3.25-3.10 (m, 2H), 3.01-2.92 (m, 1H), 2.83-2.72 (m, 1H), 2.41-2.27 (m, 7H), 2.27-2.14 (m, 2H), 2.12-1.94 (m, 2H). |
| 32 | 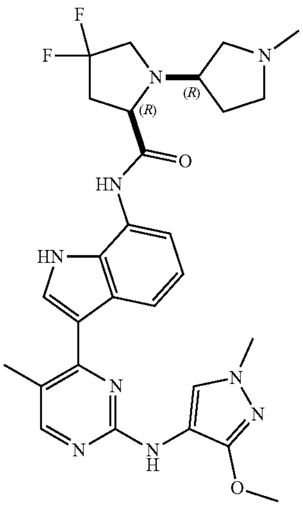 | (2R,3'R)-4,4-difluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 566 (M + H)+. $^1$H-NMR: δ 11.40 (s, 1H), 9.92 (s, 1H), 8.25-8.18 (m, 2H), 7.82 (s, 1H), 7.62 (d, J = 2.6 Hz, 1H), 7.27 (d, J = 7.5 Hz, 1H), 7.17 (t, J = 7.8 Hz, 1H), 6.56 (s, 1H), 3.98 (s, 3H), 3.74-3.64 (m, 4H), 3.60-3.42 (m, 2H), 3.22-3.14 (m, 1H), 3.11-2.92 (m, 2H), 2.90-2.72 (m, 1H), 2.69-2.54 (m, 1H), 2.42-2.27 (m, 8H), 2.24-2.12 (m, 1H), 2.04-1.89 (m, 1H). |

TABLE 6-continued

| Example | Compound Structure | Compound Name | LCMS (ESI) and $^1$H-NMR (400 MHz, $CDCl_3$) |
|---|---|---|---|
| 33 | 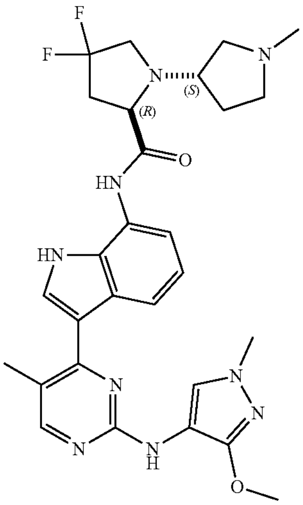 | (2R,3'S)-4,4-difluoro-N-(3-(2-((3-methoxy-1-methyl-1H-pyrazol-4-yl)amino)-5-methylpyrimidin-4-yl)-1H-indol-7-yl)-1'-methyl-[1,3'-bipyrrolidine]-2-carboxamide | 566 (M + H)+. $^1$H-NMR: δ 11.40 (s, 1H), 9.92 (s, 1H), 8.25-8.18 (m, 2H), 7.82 (s, 1H), 7.62 (d, J = 2.6 Hz, 1H), 7.27 (d, J = 7.5 Hz, 1H), 7.17 (t, J = 7.8 Hz, 1H), 6.56 (s, 1H), 3.98 (s, 3H), 3.74-3.64 (m, 4H), 3.60-3.42 (m, 2H), 3.22-3.14 (m, 1H), 3.11-2.92 (m, 2H), 2.90-2.72 (m, 1H), 2.69-2.54 (m, 1H), 2.42-2.27 (m, 8H), 2.24-2.12 (m, 1H), 2.04-1.89 (m, 1H). |
| 34 | 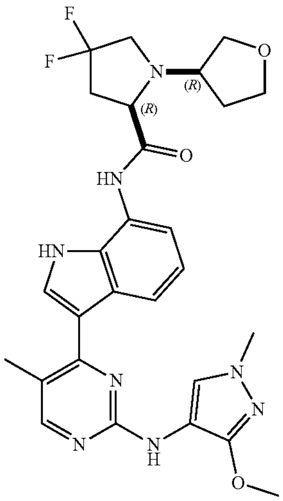 | (R)-4,4-difluoro-N-(3-(2-((3-methoxy-1-methyl-1H-pyrazol-4-yl)amino)-5-methylpyrimidin-4-yl)-1H-indol-7-yl)-1-((R)-tetrahydrofuran-3-yl)pyrrolidine-2-carboxamide | 553 (M + H)+. $^1$H-NMR: δ 10.85 (s, 1H), 9.38 (s, 1H), 8.32-8.12 (m, 2H), 7.80 (s, 1H), 7.71-7.54 (m, 1H), 7.24-7.06 (m, 2H), 6.60 (s, 1H), 4.36-4.13 (m, 1H), 4.12-3.90 (m, 4H), 3.80-3.63 (m, 4H), 3.62-3.48 (m, 2H), 3.20-3.03 (m, 1H), 2.94-2.74 (m, 1H), 2.73-2.55 (m, 1H), 2.35 (s, 3H), 2.25-2.04 (m, 2H), 1.92-1.69 (m, 2H). |
| 35 | 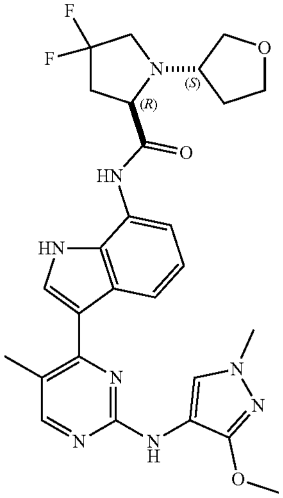 | (R)-4,4-difluoro-N-(3-(2-((3-methoxy-1-methyl-1H-pyrazol-4-yl)amino)-5-methylpyrimidin-4-yl)-1H-indol-7-yl)-1-((S)-tetrahydrofuran-3-yl)pyrrolidine-2-carboxamide | 553 (M + H)+. $^1$H-NMR: δ 10.85 (s, 1H), 9.38 (s, 1H), 8.32-8.12 (m, 2H), 7.80 (s, 1H), 7.71-7.54 (m, 1H), 7.24-7.06 (m, 2H), 6.60 (s, 1H), 4.36-4.13 (m, 1H), 4.12-3.90 (m, 4H), 3.80-3.63 (m, 4H), 3.62-3.48 (m, 2H), 3.20-3.03 (m, 1H), 2.94-2.74 (m, 1H), 2.73-2.55 (m, 1H), 2.35 (s, 3H), 2.25-2.04 (m, 2H), 1.92-1.69 (m, 2H). |

TABLE 6-continued

| Example | Compound Structure | Compound Name | LCMS (ESI) and $^{1}$H-NMR (400 MHz, $CDCl_3$) |
| --- | --- | --- | --- |
| 36 | 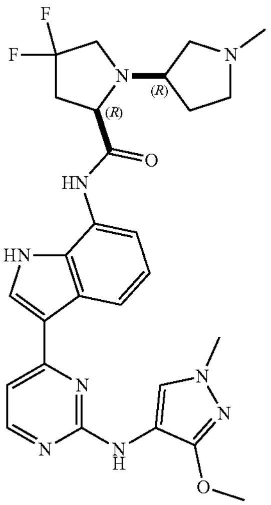 | (2R,3'R)-4,4-difluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 552 (M + H)+. $^{1}$H-NMR: δ 11.52 (s, 1H), 9.91 (s, 1H), 8.31 (d, J = 5.3 Hz, 1H), 8.24 (d, J = 8.0 Hz, 1H), 7.90-7.79 (m, 2H), 7.32-7.24 (m, 1H), 7.21 (t, J = 7.8 Hz, 1H), 6.99 (d, J = 5.3 Hz, 1H), 6.61 (s, 1H), 3.99 (s, 3H), 3.76 (s, 3H), 3.71-3.62 (m, 1H), 3.60-3.39 (m, 2H), 3.23-3.14 (m, 1H), 3.12-2.93 (m, 2H), 2.89-2.72 (m, 1H), 2.70-2.55 (m, 1H), 2.41-2.26 (m, 5H), 2.25-2.11 (m, 1H), 2.02-1.86 (m, 1H). |
| 37 | 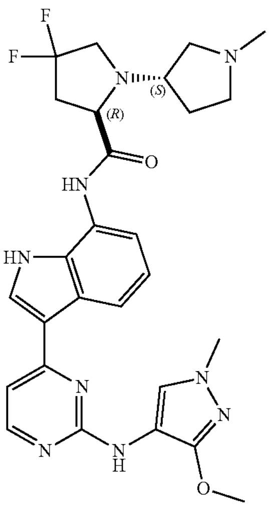 | (2R,3'S)-4,4-difluoro-N-(3-(2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 552 (M + H)+. $^{11}$H-NMR: δ 11.52 (s, 1H), 9.91 (s, 1H), 8.31 (d, J = 5.3 Hz, 1H), 8.24 (d, J = 8.0 Hz, 1H), 7.90-7.79 (m, 2H), 7.32-7.24 (m, 1H), 7.21 (t, J = 7.8 Hz, 1H), 6.99 (d, J = 5.3 Hz, 1H), 6.61 (s, 1H), 3.99 (s, 3H), 3.76 (s, 3H), 3.71-3.62 (m, 1H), 3.60-3.39 (m, 2H), 3.23-3.14 (m, 1H), 3.12-2.93 (m, 2H), 2.89-2.72 (m, 1H), 2.70-2.55 (m, 1H), 2.41-2.26 (m, 5H), 2.25-2.11 (m, 1H), 2.02-1.86 (m, 1H). |
| 38 | 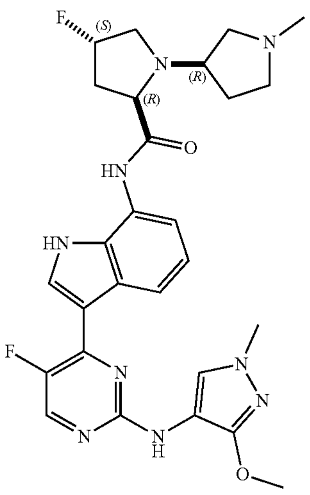 | (2R,3'R,4S)-4-fluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 552 (M + H)+. $^{1}$H-NMR: δ 11.84 (s, 1H), 10.36 (s, 1H), 8.42 (d, J = 8.1 Hz, 1H), 8.17 (d, J = 3.8 Hz, 1H), 8.07-7.95 (m, 1H), 7.74 (s, 1H), 7.49-7.32 (m, 1H), 7.25-7.18 (m, 1H), 6.57 (s, 1H), 5.23 (d, J = 53.1 Hz, 1H), 3.98 (s, 3H), 3.76 (t, J = 8.7 Hz, 1H), 3.67 (s, 3H), 3.60-3.53 (m, 1H), 3.51-3.32 (m, 1H), 3.26-3.11 (m, 2H), 3.00-2.91 (m, 1H), 2.82-2.72 (m, 1H), 2.52-2.32 (m, 4H), 2.27-2.16 (m, 2H), 2.12-1.96 (m, 2H). |

TABLE 6-continued

| Example | Compound Structure | Compound Name | LCMS (ESI) and $^1$H-NMR (400 MHz, $CDCl_3$) |
|---|---|---|---|
| 39 | 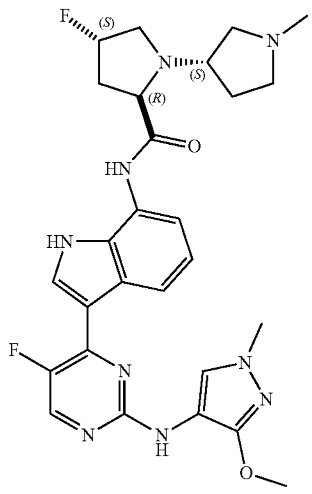 | (2R,3'S,4S)-4-fluoro-N-(3-(5-fluoro-2-((3-methoxy-1-methyl-1H-pyrazol-4-yl)amino)pyrimidin-4-yl)-1H-indol-7-yl)-1'-methyl-[1,3'-bipyrrolidine]-2-carboxamide | 552 (M + H)+. $^1$H-NMR: δ 12.08 (s, 1H), 10.23 (s, 1H), 8.44 (d, J = 8.1 Hz, 1H), 8.16 (d, J = 3.8 Hz, 1H), 8.05-7.93 (m, 1H), 7.75 (s, 1H), 7.51-7.36 (m, 1H), 7.24-7.17 (m, 1H), 6.54 (s, 1H), 5.21 (d, J = 53.1 Hz, 1H), 3.95 (s, 3H), 3.77 (t, J = 8.7 Hz, 1H), 3.68 (s, 3H), 3.62-3.55 (m, 1H), 3.50-3.31 (m, 1H), 3.25-3.09 (m, 2H), 3.01-2.94 (m, 1H), 2.83-2.75 (m, 1H), 2.43-2.27 (m, 4H), 2.24-2.14 (m, 2H), 2.10-1.93 (m, 2H). |

Example 40

(2R,4S)-4-fluoro-N-(3-(2-((3-methoxy-1-methyl-1H-pyrazol-4-yl)amino)pyrimidin-4-yl)-1H-indol-7-yl)-1-(1-methylpiperidin-4-yl)pyrrolidine-2-carboxamide

(1) Synthesis of methyl (2R,4S)-4-fluoro-1-(1-methylpiperidin-4-yl)pyrrolidine-2-carboxylate

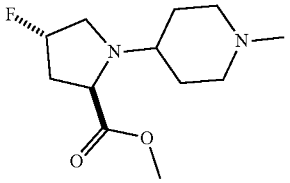 [SMILES: COC(=O)[C@H]1C[C@H](F)CN1C1CCN(C)CC1]

In a 100 mL round-bottom flask in an ice-water bath, 1-(t-butyl) 2-methyl (2R,4S)-4-fluoropyrrolidine-1,2-dicarboxylate (1.0 g, 4.0 mmol) was dissolved in $CH_2Cl_2$ (50 mL). TFA (10 mL) was added to the above solution and reacted for 2 h at room temperature. After the reaction was completed, the solution was concentrated under reduced pressure to remove TFA and the solvent. The residue was dissolved in MeOH (50 mL), cooled in an ice-water bath, added with N-methyl-piperidin-4-one (678 mg, 6.0 mmol) and sodium cyanoborohydride (378 mg, 6.0 mmol) and reacted for 20 h. After the reaction was completed, the solution was filtered with Celite and washed with methanol, the filtrate was collected and concentrated under reduced pressure to remove methanol, and the resulting residue was directly used in the next step. The product (1.2 g) was obtained. LCMS (ESI): m/z=245 $(M+H)^+$.

(2) Synthesis of (2R,4S)-4-fluoro-1-(1-methylpiperidin-4-yl)pyrrolidine-2-carboxylate hydrochloride

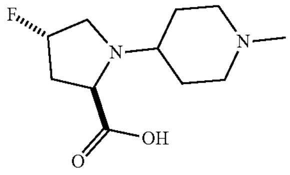

2HCl

In a 100 mL round-bottom flask, methyl (2R,4S)-4-fluoro-1-(1-methylpiperidin-4-yl)pyrrolidine-2-carboxylate (1.2 g, 4.9 mmol) and 6 M hydrochloric acid (50 mL) were added and heated to reflux for 6 h. After the reaction was completed, the solution was concentrated under reduced pressure to remove the solvent. The residue was added to isopropanol (150 mL), heated with stirring to 100° C. to be completely dissolved, reacted for 30 min to gradually precipitate a solid and reacted for 2 h. Then, the solution was naturally cooled to room temperature and stirred for 10 h. The solution was filtered and the filter residue was washed with isopropanol and dried to obtain the target product (850 mg) with a yield of 70% over two steps. LCMS (ESI): m/z=231 $(M+H)^+$.

(3) Synthesis of (2R,4S)-4-fluoro-N-(3-(2-((3-methoxy-1-methyl-1H-pyrazol-4-yl)amino) pyrimidin-4-yl)-1H-indol-7-yl)-1-(1-methylpiperidin-4-yl) pyrrolidine-2-carboxamide

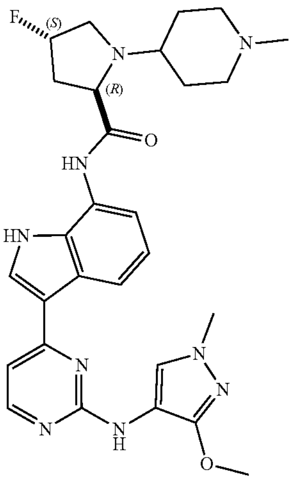

In a 50 mL round-bottom flask, Intermediate 3 (191 mg, 0.57 mmol) and (2R,4S)-4-fluoro-1-(1-methylpiperidin-4-yl)pyrrolidine-2-carboxylate hydrochloride (172 mg, 0.57 mmol) were dissolved in DMF (5 mL), added with DIEA (294 mg, 2.3 mmol) and HATU (260 mg, 0.68 mmol) and reacted for 1 h at room temperature. After the reaction was completed, the solution was diluted with $CH_2Cl_2$. The organic phase was washed with water, dried over anhydrous $Na_2SO_4$, filtered and concentrated. The resulting residue was isolated and purified through silica gel column chromatography (mobile phase: a mixed solution of $CH_2Cl_2$ and MeOH with a volume ratio of 10:1) to obtain the product (245 mg) with a yield of 78%. LCMS (ESI): m/z=548 $(M+H)^+$. $^1$H-NMR (400 MHz, $CDCl_3$): δ 11.30 (s, 1H), 9.74 (s, 1H), 8.34-8.26 (m, 2H), 7.88 (d, J=2.8 Hz, 1H), 7.83 (s, 1H), 7.14 (t, J=7.8 Hz, 1H), 6.98 (d, J=5.4 Hz, 1H), 6.77 (d, J=7.5 Hz, 1H), 6.63 (s, 1H), 5.20 (d, J=53.6 Hz, 1H), 3.99 (s, 3H), 3.94-3.84 (m, 1H), 3.76 (s, 3H), 3.53-3.35 (m, 1H), 3.32-3.16 (m, 1H), 2.98-2.85 (m, 2H), 2.80 (s, 1H), 2.77-2.55 (m, 2H), 2.26 (s, 3H), 2.17-2.01 (m, 1H), 2.01-1.87 (m, 3H), 1.76-1.60 (m, 2H).

Test Example 1

The JAK1 inhibitory activity and the JAK2 inhibitory activity of the amide compounds provided in the above examples were tested by the method below.

The inhibitory activity ($IC_{50}$) of the amide compound for JAK1 and JAK2 under 1 mM ATP was measured by a mobility shift assay method. JAK1 was purchased from Carna Corporation (Cat. No. 08-144, Lot No. 11CBS-0144V) and JAK2 was purchased from Carna Corporation (Cat. No. 08-045, Lot No. 10CBS-0289R). JAK1 Peptide was purchased from GL (Cat. No. 758318, Lot No. P191104-TL758318) and Kinase substrate22 was purchased from GL (Cat. No. 112393, Lot No. P200403-CL112393). The positive control compound used was baricitinib. Specific steps are described below.

1. A 1× Kinase buffer was formulated.
2. Concentration gradients of the compound were formulated: a test compound with an initial concentration of 10000 nM (JAK1) or 30000 nM (JAK2) was diluted in a 384-well plate to a 100% DMSO solution with a 100-fold final concentration, wherein the compound was diluted by a fold of 3 to 10 concentrations. 250 nL of the compound with the 100-fold final concentration was transferred with a dispenser Echo 550 to the target plate.
3. A kinase solution with a 2.5-fold final concentration was prepared with the 1× Kinase buffer.
4. 10 μL of the kinase solution with the 2.5-fold final concentration was added to compound wells and positive control wells, separately; and 10 μL of 1× Kinase buffer was added to negative control wells.
5. The plate was centrifuged at 1000 rpm for 30 s, shaken and uniformly mixed, and incubated for 10 min at room temperature.
6. A mixed solution of ATP (the final concentration of ATP=1 mM) and Kinase substrate with a 5/3-fold final concentration was formulated with the 1× Kinase buffer.
7. 15 μL of the mixed solution of ATP and the substrate with the 5/3-fold final concentration was added to initiate the reaction.
8. The 384-well plate was centrifuged at 1000 rpm for 30 s, shaken and uniformly mixed, and incubated for respective times at room temperature.
9. The kinase reaction was stopped by adding 30 μL of a detection termination solution, and the plate was centrifuged at 1000 rpm for 30 s and shaken and uniformly mixed.
10. The conversion rate was read with Caliper EZ Reader and the half maximal inhibitory concentration ($IC_{50}$) was calculated. The data were shown in Table 7.

TABLE 7

| Example | JAK1 $IC_{50}$ (nM) 1 mM ATP | JAK2 $IC_{50}$ (nM) 1 mM ATP |
|---|---|---|
| 1 | 73 | 2815 |
| 2 | 137 | 1847 |
| 3 | 70 | 2208 |
| 4 | 53 | 652 |
| 5 | 55 | 4302 |
| 6 | 68 | 4001 |
| 7 | 152 | 4406 |
| 8 | 1168 | 10482 |
| 9 | 51 | 5001 |
| 10 | 104 | 14613 |
| 11 | 69 | 12069 |
| 12 | 103 | 12031 |
| 13 | 101 | 14488 |
| 14 | 41 | 6622 |
| 15 | 27 | 3641 |
| 16 | 40 | 3339 |
| 17 | 216 | 10484 |
| 18 | 108 | 10229 |
| 19 | 368 | 15469 |
| 20 | 120 | 21451 |
| 21 | 262 | >30000 |
| 22 | 46 | 7279 |
| 23 | 59 | 5370 |
| 24 | 40 | 14567 |
| 25 | 68 | 12448 |
| 26 | 48 | 5487 |
| 27 | 60 | 4395 |
| 28 | 40 | 16296 |
| 29 | 67 | 13448 |
| 30 | 33 | 5165 |

TABLE 7-continued

| Example | JAK1 $IC_{50}$ (nM) 1 mM ATP | JAK2 $IC_{50}$ (nM) 1 mM ATP |
|---|---|---|
| 31 | 92 | 11865 |
| 32 | 26 | 3885 |
| 33 | 39 | 3428 |
| 34 | 161 | 2513 |
| 35 | 115 | 1888 |
| 36 | 91 | 11986 |
| 37 | 216 | 10837 |
| 38 | 34 | 5275 |
| 39 | 50 | 4850 |
| 40 | 259 | 24346 |
| baricitinib | 9.3 | 9.0 |
| abrocitinib | 49 | 873 |
| AZD4205 | 56 | 4019 |

As can be seen from the test data in Table 7, the amide compound provided in the present application can effectively inhibit JAK1 under 1 mM ATP. Moreover, the JAK1 inhibitory activity of the amide compound of the present application is higher than its JAK2 inhibitory activity and the amide compound has high JAK1 selectivity. Compared with two JAK1 inhibitors abrocitinib and AZD4205, most compounds of the present application has higher selectivity in inhibiting JAK1 than inhibiting JAK2.

Test Example 2

Cytokine IFNα can induce STAT3 phosphorylation (pSTAT3) through the JAK1/TYK2 signaling pathway. In the present application, the inhibition of INFα-induced pSTAT3 by the compounds provided in Examples 30 and 32 of the present application was tested by using a mouse whole blood assay, and meanwhile, two selective JAK1 inhibitors abrocitinib and AZD4205 were tested for comparison. IFNα used was Recombinant mouse IFNα (Miltenyi #130-093-131), the pSTAT3 antibody used was Alexa Fluor 488 anti-STAT3 Phospho (Tyr705) Antibody (Biolegend #651106), and the CD3 antibody used was Brilliant Violet 421 anti-mouse CD3 Antibody (Biolegend #100228). The cytokine dilution buffer was PBS+0.1% BSA, which was filtered and stored at −4° C. The FACS buffer was PBS+0.2% BSA+1 mM EDTA. Specific steps are described below.

1. C57BL/6J mouse blood was added to a 96-well plate, with 90 μL per well.
2. Each well was added with 5 μL of the compound (19×), uniformly mixed and incubated at 37° C. for 60 min in an incubator.
3. Each well was added with 5 μL of 20×IFNα (with a working concentration of 20000 IU/mL) as the stimulation factor, uniformly mixed and incubated at 37° C. for 30 min.
4. Blood was transferred to a 96-deep-well plate, and each well was added with 1 mL of Lyse fix buffer (1×), uniformly mixed and incubated at 37° C. for 10 min.
5. The plate was centrifuged at 600 g for 5 min and the supernatant was discarded. 1 mL of PBS was added to each well and centrifuged at 600 g for 5 min and the supernatant was discarded, which were repeated twice. Each well was added with 100 μL of the anti-mCD3 antibody (diluted by a fold of 80 with the cytokine dilution buffer), uniformly mixed and incubated at 4° C. for 30 min.
6. 1 mL of PBS was added to each well and centrifuged at 600 g for 5 min and the supernatant was discarded, which were repeated twice. Each well was added with 1000 μL of Perm III, uniformly mixed and incubated at 4° C. for 30 min.
7. The plate was centrifuged at 600 g for 5 min and the supernatant was discarded. 1 mL of PBS was added to each well and centrifuged at 600 g for 5 min and the supernatant was discarded, which were repeated twice.
8. Each well was added with 100 μL of the anti-pSTAT3 antibody (diluted by a fold of 50 with the FACS buffer), uniformly mixed and incubated at 25° C. for 40 min.
9. 1 mL of the FACS buffer was added to each well and centrifuged at 600 g for 5 min and the supernatant was discarded. 200 μL of the FACS buffer was added to each well and resuspended. All samples were transferred to a 96-well tip-bottom plate and uploaded.
10. Data were collected and analyzed. The 50% inhibition rates ($IC_{50}$) are listed in Table 8.

TABLE 8

| Compound | JAK1 $IC_{50}$ (nM) 1 mM ATP | JAK2 $IC_{50}$ (nM) 1 mM ATP | JAK2/ JAK1 Multiple selectivity | Mouse Whole Blood IFNα-induced pSTAT3 $IC_{50}$ (nM) |
|---|---|---|---|---|
| Example 30 | 33 | 5162 | 156 | 127 |
| Example 32 | 26 | 3885 | 149 | 121 |
| abrocitinib | 49 | 873 | 18 | 204 |
| AZD4205 | 56 | 4019 | 72 | 173 |

As can be seen from the test results in Table 8, the compounds of the present application can effectively inhibit the JAK1/TYK2 signaling pathway in the mouse whole blood assay and the $IC_{50}$ of Example 30 and the $IC_{50}$ of Example 32 for inhibiting IFNα-induced pSTAT3 expression are 127 nM and 121 nM, respectively and are higher than the inhibitory activity of two selective JAK1 inhibitors abrocitinib and AZD4205.

The applicant has stated that although the amide compound, the pharmaceutical composition and the use thereof in the present application are described through the preceding embodiments, the present application is not limited to the preceding embodiments, which means that the implementation of the present application does not necessarily depend on the preceding embodiments. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

What is claimed is:

1. An amide compound having a structure represented by Formula IA or Formula 1B:

Formual IA

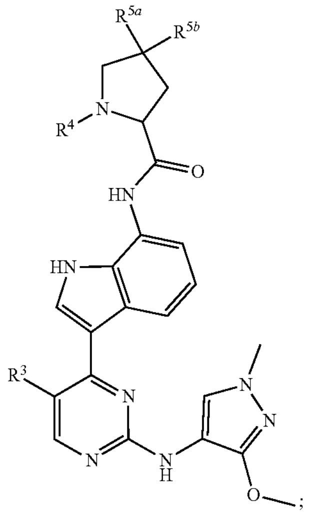

$R^3$ is selected from H, F, Cl, or C1 to C6 linear or branched alkyl;

$R^4$ is selected from $SO_2R^{a2}$, wherein $R^{a2}$ is selected from C1 to C6 linear or branched alkyl;

$R^{5a}$ and R5b are each independently selected from H, F, methoxy or ethoxy; or Formual IB

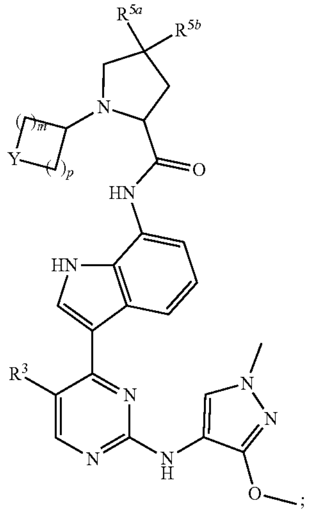

wherein $R^3$, $R^{5a}$ and $R^{5b}$ are each independently defined within the same ranges as in Formula IA;

Y is selected from $NR^7$ or O;

$R^7$ is selected from H, and C1 to C6 linear or branched alky;

m is 1 or 2, and p is 2.

2. The amide compound according to claim 1, wherein $R^3$ is selected from H, F, or methyl.

3. The amide compound according to claim 1, wherein $R^7$ is H or methyl.

4. The amide compound according to claim 1, wherein the amide compound comprises the following compounds:

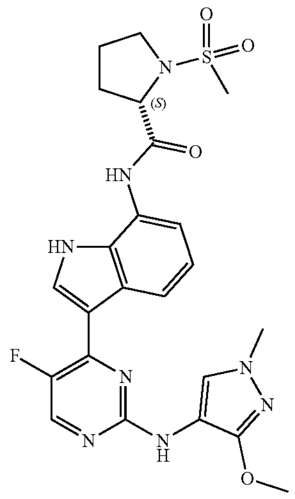

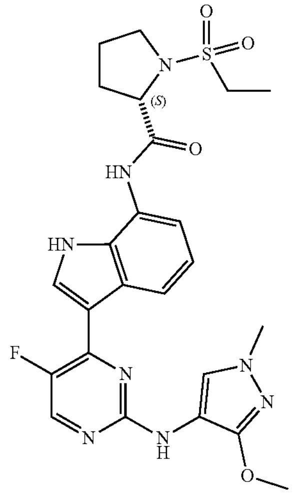

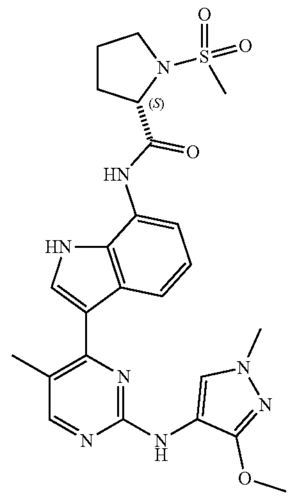

-continued
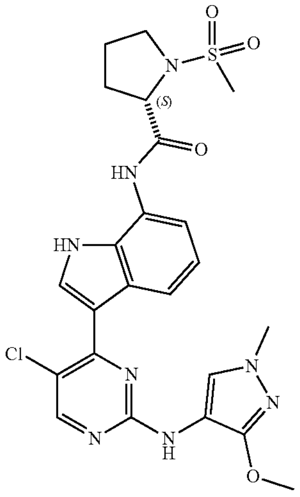
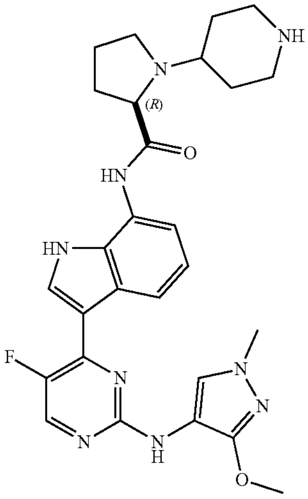
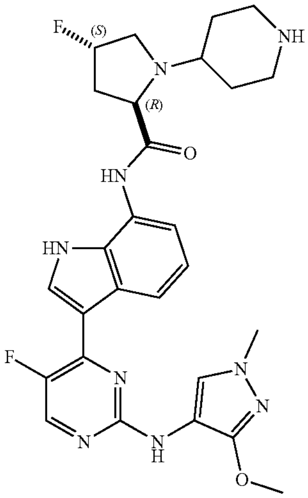
-continued
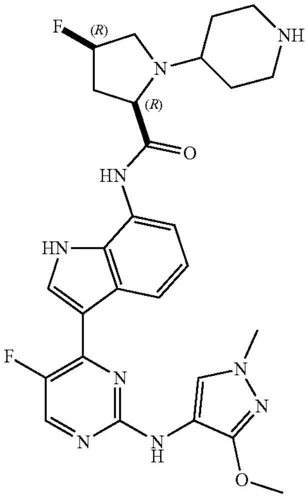
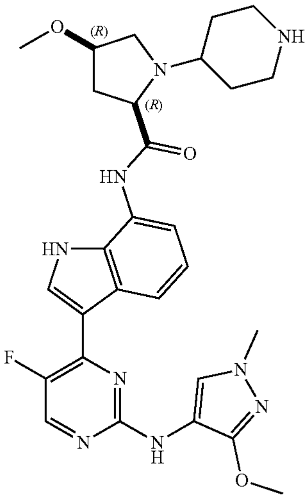
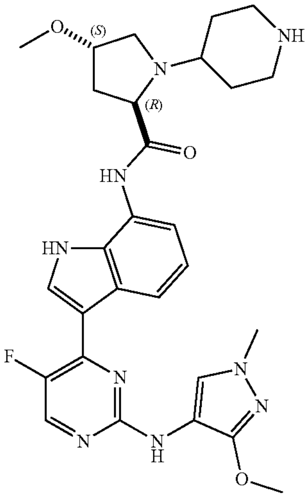

-continued
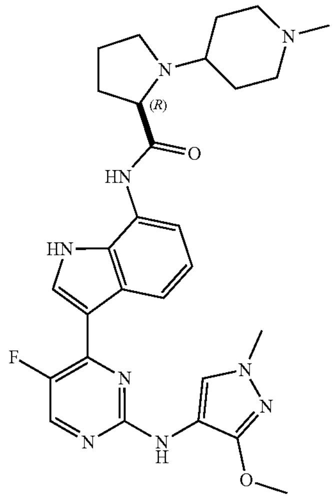
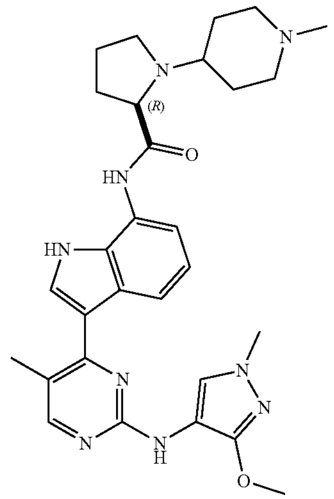
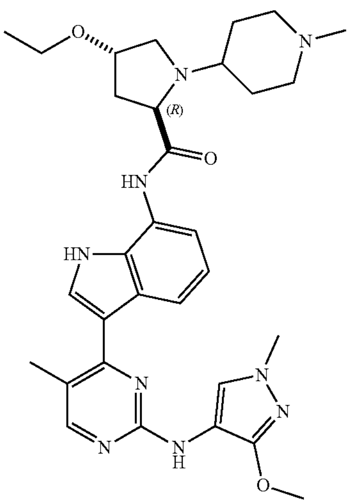
-continued
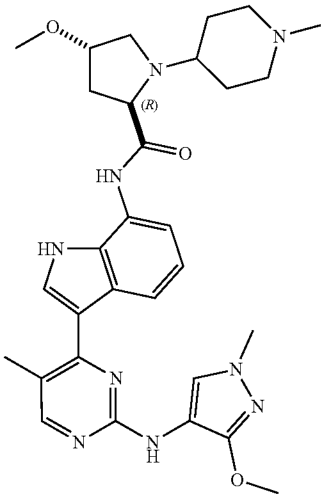
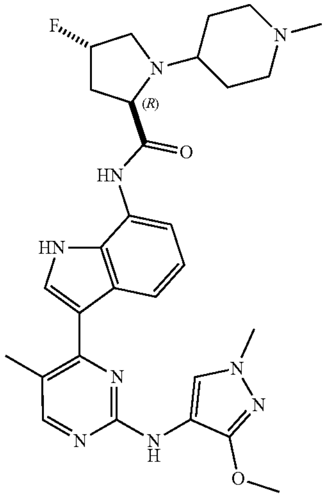
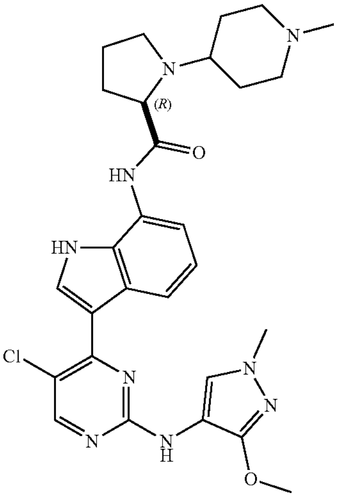

-continued
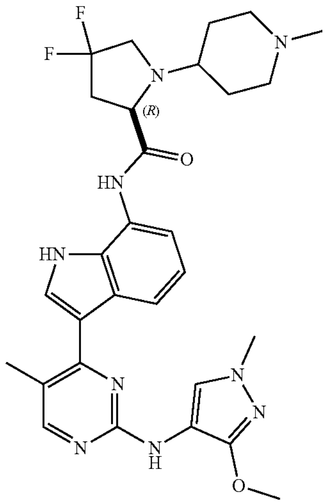
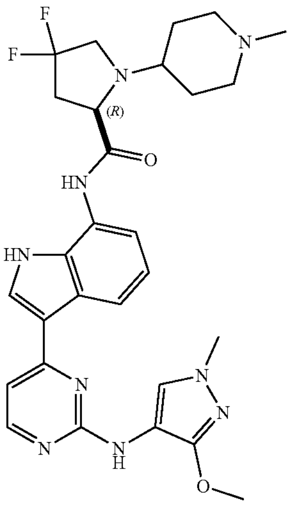
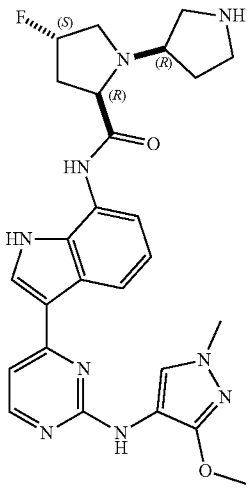
-continued
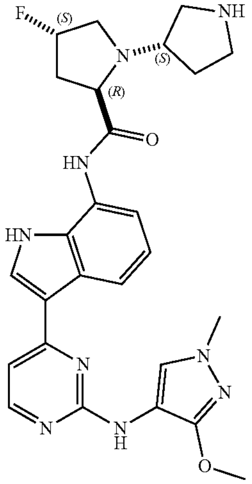
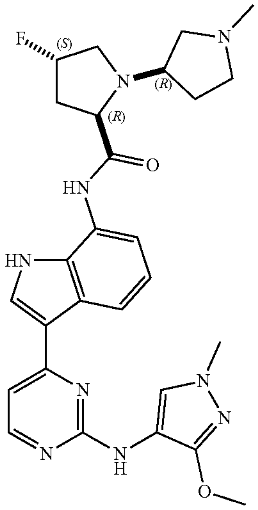
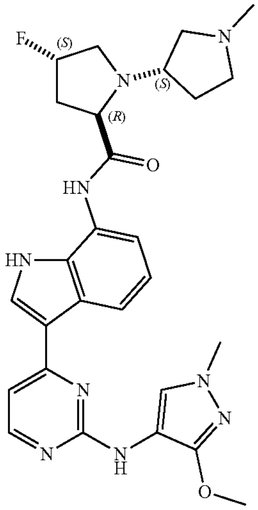

-continued
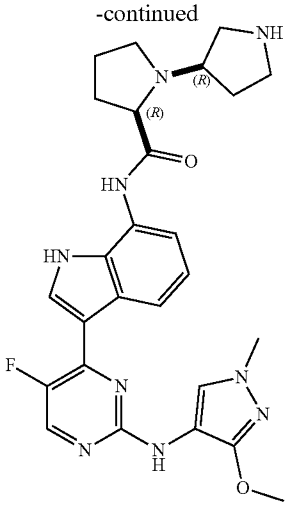
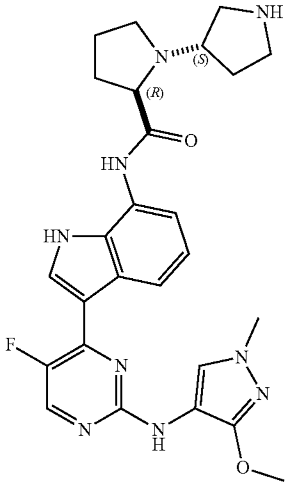
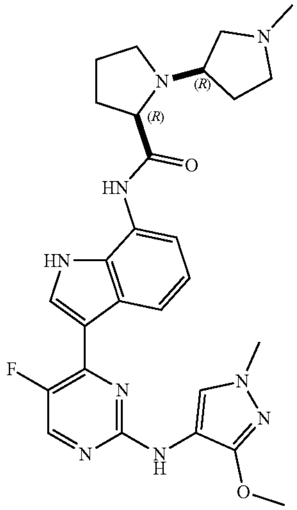
-continued
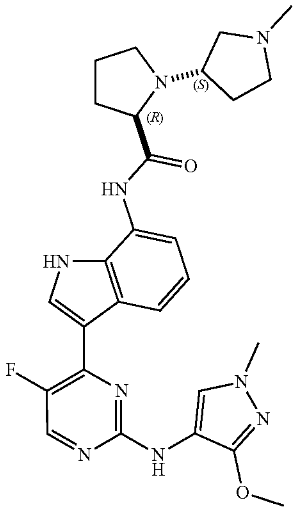
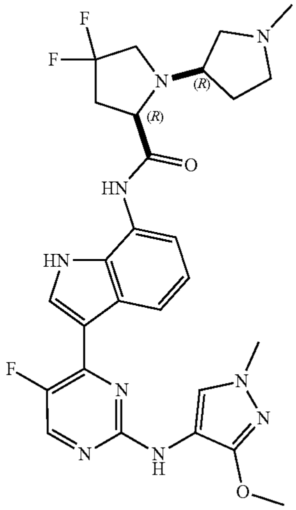
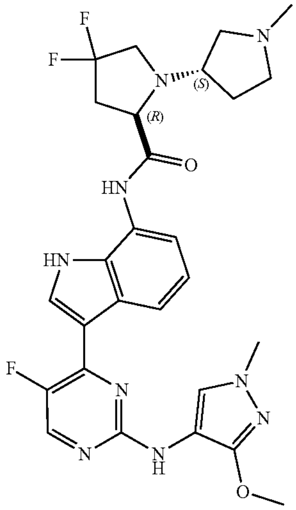

-continued
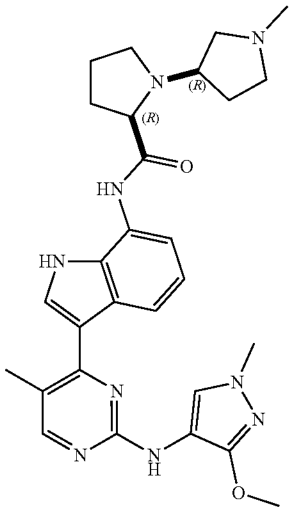
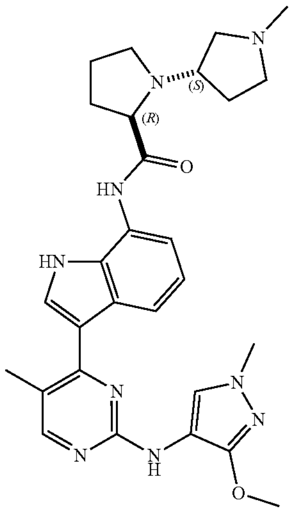
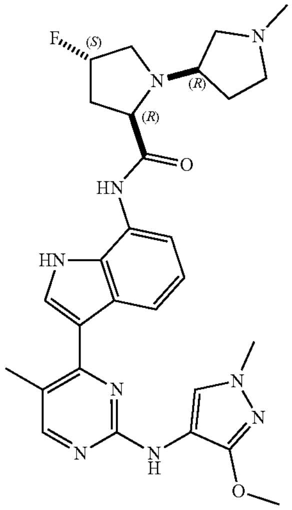
-continued
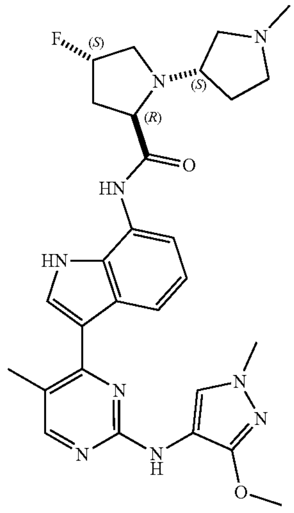
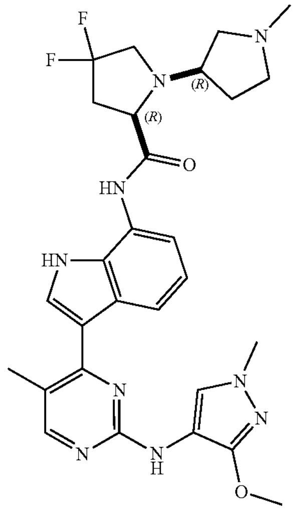
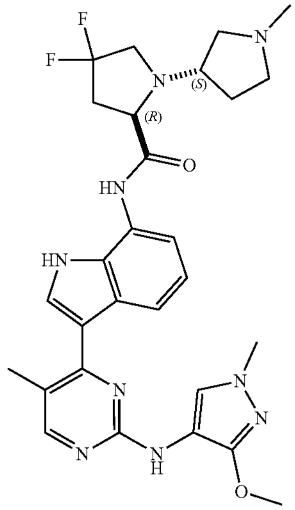

-continued
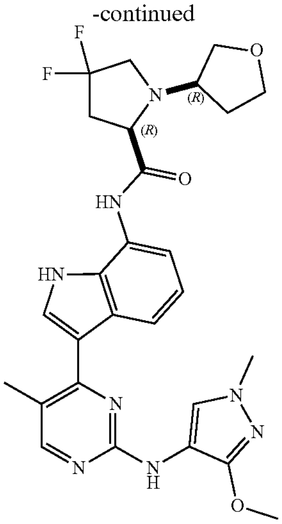
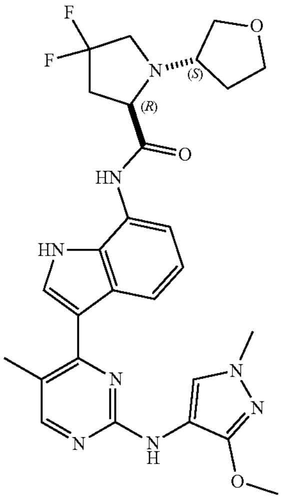
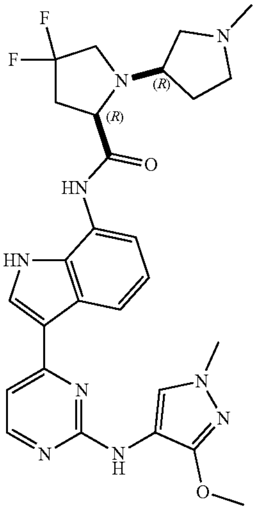
-continued
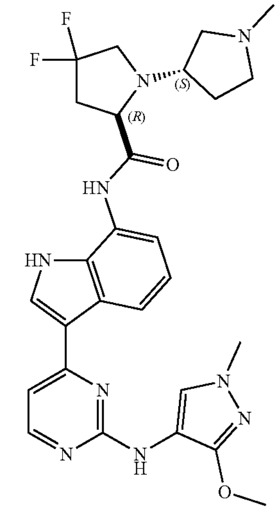
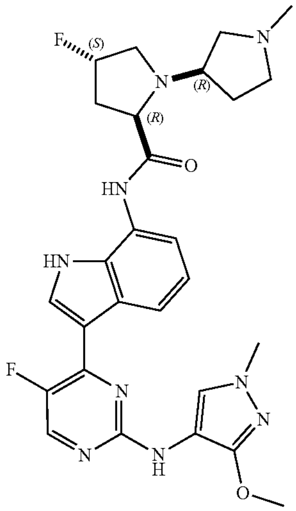
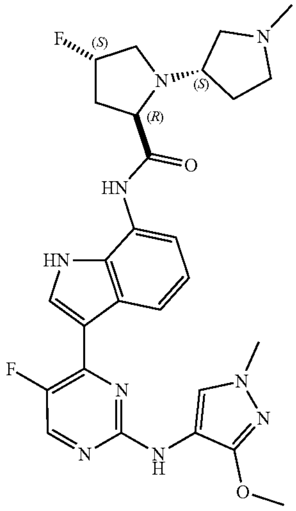

-continued

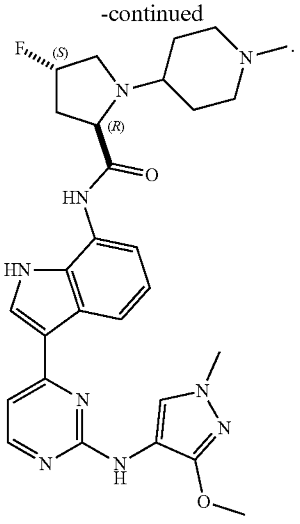

5. A stereoisomer, geometric isomer, tautomer or pharmaceutically acceptable salt of the amide compound according to claim 1.

6. A pharmaceutical composition, comprising an active ingredient and at least one pharmaceutical carrier or excipient; wherein the active ingredient comprises any one or a combination of at least two of the amide compound according to claim 1.

* * * * *